US012214088B2

(12) United States Patent
Emgenbroich et al.

(10) Patent No.: US 12,214,088 B2
(45) Date of Patent: *Feb. 4, 2025

(54) TRANSDERMAL THERAPEUTIC SYSTEM FOR THE TRANSDERMAL ADMINISTRATION OF GUANFACINE COMPRISING AT LEAST ONE ADDITIVE

(71) Applicants: LTS LOHMANN THERAPIE-SYSTEME AG, Andernach (DE); DDP Specialty Electronic Materials US 9, LLC, Wilmington, DE (US)

(72) Inventors: Marco Emgenbroich, Rheinbach (DE); Eva-Marie Prinz, Weissenthurm (DE); Elke Klein, Bad Neuenahr-Ahrweiler (DE); Heike Kluth, Ochtendung (DE); Xavier Thomas, Famars (FR); Linda Sue Nartker, Midland, MI (US)

(73) Assignees: LTS LOHMANN THERAPIE-SYSTEME AG, Andernach (DE); DDP SPECIALTY ELECTRONIC MATERIALS US 9, LLC, Wilmington, DE (US)

( * ) Notice: Subject to any disclaimer, the term of this patent is extended or adjusted under 35 U.S.C. 154(b) by 1247 days.

This patent is subject to a terminal disclaimer.

(21) Appl. No.: 16/755,049

(22) PCT Filed: Oct. 11, 2018

(86) PCT No.: PCT/EP2018/077792
§ 371 (c)(1),
(2) Date: Apr. 9, 2020

(87) PCT Pub. No.: WO2019/072998
PCT Pub. Date: Apr. 18, 2019

(65) Prior Publication Data
US 2020/0397715 A1 Dec. 24, 2020

Related U.S. Application Data
(60) Provisional application No. 62/570,745, filed on Oct. 11, 2017.

(30) Foreign Application Priority Data
Dec. 5, 2017 (EP) .................................. 17205546

(51) Int. Cl.
| A61K 9/70 | (2006.01) |
| A61K 31/165 | (2006.01) |
| A61K 47/08 | (2006.01) |
| A61K 47/10 | (2017.01) |
| A61K 47/32 | (2006.01) |
| A61P 9/12 | (2006.01) |
| A61P 25/00 | (2006.01) |

(52) U.S. Cl.
CPC .......... *A61K 9/7084* (2013.01); *A61K 9/7069* (2013.01); *A61K 31/165* (2013.01); *A61K 47/08* (2013.01); *A61K 47/10* (2013.01); *A61K 47/32* (2013.01)

(58) Field of Classification Search
CPC ...... A61K 31/165; A61K 47/08; A61K 47/10; A61K 47/32; A61K 9/7069; A61K 9/7084; A61P 25/00; A61P 9/12
See application file for complete search history.

(56) References Cited

U.S. PATENT DOCUMENTS

| 5,028,431 A | 7/1991 | Franz et al. |
| 5,656,286 A | 8/1997 | Miranda et al. |
| 5,762,952 A * | 6/1998 | Barnhart ................... A61P 9/00 424/448 |
| 5,843,472 A | 12/1998 | Ma et al. |
| 11,576,874 B2 | 2/2023 | Emgenbroich et al. |
| 2007/0053968 A1 | 3/2007 | Tatapudy et al. |
| 2012/0108560 A1 | 5/2012 | Evans et al. |
| 2013/0276672 A1 | 10/2013 | Amiel et al. |
| 2015/0342899 A1 | 12/2015 | Kulakofsky et al. |
| 2016/0030362 A1 | 2/2016 | Liao et al. |
| 2020/0397714 A1 | 12/2020 | Emgenbroich et al. |
| 2021/0000756 A1 | 1/2021 | Emgenbroich et al. |
| 2023/0241004 A1 | 8/2023 | Emgenbroich et al. |

FOREIGN PATENT DOCUMENTS

| CN | 1640500 A | 7/2005 |
| CN | 101304734 A | 11/2008 |
| CN | 103096931 A | 5/2013 |

(Continued)

OTHER PUBLICATIONS

Biederman; "New Developments in the Treatment of Attention-Deficit/Hyperactivity Disorder"; J. Clin. Psychiatry; 2006; 67 (suppl 8); published in 2006.*
Murthy et al.; Handbook of Non-invasive Drug Delivery Systems; Chapter 1: Topical and Transdermal Drug Delivery; 36 pages; published 2010.*
Office Action mailed Jun. 16, 2021, in U.S. Appl. No. 16/755,043, Emgenbroich, M., et al., § 371(c) date Apr. 9, 2020, 20 pages.
Office Action mailed Jan. 7, 2022, in U.S. Appl. No. 16/755,043, Emgenbroich, M., et al., § 371(c) date Apr. 9, 2020, 24 pages.
Notice of Allowance mailed Mar. 22, 2023, in U.S. Appl. No. 16/755,048, Emgenbroich, M., et al., § 371(c) date Apr. 9, 2020, 8 pages.
Office Action mailed Sep. 2, 2021, in U.S. Appl. No. 16/755,048, Emgenbroich, M., et al., § 371(c) date Apr. 9, 2020, 14 pages.
Office Action mailed May 5, 2022, in U.S. Appl. No. 16/755,048, Emgenbroich, M., et al., § 371(c) date Apr. 9, 2020, 16 pages.

(Continued)

Primary Examiner — Jeffrey T. Palenik
(74) Attorney, Agent, or Firm — Sterne, Kessler, Goldstein & Fox P.L.L.C.

(57) ABSTRACT

The present invention relates to a transdermal therapeutic system for the transdermal administration of guanfacine comprising a guanfacine-containing layer structure, said guanfacine-containing layer structure comprising: A) a backing layer; and B) a guanfacine-containing layer; wherein the transdermal therapeutic system comprises at least one polymer and at least additive.

10 Claims, 6 Drawing Sheets

(56) References Cited

FOREIGN PATENT DOCUMENTS

| | | |
|---|---|---|
| EP | 0180377 A2 | 5/1986 |
| EP | 0314528 A1 | 5/1989 |
| EP | 0622075 A1 | 11/1994 |
| EP | 2599847 A1 | 6/2013 |
| EP | 2599501 B1 | 11/2014 |
| JP | S61158920 A | 7/1986 |
| JP | H01265021 A | 10/1989 |
| JP | H07145048 A | 6/1995 |
| JP | H09511987 A | 12/1997 |
| JP | 2007284370 A | 11/2007 |
| JP | 2009540052 A | 11/2009 |
| KR | 20130044380 A | 5/2013 |
| WO | WO-9518603 A1 | 7/1995 |
| WO | WO-2007145996 A2 | 12/2007 |
| WO | WO-2010124187 A2 | 10/2010 |
| WO | WO-2016130408 A1 | 8/2016 |
| WO | WO-2017048595 A1 | 3/2017 |
| WO | WO-2019072996 A1 | 4/2019 |
| WO | WO-2019072997 A1 | 4/2019 |
| WO | WO-2019072998 A1 | 4/2019 |
| WO | WO-2019175101 A1 | 9/2019 |

OTHER PUBLICATIONS

Notice of Allowance mailed Oct. 13, 2022, in U.S. Appl. No. 16/755,043, Emgenbroich, M., et al., § 371(c) date Apr. 9, 2020, 7 pages.
Kharkevich, D. A., "6. Dependence of the Pharmacotherapeutic Effect on the Properties of Medicines and the Conditions of their Use," in Pharmacology, $3^{rd}$ Ed., pp. 47-48, Moscow Medicine, Russia (1987).
Chuyeshov, V.I., et al., "14.8 Factors Affecting the Main Qualities of Tablets—Mechanical Strength, Disintegration and Average Weight," in Industrial Drug Technology, vol. 2: 352-355, Ed. Chuyeshov, V.I., MKT-KN Publishing House, Ukraine (2002).
Notice of Allowance mailed Jul. 13, 2023, in U.S. Appl. No. 16/755,048, Emgenbroich, M., et al., § 371(c) date Apr. 9, 2020, 9 pages.
English Machine Translation of JP-H07145048-A published on Jun. 6, 1995 (cited as document FP3 in an IDS filed Sep. 11, 2020), European Patent Office (Jan. 21, 2019), 5 pages.
An English language abstract of JP-H07145048-A published on Jun. 6, 1995 (cited as document FP3 in an IDS filed Sep. 11, 2020), Database WPI: Database Accession No. 1995-237135, XP002780837, Thomson Scientific, United Kingdom (2017).
Elia, J., et al., "Methylphenidate transdermal system: clinical applications for attention-deficit/hyperactivity disorder," Expert Rev. Clin. Pharmacol. 4(3):311-328, Informa, United Kingdom (2011).
Kaplan, G., et al., "Pharmacotherapy for Child and Adolescent Attention-deficit Hyperactivity Disorder," Pediatric Clinics of North America, 58:99-120, Saunders, United States (2011).
Bernknopf, A., "Guanfacine (Intuniv) for Attention-Deficit/ Hyperactivity Disorder," Am. Fam. Physician 83(4):468-475, American Academy of Family Physicians, United States (2011).
Sutyagin, B., et al., *Chemistry and Physics of Polymers*, pp. 142-143, TPU Publishing House, Russia (2003).
International Search Report and Written Opinion in PCT/EP2018/ 077792 mailed Jan. 21, 2019, European Patent Office, Netherlands, 10 pages.
International Search Report and Written Opinion in PCT/EP2018/ 077791 mailed Dec. 21, 2018, European Patent Office, Netherlands, 10 pages.
International Search Report and Written Opinion in PCT/EP2018/ 077790 mailed Jan. 21, 2019, European Patent Office, Netherlands, 12 pages.
Office Action mailed Sep. 14, 2023, in U.S. Appl. No. 18/152,965, Emgenbroich, M., et al., filed Jan. 11, 2023, 16 pages.
Office Action mailed Nov. 9, 2023, in U.S. Appl. No. 16/755,048, Emgenbroich, M., et al., § 371(c) date Apr. 9, 2020, 17 pages.
Park, E.-S., et al., "Enhancing effect of polyoxyethylene alkyl ethers on the skin permeation of ibuprofen," International Journal of Pharmaceutics 209:109-119, Elsevier, Netherlands (2000).
Office Action mailed Feb. 15, 2024, in U.S. Appl. No. 18/152,965, Emgenbroich, M., et al., filed Jan. 11, 2023, 8 pages.

* cited by examiner

TRANSDERMAL THERAPEUTIC SYSTEM FOR THE TRANSDERMAL ADMINISTRATION OF GUANFACINE COMPRISING AT LEAST ONE ADDITIVE

TECHNICAL FIELD OF THE INVENTION

The present invention relates to a transdermal therapeutic system (TTS) for the transdermal administration of guanfacine to the systemic circulation, and processes of manufacture, method of treatments and uses thereof.

BACKGROUND OF THE INVENTION

The active agent guanfacine (also known as N-(amino-iminomethyl)-2,6-dichloro-benzeneacetamide, $C_9H_9Cl_2N_3O$, CAS No. 29110-47-2) is a sympatholytic drug used to treat hypertension and attention deficit hyperactivity disorder (ADHD). It is a centrally acting alpha(2)-adrenergic receptor agonist. It has the following chemical formula.

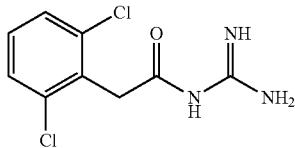 [SMILES: N=C(N)NC(=O)Cc1c(Cl)cccc1Cl]

Currently, guanfacine is commercially available, e.g., in the form of immediate or controlled release tablets comprising from 1 to 4 mg guanfacine. The tablets are suitable for once daily administration.

However, the oral administration of active agents has disadvantages, e.g., in terms of patient compliance. Furthermore, it is not possible to quickly terminate the therapy, e.g. in light of overdosing or signs of intolerance, once the prolonged release tablet has been ingested.

Therefore, a need exists for a transdermal therapeutic system for the transdermal administration of guanfacine. In particular, a need exists for a TTS, which is suitable for multi day therapy with a single application thereby improving patient compliance.

OBJECTS AND SUMMARY OF THE INVENTION

It is therefore an object of the present invention to provide a TTS for the transdermal administration of guanfacine. In particular, it is an objection of the present invention to provide a TTS for the transdermal administration of guanfacine providing a skin permeation rate which is sufficient for achieving a therapeutically effective dose.

It is a further object of the present invention to provide a TTS for the transdermal administration of guanfacine providing therapeutically effective amounts of guanfacine for at least 24 hours, preferably at least 72 hours, more preferably about 84 hours. In particular, it is an object of the present invention that the therapeutically effective amounts are provided over the whole time period, wherein the TTS is applied to the skin, allowing an around the clock treatment by exchanging the TTS after a certain application time of, e.g., at least 24 hours, preferably at least 72 hours, more preferably about 84 hours.

It is a further object of the present invention to provide a TTS for the transdermal administration of guanfacine, wherein the fluctuation in guanfacine blood plasma concentration is reduced when compared to oral administration, in particular at steady state.

It is a further object of the present invention to provide a TTS for the transdermal administration of guanfacine with a high active ingredient utilization.

It is another object of the present invention to provide a TTS for the transdermal administration of guanfacine which complies with the needs of a convenient application in view of size and thickness and/or which is easy and cost-efficient to manufacture.

These objects and others are accomplished by the present invention, which according to one aspect relates to a transdermal therapeutic system for the transdermal administration of guanfacine comprising a guanfacine-containing layer structure, said guanfacine-containing layer structure comprising:
A) a backing layer; and
B) a guanfacine-containing layer;
wherein the transdermal therapeutic system comprises at least one polymer and at least one additive selected from the group consisting of dispersing agents, permeation enhancers, and solubilizers.

It has been found that the TTS according to the present invention, which comprises at least one additive selected from the group consisting of dispersing agents, permeation enhancers, and solubilizers, provides advantageous properties in terms of the constant and continuous guanfacine delivery. In particular, the TTS according to the present invention provides suitable permeation rates and suitable permeated amounts of guanfacine over a time period of at least 24 hours, preferably at least 72 hours, more preferably about 84 hours.

According to certain embodiments, the invention also relates to a transdermal therapeutic system for the transdermal administration of guanfacine as described above, wherein the guanfacine-containing layer is a guanfacine-containing matrix layer comprising:
i) guanfacine;
ii) the at least one polymer; and
iii) the at least one additive.

In a preferred embodiment, the at least one polymer is selected from the group consisting of silicone polymers, acrylate polymers, silicone acrylic hybrid polymers, polyisobutylenes, and styrene-isoprene-styrene block copolymers, preferably from the group consisting of silicone polymers and silicone acrylic hybrid polymers.

Preferably, the at least one polymer is present in the TTS in an amount of from 20 to 99%, preferably from 30 to 97%, most preferably from 35 to 92% by weight based on the total weight of the guanfacine-containing layer.

In a preferred embodiment, the at least one additive is a dispersing agent, which is selected from the group consisting of esters of fatty acids with polyols, fatty alcohols, polyethylene glycols having a number average molecular weight of from 300 to 400, polyethylene glycol alkyl ethers, and is preferably polyethylene glycol $C_8$-$C_{20}$-alkyl ether having from 2 to 10 EO units. In another preferred embodiment, the at least one additive is a permeation enhancer, which is selected from the group consisting of diethylene glycol monoethyl ether (transcutol), oleic acid, levulinic acid, caprylic/capric triglycerides, diisopropyl adipate, isopropyl myristate, isopropyl palmitate, lauryl lactate, triacetin, dimethylpropylene urea, and oleyl alcohol, and is preferably oleyl alcohol. In another preferred embodiment, the at least one additive is a solubilizer, which is selected from the group consisting of copolymers derived from esters of acrylic and methacrylic acid, polyvinylpyrrolidone, vinylpyrrolidone-vinyl acetate copolymers, and polyvinyl caprolactam-polyvinyl acetate-polyethylene glycol graft copolymers, and is preferably a polyvinyl caprolactam-polyvinyl acetate-polyethylene glycol graft copolymer.

It is to be understood that also combinations of additives may be present in the TTS, preferably in the guanfacine-containing layer. In a preferred embodiment, at least two additives are present, e.g. a combination of a dispersing agent and a permeation enhancer, or a combination of a dispersing agent and a solubilizer, or a combination of a permeation enhancer and a solubilizer. In one preferred embodiment, at least three additives are present, e.g. a combination of a dispersing agent, a permeation enhancer, and a solubilizer.

Preferably, each additive is present in the TTS in an amount of from 0.5 to 10% by weight or from 1 to 10% by weight based on the total weight of the guanfacine-containing layer.

The additives described herein are suitable for improving the release properties of the TTS, e.g., by allowing homogeneous dispersion of the guanfacine within TTS, by enhancing skin permeation, and by stabilizing the dispersion and avoiding crystallization of guanfacine. Moreover, the solubilizer may enhance cohesion and modulate adhesiveness of the TTS. It is to be understood that one additive compound may also fulfill several functions in the TTS. For example, certain permeation enhancers may also be classified as dispersing agents. Further details in this regard are provided below.

According to one specific aspect, the present invention relates to a transdermal therapeutic system for the transdermal administration of guanfacine, comprising a guanfacine-containing layer structure, said guanfacine-containing layer structure comprising:
A) a backing layer; and
B) a guanfacine-containing layer, preferably a guanfacine-containing matrix layer, comprising;
   i) guanfacine in an amount of from 3 to 13% by weight, based on the total weight of the guanfacine-containing layer;
   ii) at least one silicone acrylic hybrid polymer in an amount of from 74 to 89% by weight, based on the total weight of the guanfacine-containing layer;
   iii) at least one dispersing agent in an amount of from 2 to 6% by weight, based on the total weight of the guanfacine-containing layer;
   iv) at least one permeation enhancer in an amount of from 2 to 6% by weight, based on the total weight of the guanfacine-containing layer; and
   v) optionally at least one solubilizer in an amount of from 0.5 to 4% by weight, based on the total weight of the guanfacine-containing layer.

According to certain embodiments of the invention, the transdermal therapeutic system according to the invention is for use in a method of treating a human patient, preferably for use in a method of treating a human patient at the age of from 6 to 17. In particular, the transdermal therapeutic system according to the invention is for use in a method of treating hypertension or attention deficit hyperactivity disorder (ADHD) and/or as adjunctive therapy to stimulant medications in a human patient, preferably in a human patient at the age of from 6 to 17. In connection with these medical uses, the TTS according to the invention is preferably applied to the skin of the patient for at least 24 hours, more preferably at least 72 hours, most preferably about 84 hours.

According to certain embodiments, the invention further relates to a method of treating a human patient, preferably a human patient at the age of from 6 to 17, by applying a transdermal therapeutic system according to the invention to the skin of the patient. In particular, the present invention relates to a method of treating hypertension or attention deficit hyperactivity disorder (ADHD) in a human patient, preferably a human patient at the age of from 6 to 17, by applying a transdermal therapeutic system according to the invention to the skin of the patient. In connection with these methods, it is preferred that the TTS according to the invention is applied to the skin of the patient for at least 24 hours, more preferably at least 72 hours, most preferably about 84 hours.

According to a further aspect, the present invention relates to a transdermal therapeutic system for the transdermal administration of guanfacine comprising a guanfacine-containing layer structure, wherein the transdermal therapeutic system provides by transdermal delivery one or more pharmacokinetic parameter(s) selected from the group consisting of
   having an $AUC_{0-24}$ of about 10 to 600 ng/mL) h,
   having an $AUC_{0-72}$ of about 30 to 1800 ng/mL) h,
   having an $AUC_{0-84}$ of about 35 to 2100 ng/mL) h,
   having a $C_{max}$ to $C_{24}$ ratio of less than 2.0,
   having a $C_{max}$ to $C_{72}$ ratio of less than 3.0, and
   having a $C_{max}$ to $C_{84}$ ratio of less than 3.5.

According to yet a further aspect, the present invention relates to a transdermal therapeutic system comprising guanfacine for use in a method of treating a human patient, preferably a human patient at the age of from 6 to 17, by transdermal administration of guanfacine, wherein the transdermal therapeutic system is applied to the skin of a patient for at least 24 hours, preferably at least 72 hours, more preferably about 84 hours.

According to yet a further aspect, the present invention relates to guanfacine for use in a method of treating a human patient, preferably a human patient at the age of from 6 to 17, by transdermal administration of guanfacine with a transdermal therapeutic system, wherein the transdermal therapeutic system is applied to the skin of a patient for at least 24 hours, preferably at least 72 hours, more preferably about 84 hours.

According to yet a further aspect, the present invention relates to a method of treating a human patient, preferably a human patient at the age of from 6 to 17, by transdermal administration of guanfacine, wherein the transdermal therapeutic system is applied to the skin of a patient for at least 24 hours, preferably at least 72 hours, more preferably about 84 hours.

According to another aspect, the present invention relates to a process for manufacturing a guanfacine-containing layer for use in a transdermal therapeutic system according to the invention comprising the steps of:
1) combining at least the components
   i) guanfacine;
   ii) at least one polymer; and
   iii) at least one additive selected from dispersing agents, permeation enhancers, and solubilizers;
   to obtain a coating composition;
2) coating the coating composition onto a backing layer or a release liner to obtain a coated coating composition; and
3) drying the coated coating composition to form the guanfacine-containing layer.

Preferably the at least one polymer is provided as a solution, wherein the solvent comprises ethyl acetate or n-heptane.

According to yet another aspect, the present invention relates to a transdermal therapeutic system obtainable by the process according to the invention.

Definitions

Within the meaning of this invention, the term "transdermal therapeutic system" (TTS) refers to a system by which the active agent (e.g. guanfacine) is administered to the systemic circulation via transdermal delivery and refers to the entire individual dosing unit that is applied, after removing an optionally present release liner, to the skin of a patient, and which comprises a therapeutically effective amount of active agent in an active agent-containing layer structure and optionally an additional adhesive overlay on top of the active agent-containing layer structure. The active agent-containing layer structure may be located on a release liner (a detachable protective layer), thus, the TTS may further comprise a release liner. Within the meaning of this invention, the term "TTS" in particular refers to systems providing transdermal delivery, excluding active delivery for example via iontophoresis or microporation. Transdermal therapeutic systems may also be referred to as transdermal drug delivery systems (TDDS) or transdermal delivery systems (TDS).

Within the meaning of this invention, the term "guanfacine-containing layer structure" refers to the layer structure containing a therapeutically effective amount of guanfacine and comprising a backing layer and at least one guanfacine-containing layer. Preferably, the guanfacine-containing layer structure is a guanfacine-containing self-adhesive layer structure.

Within the meaning of this invention, the term "therapeutically effective amount" refers to a quantity of active agent in the TTS which is, if administered by the TTS to a patient, sufficient to treat, prevent or reduce hypertension or attention deficit hyperactivity disorder (ADHD) or which is sufficient for adjunctive therapy to stimulant medications in a human patient. A TTS usually contains more active in the system than is in fact provided to the skin and the systemic circulation. This excess amount of active agent is usually necessary to provide enough driving force for the delivery from the TTS to the systemic circulation.

Within the meaning of this invention, the terms "active", "active agent", and the like, as well as the term "guanfacine" refer to guanfacine in any pharmaceutically acceptable chemical and morphological form and physical state. These forms include without limitation guanfacine in its free base form, protonated or partially protonated guanfacine, guanfacine salts, and in particular acid addition salts formed by addition of an inorganic or organic acid such as guanfacine hydrochloride or guanfacine tartrate, solvates, hydrates, clathrates, cocrystals, complexes and so on, as well as guanfacine in the form of particles which may be micronized, crystalline and/or amorphous, and any mixtures of the aforementioned forms. The guanfacine, where contained in a medium such as a solvent, is preferably present in dispersed form.

When guanfacine is mentioned to be used in a particular form in the manufacture of the TTS, this does not exclude interactions between this form of guanfacine and other ingredients of the guanfacine-containing layer structure, e.g. salt formation or complexation, in the final TTS. This means that, even if guanfacine is included in its free base form, it may be present in the final TTS in protonated or partially protonated form or in the form of an acid addition salt, or, if it is included in the form of a salt, parts of it may be present as free base in the final TTS. Unless otherwise indicated, in particular the amount of guanfacine in the layer structure relates to the amount of guanfacine included in the TTS during manufacture of the TTS and is calculated based on guanfacine in the form of the free base. E.g., when a) 0.1 mmol (equal to 24.61 mg) guanfacine base or b) 0.1 mmol (equal to 27.71 mg) guanfacine hydrochloride is included in the TTS during manufacture, the amount of guanfacine in the layer structure is, within the meaning of the invention, in both cases 24.06 mg, i.e. 0.1 mmol.

The guanfacine starting material included in the TTS during manufacture of the TTS may be in the form of particles. Guanfacine may e.g. be present in the active agent-containing layer structure in the form of particles, which are preferably homogeneously dispersed within the active agent-containing layer structure.

Within the meaning of this invention, the term "particles" refers to a solid, particulate material comprising individual particles, the dimensions of which are negligible compared to the material. In particular, the particles are solid, including plastic/deformable solids, including amorphous and crystalline materials.

Within the meaning of this invention, the term "dispersing" refers to a step or a combination of steps wherein a starting material (e.g. guanfacine) is not dissolved or not completely dissolved. Dispersing in the sense of the invention comprises the dissolution of apart of the starting material (e.g. guanfacine particles), depending on the solubility of the starting material (e.g. the solubility of guanfacine in the coating composition).

There are two main types of TTS for active agent delivery, i.e. matrix-type TTS and reservoir-type TTS. The release of the active agent in a matrix-type TTS is mainly controlled by the matrix including the active agent itself. In contrast thereto, a reservoir-type TTS typically needs a rate-controlling membrane controlling the release of the active agent. In principle, also a matrix-type TTS may contain a rate-controlling membrane. However, matrix-type TTS are advantageous in that, compared to reservoir-type TTS, usually no rate determining membranes are necessary and no dose dumping can occur due to membrane rupture. In summary, matrix-type transdermal therapeutic systems (TTS) are less complex in manufacture and easy and convenient to use by patients.

Within the meaning of this invention, "matrix-type TTS" refers to a system or structure wherein the active is homogeneously dissolved and/or dispersed within a polymeric carrier, i.e. the matrix, which forms with the active agent and optionally remaining ingredients a matrix layer. In such a system, the matrix layer controls the release of the active agent from the TTS. Preferably, the matrix layer has sufficient cohesion to be self-supporting so that no sealing between other layers is required. Accordingly, the active agent-containing layer may in one embodiment of the invention be an active agent-containing matrix layer, wherein the active agent is homogeneously distributed within a polymer matrix. In certain embodiments, the active agent-containing matrix layer may comprise two active agent-containing matrix layers, which may be laminated together. Matrix-type TTS may in particular be in the form of a "drug-in-adhesive"-type TTS referring to a system wherein the active is homogeneously dissolved and/or dispersed within a pressure-sensitive adhesive matrix. In this connection, the active agent-containing matrix layer may also be referred to as active agent-containing pressure sensitive adhesive layer or active agent-containing pressure sensitive adhesive matrix layer. A TTS comprising the active agent dissolved and/or dispersed within a polymeric gel, e.g. a hydrogel, is also considered to be of matrix-type in accordance with present invention.

TTS with a liquid active agent-containing reservoir are referred to by the term "reservoir-type TTS". In such a system, the release of the active agent is preferably controlled by a rate-controlling membrane. In particular, the reservoir is sealed between the backing layer and the rate-controlling membrane. Accordingly, the active agent-containing layer may in one embodiment be an active agent-containing reservoir layer, which preferably comprises a liquid reservoir comprising the active agent. Furthermore, the reservoir-type TTS typically additionally comprises a skin contact layer, wherein the reservoir layer and the skin contact layer may be separated by the rate-controlling membrane. In the reservoir layer, the active agent is preferably dissolved in a solvent such as ethanol or water or in silicone oil. The skin contact layer typically has adhesive properties.

Reservoir-type TTS are not to be understood as being of matrix-type within the meaning of the invention. However, microreservoir TTS (biphasic systems having deposits (e.g. spheres, droplets) of an inner active-containing phase dispersed in an outer polymer phase), considered in the art to be a mixed form of a matrix-type TTS and a reservoir-type TTS that differ from a homogeneous single phase matrix-type TTS and a reservoir-type TTS in the concept of drug transport and drug delivery, are considered to be of matrix-type within the meaning of the invention. The sizes of microreservoir droplets can be determined by an optical microscopic measurement (for example by Leica MZ16 including a camera, for example Leica DSC320) by taking pictures of the microreservoirs at different positions at an enhancement factor between 10 and 400 times, depending on the required limit of detection. By using imaging analysis software, the sizes of the microreservoirs can be determined.

Within the meaning of this invention, the term "active agent-containing layer" refers to a layer containing the active agent and providing the area of release. The term covers active agent-containing matrix layers and active agent-containing reservoir layers. If the active agent-containing layer is an active agent-containing matrix layer, said layer is present in a matrix-type TTS. If the polymer is a pressure-sensitive adhesive, the matrix layer may also represent the adhesive layer of the TTS, so that no additional skin contact layer is present. Alternatively, an additional skin contact layer may be present as adhesive layer, and/or an adhesive overlay is provided. The additional skin contact layer is typically manufactured such that it is active agent-free. However, due to the concentration gradient, the active agent will migrate from the matrix layer to the additional skin contact layer over time, until an equilibrium is reached. The additional skin contact layer may be present on the active agent-containing matrix layer or separated from the active agent-containing matrix layer by a membrane, preferably a rate controlling membrane. Preferably, the active agent-containing matrix layer has sufficient adhesive properties, so that no additional skin contact layer is present. If the active agent-containing layer is an active agent-containing reservoir layer, said layer is present in a reservoir-type TTS, and the layer comprises the active agent in a liquid reservoir. In addition, an additional skin contact layer is preferably present, in order to provide adhesive properties. Preferably, a rate-controlling membrane separates the reservoir layer from the additional skin contact layer. The additional skin contact layer can be manufactured such that it is active agent-free or active agent-containing. If the additional skin contact layer is free of active agent the active agent will migrate, due to the concentration gradient, from the reservoir layer to the skin contact layer over time, until an equilibrium is reached. Additionally an adhesive overlay may be provided.

As used herein, the active agent-containing layer is preferably an active agent-containing matrix layer, and it is referred to the final solidified layer. Preferably, an active agent-containing matrix layer is obtained after coating and drying the solvent-containing coating composition as described herein. Alternatively an active-agent containing matrix layer is obtained after melt-coating and cooling. The active agent-containing matrix layer may also be manufactured by laminating two or more such solidified layers (e.g. dried or cooled layers) of the same composition to provide the desired area weight. The matrix layer may be self-adhesive (in the form of a pressure sensitive adhesive matrix layer), or the TTS may comprise an additional skin contact layer of a pressure sensitive adhesive for providing sufficient tack. Preferably, the matrix layer is a pressure sensitive adhesive matrix layer. Optionally, an adhesive overlay may be present.

Within the meaning of this invention, the term "pressure-sensitive adhesive" (also abbreviated as "PSA") refers to a material that in particular adheres with finger pressure, is permanently tacky, exerts a strong holding force and should be removable from smooth surfaces without leaving a residue. A pressure sensitive adhesive layer, when in contact with the skin, is "self-adhesive", i.e. provides adhesion to the skin so that typically no further aid for fixation on the skin is needed. A "self-adhesive" layer structure includes a pressure sensitive adhesive layer for skin contact which may be provided in the form of a pressure sensitive adhesive matrix layer or in the form of an additional layer, i.e. a pressure sensitive adhesive skin contact layer. An adhesive overlay may still be employed to advance adhesion. The pressure-sensitive adhesive properties of a pressure-sensitive adhesive depend on the polymer or polymer composition used.

Within the meaning of this invention, the term "silicone acrylic hybrid polymer" refers to a polymerization product including repeating units of a silicone sub-species and an acrylate-sub species. The silicone acrylic hybrid polymer thus comprises a silicone phase and an acrylic phase. Preferably, the silicone acrylic hybrid polymer comprises a silicone phase and an acrylate phase, i.e. silicone sub-species and acrylate sub-species, in a certain weight ratio, e.g. from 60:40 to 40:60. The term "silicone acrylic hybrid" is intended to denote more than a simple blend of a silicone-based sub-species and an acrylate-based sub-species. Instead, the term denotes a polymerized hybrid species that includes silicone-based sub-species and acrylate-based sub-species that have been polymerized together. The silicone acrylic hybrid polymer may also be referred to as a "silicone acrylate hybrid polymer" as the terms acrylate and acrylic are generally used interchangeably in the context of the hybrid polymers used in the present invention.

Within the meaning of this invention, the term "silicone acrylic hybrid pressure-sensitive adhesive" refers to a silicone acrylic hybrid polymer in the form of a pressure-sensitive adhesive. Silicone acrylic hybrid pressure-sensitive adhesives are described, for example, in EP 2 599 847 and WO2016/130408. Examples of silicone acrylic hybrid pressure-sensitive adhesives include the PSA series 7-6100 and 7-6300 manufactured and supplied in n-heptane or ethyl acetate by Dow Corning (7-610X and 7-630X; X=1 n-heptane-based/X=2 ethyl acetate-based). It was found that, depending on the solvent in which the silicone acrylic hybrid PSA is supplied, the arrangement of the silicone phase and the acrylic phase providing a silicone or acrylic continuous external phase and a corresponding discontinuous internal phase is different. If the silicone acrylic hybrid PSA is supplied in n-heptane, the composition contains a continuous, silicone external phase and a discontinuous, acrylic internal phase. If the silicone acrylic hybrid PSA composition is supplied in ethyl acetate, the composition contains a continuous, acrylic external phase and a discontinuous, silicone internal phase.

Within the meaning of this invention, the term "non-hybrid polymer" is used synonymously for a polymer which does not include a hybrid species. Preferably, the non-hybrid polymer is a pressure-sensitive adhesive (e.g. a silicone- or acrylate-based pressure-sensitive adhesives).

Within the meaning of this invention, the term "silicon-containing pressure-sensitive adhesive composition comprising acrylate or methacrylate functionality" comprises the condensation reaction product of a silicone resin, a silicone polymer, and a silicon-containing capping agent which provides said acrylate or methacrylate functionality. It is to be understood that the silicon-containing pressure-sensitive adhesive composition comprising acrylate or methacrylate functionality can include only acrylate functionality, only methacrylate functionality, or both acrylate functionality and methacrylate functionality.

As used herein, an active agent-containing matrix layer is a layer containing the active agent dissolved or dispersed in at least one polymer, or containing the active agent dissolved in a solvent to form an active agent-solvent mixture that is dispersed in the form of deposits (in particular droplets) in at least one polymer. Preferably, the at least one polymer is a polymer-based pressure-sensitive adhesive (e.g. a silicone acrylic hybrid pressure-sensitive adhesive). Within the meaning of this invention, the term "pressure-sensitive adhesive layer" refers to a pressure-sensitive adhesive layer obtained from a solvent-containing adhesive coating composition after coating on a film and evaporating the solvents.

Within the meaning of this invention, the term "skin contact layer" refers to the layer included in the active agent-containing layer structure to be in direct contact with the skin of the patient during administration. This may be the active agent-containing layer. When the TTS comprises an additional skin contact layer, the other layers of the active agent-containing layer structure do not contact the skin and do not necessarily have self-adhesive properties. As outlined above, an additional skin contact layer attached to the active agent-containing layer may over time absorb parts of the active agent. An additional skin contact layer may be used to enhance adherence. The sizes of an additional skin contact layer and the active agent-containing layer are usually coextensive and correspond to the area of release. However, the area of the additional skin contact layer may also be greater than the area of the active agent-containing layer. In such a case, the area of release still refers to the area of the active agent-containing layer.

Within the meaning of this invention, the term "area weight" refers to the dry weight of a specific layer, e.g. of the matrix layer, provided in g/m². The area weight values are subject to a tolerance of ±10%, preferably 7.5%, due to manufacturing variability.

If not indicated otherwise "%" refers to weight-% (% by weight).

Within the meaning of this invention, the term "polymer" refers to any substance consisting of so-called repeating units obtained by polymerizing one or more monomers, and includes homopolymers which consist of one type of monomer and copolymers which consist of two or more types of monomers. Polymers may be of any architecture such as linear polymers, star polymer, comb polymers, brush polymers, of any monomer arrangements in case of copolymers, e.g. alternating, statistical, block copolymers, or graft polymers. The minimum molecular weight varies depending on the polymer type and is known to the skilled person. Polymers may e.g. have a molecular weight above 2000, preferably above 5000 and more preferably above 10,000 Dalton. Correspondingly, compounds with a molecular weight below 2000, preferably below 5000 or more preferably below 10,000 Dalton are usually referred to as oligomers.

Within the meaning of this invention, the term "cross-linking agent" refers to a substance which is able to cross-link functional groups contained within the polymer.

Within the meaning of this invention, the term "adhesive overlay" refers to a self-adhesive layer structure that is free of active agent and larger in area than the active agent-containing structure and provides additional area adhering to the skin, but no area of release of the active agent. It enhances thereby the overall adhesive properties of the TTS. The adhesive overlay comprises a backing layer that may provide occlusive or non-occlusive properties and an adhesive layer. Preferably, the backing layer of the adhesive overlay provides non-occlusive properties.

Within the meaning of this invention, the term "backing layer" refers to a layer which supports the active agent-containing layer or forms the backing of the adhesive overlay. At least one backing layer in the TTS and usually the backing layer of the active agent-containing layer is substantially impermeable to the active agent contained in the layer during the period of storage and administration and thus prevents active loss or cross-contamination in accordance with regulatory requirements. Preferably, the backing layer is also occlusive, meaning substantially impermeable to water and water-vapor. Suitable materials for a backing layer include polyethylene terephthalate (PET), polyethylene (PE), ethylene vinyl acetate-copolymer (EVA), polyurethanes, and mixtures thereof. Suitable backing layers are thus for example PET laminates, EVA-PET laminates and PE-PET laminates. In a preferred embodiment, the backing layer is a siliconized PET foil. Also suitable are woven or non-woven backing materials.

The TTS according to the present invention can be characterized by certain parameters as measured in an in vitro skin permeation test.

In general, the in vitro permeation test is performed in a Franz diffusion cell, with EVA membrane (e.g. 9% vinyl acetate and 50 µm thickness, preferably provided by 3M), and with phosphate buffer pH 5.5 or 7.4 as receptor medium (32° C. with 0.1% saline azide).

Further, in vitro permeation test may be performed in a Franz diffusion cell, with human or animal skin and preferably with dermatomed split-thickness human skin with a thickness of 800 µm and an intact epidermis, and with phosphate buffer pH 5.5 or 7.4 as receptor medium (32° C. with 0.1% saline azide) with or without addition of a maximum of 40 vol-% organic solvent e.g. ethanol, acetonitrile, isopropanol, dipropylenglycol, PEG 400 so that a receptor medium may e.g. contain 60 vol-% phosphate buffer pH5.5, 30 vol-% dipropylenglycol and 10 vol-% acetonitrile.

Where not otherwise indicated, the in vitro permeation test is performed with dermatomed split-thickness human skin with a thickness of 800 µm and an intact epidermis, and with phosphate buffer pH5.5 as receptor medium (32° C. with 0.1% saline azide). The amount of active permeated into the receptor medium is determined in regular intervals using a validated HPLC method with a UV photometric detector by taking a sample volume. The receptor medium is completely or in part replaced by fresh medium when taking the sample volume, and the measured amount of active permeated relates to the amount permeated between the two last sampling points and not the total amount permeated so far.

Thus, within the meaning of this invention, the parameter "permeated amount" is provided in µg/cm² and relates to the amount of active permeated in a sample interval at certain elapsed time. E.g., in an in vitro permeation test as described above, wherein the amount of active permeated into the receptor medium has been e.g. measured at hours 0, 2, 4, 8, 12 and 24, the "permeated amount" of active can be given e.g. for the sample interval from hour 8 to hour 12 and corresponds to the measurement at hour 12, wherein the receptor medium has been exchanged completely at hour 8.

The permeated amount can also be given as a "cumulative permeated amount", corresponding to the cumulated amount of active permeated at a certain point in time. E.g., in an in vitro permeation test as described above, wherein the amount of active permeated into the receptor medium has been e.g. measured at hours 0, 2, 4, 8, 12 and 24, the "cumulative permeated amount" of active at hour 12 corresponds to the sum of the permeated amounts from hour 0 to hour 2, hour 2 to hour 4, hour 4 to hour 8 and hour 8 to hour 12.

Within the meaning of this invention, the parameter "skin permeation rate" for a certain sample interval at certain elapsed time is provided in µg/(cm²*h) and is calculated from the permeated amount in said sample interval as measured by in vitro permeation test as described above in µg/cm², divided by the hours of said sample interval. E.g. the skin permeation rate in an in vitro permeation test as described above, wherein the amount of active permeated into the receptor medium has been e.g. measured at hours 0, 2, 4, 8, 12 and 24, the "skin permeation rate" at hour 12 is calculated as the permeated amount in the sample interval from hour 8 to hour 12 divided by 4 hours.

A "cumulative skin permeation rate" can be calculated from the respective cumulative permeated amount by dividing the cumulative permeated amount by the elapsed time. E.g. in an in vitro permeation test as described above, wherein the amount of active permeated into the receptor medium has been e.g. measured at hours 0, 2, 4, 8, 12 and 24, the "cumulative skin permeation rate" at hour 12 is calculated as the cumulative permeated amount for hour 12 (see above) divided by 12 hours.

Within the meaning of this invention, the above parameters "permeated amount" and "skin permeation rate" (as well as "cumulative permeated amount" and "cumulative skin permeation rate") refer to mean values calculated from at least 3 in vitro permeation test experiments. Where not otherwise indicated, the standard deviation (SD) of these mean values refer to a corrected sample standard deviation, calculated using the formula:

$$SD = \sqrt{\frac{1}{n-1}\sum_{i=1}^{n}(x_i - \bar{x})^2}$$

wherein n is the sample size, $\{x_1, x_2, \ldots x_n\}$ are the observed values and x is the mean value of the observed values.

The TTS according to the present invention can also be characterized by certain parameters as measured in an in vivo clinical study.

Within the meaning of this invention, the parameter "mean release rate" refers to the mean release rate in µg/h (µg/hour, µg/hr) or in mg/day over the period of administration (e.g., 1 to 7 days) by which the active agent is released through the human skin into the systemic circulation and is based on the AUC obtained over said period of administration in a clinical study.

Within the meaning of this invention, the term "extended period of time" relates to a period of at least or about 24 h, at least or about 48 h, at least or about 72 h, at least or about 84 h, at least or about day, at least or about 2 days, or at least or about 3 days, or at least or about 3.5 days, or to a period of about 24 h to about 168 h or 1 to 7 day(s), or about 24 h to about 84 h or 1 to 3.5 day(s).

For a continuous drug treatment, the frequency of drug administration is preferably kept sufficiently high so as to maintain therapeutically effective blood plasma concentration. In other words, the interval between two dosage form administrations, also called dosing interval, needs to be adapted accordingly. Within the meaning of the present invention, the term "dosing interval" refers to the period of time between two consecutive TTS administrations, i.e. the interval between two consecutive points in time a TTS is applied to the skin of the patient. Once applied, the TTS is usually maintained on the skin of the patient for the entire dosing interval and only removed at the end of the dosing interval, at which time a new TTS is applied to the skin. E.g., if the dosing interval is 24 hours or 1 day, the TTS is applied to and maintained on the skin of the patient for 24 hours or 1 day. After 24 hours or 1 day, the TTS is removed from the skin and a new TTS is applied. Thus, a dosing interval of 24 hours or 1 day allows a daily TTS exchange mode in an around-the-clock treatment. Preferred according to the invention is a dosing interval of at least 72 hours, preferably about 84 hours. It is to be understood that the application time of the TTS to the skin of the patient is preferably identical to the time of the dosing interval, which means that constant administration of guanfacine takes place with exchanging TTS.

Within the meaning of this invention, the term "room temperature" refers to the unmodified temperature found indoors in the laboratory where the experiments are conducted and usually lies within 15 to 35° C., preferably about 18 to 25° C.

Within the meaning of this invention, the term "patient" refers to a subject who has presented a clinical manifestation of a articular symptom or symptoms suggesting the need for treatment, who is treated preventatively or prophylactically for a condition, or who has been diagnosed with a condition to be treated. Preferably, the patient is 6 to 17 years old.

Within the meaning of this invention the term "pharmacokinetic parameters" refers to parameters describing the blood plasma curve, e.g. $C_{max}$, $C_t$ and $AUC_{t1-t2}$ obtained in a clinical study, e.g. by single-dose, multi-dose or steady state administration of the active agent-containing TTS, e.g. the guanfacine-containing TTS to healthy human subjects. The pharmacokinetic parameters of the individual subjects are summarized using arithmetic and geometric means, e.g. a mean $C_{max}$, a mean AUCt and a mean AUCINF, and additional statistics such as the respective standard deviations and standard errors, the minimum value, the maximum value, and the middle value when the list of values is ranked (Median). In the context of the present invention, pharmacokinetic parameters, e.g. the $C_{max}$, $C_t$ and $AUC_{t1-t2}$ refer to geometric mean values if not indicated otherwise. It cannot be precluded that the absolute mean values obtained for a certain TTS in a clinical study vary to a certain extent from study to study. To allow a comparison of absolute mean values between studies, a reference formulation, e.g. in the future any product based on the invention, may be used as internal standard. A comparison of the AUC per area of release of the respective reference product in the earlier and later study can be used to obtain a correction factor to take into account differences from study to study.

Clinical studies according to the present invention refer to studies performed in full compliance with the International Conference for Harmonization of Clinical Trials (ICH) and all applicable local Good Clinical Practices (GCP) and regulations.

Within the meaning of this invention, the term "healthy human subject" refers to a male or female subject with a body weight ranging from 55 kg to 100 kg and a body mass index (BMI) ranging from 18 to 29.4 and normal physiological parameters, such as blood pressure, etc. Healthy human subjects for the purposes of the present invention are selected according to inclusion and exclusion criteria which are based on and in accordance with recommendations of the ICH.

Within the meaning of this invention, the term "subject population" refers to at least five, preferably at least ten individual healthy human subjects.

Within the meaning of this invention, the term "geometric mean" refers to the mean of the log transformed data back-transformed to the original scale.

Within the meaning of this invention, the term "arithmetic mean" refers to the sum of all values of observation divided by the total number of observations.

Within the meaning of this invention, the parameter "AUC" corresponds to the area under the plasma concentration-time curve. The AUC value is proportional to the amount of active agent absorbed into the blood circulation in total and is hence a measure for the bioavailability.

Within the meaning of this invention, the parameter "$AUC_{t1-t2}$" is provided in (ng/ml) hand relates to the area under the plasma concentration-time curve from hour t1 to t2 and is calculated by the linear trapezoidal method, unless otherwise indicated. Other calculation methods are e.g. the logarithmic and linear log trapezoidal method.

Within the meaning of this invention, the parameter "$C_{max}$" is provided in (ng/ml) and relates to the maximum observed blood plasma concentration of the active agent.

Within the meaning of this invention, the parameter "$C_t$" is provided in (ng/ml) and relates to the blood plasma concentration of the active agent observed at hour t.

Within the meaning of this invention, the parameter "$t_{max}$" is provided in h and relates to the time point at which the $C_{max}$ value is reached. In other words, $t_{max}$ is the time point of the maximum observed plasma concentration.

Within the meaning of this invention, the term "mean plasma concentration" is provided in (ng/ml) and is a mean of the individual plasma concentrations of active agent, e.g. guanfacine, at each point in time.

Within the meaning of this invention, the term "coating composition" refers to a composition comprising all components of the matrix layer in a solvent, which may be coated onto the backing layer or release liner to form the matrix layer upon drying.

Within the meaning of this invention, the term "pressure sensitive adhesive composition" refers to a pressure sensitive adhesive at least in mixture with a solvent (e.g. n-heptane or ethyl acetate).

Within the meaning of this invention, the term "dissolve" refers to the process of obtaining a solution, which is clear and does not contain any particles, as visible to the naked eye.

Within the meaning of this invention, the term "solvent" refers to any liquid substance, which preferably is a volatile organic liquid such as methanol, ethanol, isopropanol, acetone, ethyl acetate, methylene chloride, hexane, n-heptane, toluene and mixtures thereof.

BRIEF DESCRIPTION OF THE DRAWINGS

FIG. 6 depicts the guanfacine permeated amount of TTS prepared according to Example 6a.

DETAILED DESCRIPTION

TTS Structure

Figure 1:
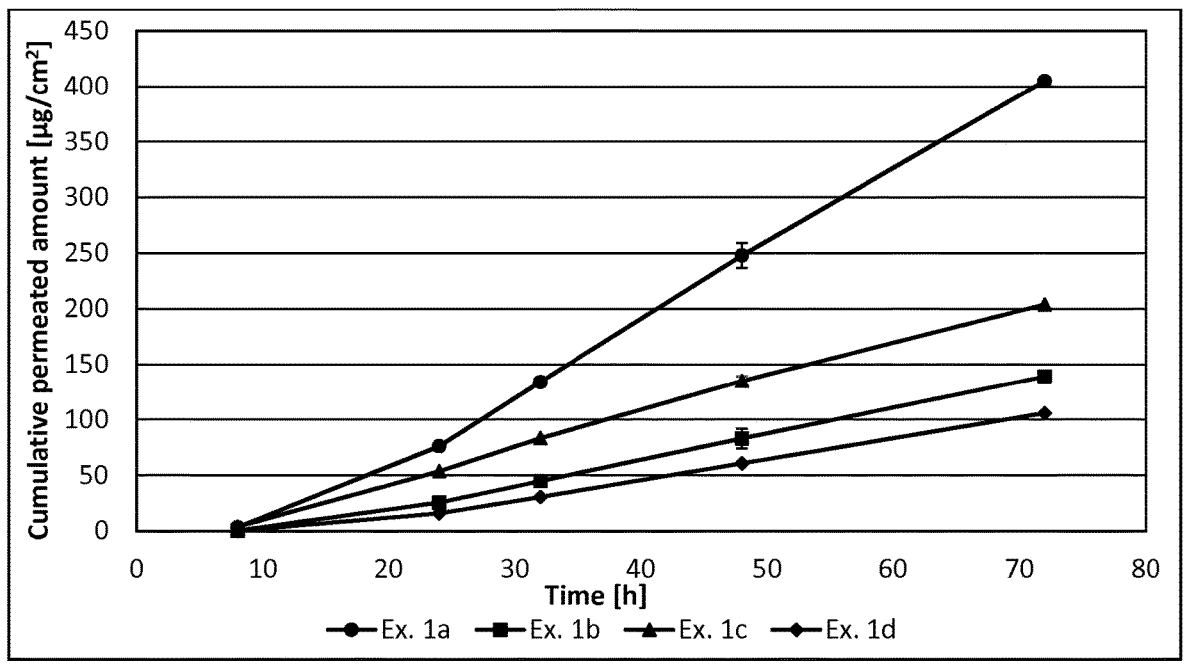
FIG. 1 depicts the guanfacine permeated amount of TTS prepared according to Examples 1a-d.

The present invention relates to a transdermal therapeutic system for the transdermal administration of guanfacine comprising a guanfacine-containing layer structure, said guanfacine-containing layer structure comprising a) a backing layer, and b) a guanfacine-containing layer, wherein the transdermal therapeutic system comprises at least one polymer and at least one additive selected from the group consisting of dispersing agents, permeation enhancers, and solubilizers. The guanfacine-containing layer structure is preferably a guanfacine-containing self-adhesive layer structure and preferably does not comprise an additional skin contact layer. In particular, the at least one polymer, which is present in the transdermal therapeutic system, and is preferably present in the self-adhesive layer structure, preferably provides the adhesive properties.

The TTS according to the present invention may be a matrix-type TTS or a reservoir-type TTS, and preferably is a matrix-type TTS.

In a matrix-type TTS according to the invention, the guanfacine is preferably homogeneously dispersed within a polymeric carrier, i.e. the matrix, which forms with the guanfacine and optionally remaining ingredients a matrix layer. Accordingly, the guanfacine-containing layer may in one embodiment of the invention be a guanfacine-containing matrix layer, wherein the guanfacine is homogeneously dispersed within a polymer matrix. The polymer matrix comprises the at least one polymer as defined herein. Thus, it is preferred according to the invention that the guanfacine-containing matrix layer comprises guanfacine and the at least one polymer, which is present in the TTS. Furthermore, the guanfacine-containing matrix layer preferably comprises the at least one additive as defined herein, which is present in the TTS. It is preferred that the guanfacine-containing matrix layer is self-adhesive, so that no additional skin contact layer is present. Thus, the at least one polymer is preferably a pressure sensitive adhesive polymer. If a guanfacine-containing matrix layer is prepared by laminating together two guanfacine-containing matrix layers, which are of substantially the same composition, the resulting double layer is to be regarded as one guanfacine-containing matrix layer.

In a reservoir-type TTS according to the present invention, the guanfacine-containing layer is a guanfacine-containing reservoir layer, which preferably comprises a liquid reservoir comprising the guanfacine. The reservoir-type TTS typically additionally comprises a skin contact layer, wherein the reservoir layer and the skin contact layer are preferably separated by the rate-controlling membrane. The at least one polymer as defined herein then provides the adhesive properties. Preferably, the skin contact layer is manufactured such that it is guanfacine-free.

In a preferred embodiment of the invention, the guanfacine-containing layer is a guanfacine-containing matrix layer comprising
  i) guanfacine;
  ii) the at least one polymer; and
  iii) the at least one additive, which is selected from the group consisting of dispersing agents, permeation enhancers, and solubilizers.

Thus, according to one embodiment, the present invention relates to a transdermal therapeutic system for the transdermal administration of guanfacine comprises a guanfacine-containing layer structure comprising:
  A) a backing layer; and
  B) a guanfacine-containing layer, which is preferably a guanfacine-containing matrix layer, comprising:
    i) guanfacine;
    ii) at least one polymer; and
    iii) at least one additive, which is selected from the group consisting of dispersing agents, permeation enhancers, and solubilizers.

The guanfacine-containing layer structure is preferably a guanfacine-containing self-adhesive layer structure. In this connection, it is also preferred that the guanfacine-containing layer structure does not comprise an additional skin contact layer. Instead, it is preferred that the guanfacine-containing layer, which is preferably a guanfacine-containing matrix layer, is self-adhesive. Thus, in a preferred embodiment, the guanfacine-containing layer structure is a guanfacine-containing self-adhesive layer structure and preferably does not comprise an additional skin contact layer. Alternatively or additionally, it is preferred that the guanfacine-containing layer is directly attached to the backing layer, so that there is no additional layer between the backing layer and the guanfacine-containing layer. Consequently, a layer structure of low complexity is obtained, which is advantageous, e.g., in terms of the costs for the manufacture.

In particular, it is preferred that the guanfacine-containing layer structure comprises not more than 3, preferably 2 layers, i.e. preferably only the backing layer and the guanfacine-containing layer. Sufficient adhesion between the guanfacine-containing self-adhesive layer structure and the skin of the patient during administration is then provided by the guanfacine-containing layer, which is preferably a guanfacine-containing matrix layer. If an additional skin contact layer is present, e.g., as the third layer of the guanfacine-containing layer structure, the adhesive properties may be provided by the additional skin contact layer. However, it is preferred according to the invention that no additional skin contact layer is present.

The self-adhesive properties of the guanfacine-containing layer structure are preferably provided by the at least one polymer, which is present in the TTS, preferably in the guanfacine-containing layer, more preferably in the guanfacine-containing matrix layer. Thus, in a preferred embodiment of the invention, the at least one polymer is a pressure sensitive adhesive polymer.

In a preferred embodiment, the at least one polymer is selected from the group consisting of silicone polymers (also referred to as silicones), acrylate polymers (also referred to as acrylates), silicone acrylic hybrid polymers, polyisobutylenes, and styrene-isoprene-styrene block copolymers. In a particularly preferred embodiment, the at least one polymer is selected from the group consisting of silicone polymers and silicone acrylic hybrid polymers. Further details regarding the specific polymers are provided further below.

It is to be understood that the TTS, preferably the guanfacine-containing layer, more preferably the guanfacine-containing matrix layer may also comprise at least two polymers, wherein the at least two polymers are selected from the group consisting of silicone polymers, acrylate polymers, silicone acrylic hybrid polymers, polyisobutylenes, and styrene-isoprene-styrene block copolymers. In a preferred embodiment, the TTS, preferably the guanfacine-containing layer, more preferably the guanfacine-containing matrix layer, comprises a first polymer selected from silicone polymers and silicone acrylic hybrid polymers, and optionally a second polymer selected from acrylate polymers, silicone acrylic hybrid polymers, and silicone polymers. The first polymer provides advantages in terms of a high flux, while the second polymer can be used to reduce and/or optimize the flux in order to obtain a continuous and constant flux. Furthermore, the tackiness of the TTS can be modified by using a combination of at least two polymers. Further details regarding the specific polymers are provided below.

It is to be understood that the TTS according to the invention contains at least a therapeutically effective amount of guanfacine. Thus, in a preferred embodiment of the invention, the guanfacine-containing layer structure contains a therapeutically effective amount of guanfacine. The guanfacine in the guanfacine-containing layer structure is preferably present in the form of the free base, which is preferably dispersed in the guanfacine-containing layer. Preferred embodiments regarding the guanfacine in the TTS according to the invention are provided further below.

In order to improve the dispersibility of the guanfacine, the permeation properties of the guanfacine-containing TTS and the stability of the guanfacine within the TTS, the TTS comprises at least one additive selected from the group consisting of dispersing agents, permeation enhancers, and solubilizers. The additives are described in further detail below.

It is to be understood that the additive is present within the TTS, preferably within the guanfacine-containing layer structure, and more preferably within the guanfacine-containing layer, in particular within the guanfacine-containing matrix layer.

It is preferred according to the invention that the area of release of the TTS ranges from 1 to 100 cm$^2$, preferably from 2.5 to 50 cm$^2$.

In a preferred embodiment of the invention, the backing layer is substantially guanfacine impermeable. Furthermore, it is preferred that the backing layer is occlusive as outlined above.

According to certain embodiments of the invention, the TTS may further comprise an adhesive overlay. This adhesive overlay is in particular larger in area than the guanfacine-containing layer structure and is attached thereto for enhancing the adhesive properties of the overall transdermal therapeutic system. Said adhesive overlay comprises a backing layer and an adhesive layer. The adhesive overlay provides additional area adhering to the skin but does not add to the area of release of the guanfacine. The adhesive overlay comprises a self-adhesive polymer or a self-adhesive polymer mixture selected from the group consisting of silicone acrylic hybrid polymers, acrylate polymers, silicone polymers, polyisobutylenes, styrene-isoprene-styrene copolymers, and mixtures thereof, which may be identical to or different from any polymer or polymer mixture included in the guanfacine-containing layer structure.

The guanfacine-containing layer structure according to the invention, such as a guanfacine-containing self-adhesive layer structure, is normally located on a detachable protective layer (release liner), from which it is removed immediately before application to the surface of the patient's skin. Thus, the TTS may further comprise a release liner. A TTS protected this way is usually stored in a blister pack or a seam-sealed pouch. The packaging may be child resistant and/or senior friendly.

Guanfacine-Containing Layer

As outlined in more detail above, the TTS according to the present invention comprises a guanfacine-containing layer structure comprising a guanfacine-containing layer. Preferably, the guanfacine-containing layer structure is a guanfacine-containing self-adhesive layer structure. Accordingly, it is also preferred that the guanfacine-containing layer is a self-adhesive guanfacine-containing layer, more preferably a self-adhesive guanfacine-containing matrix layer. In a preferred embodiment, the guanfacine-containing layer comprises a therapeutically effective amount of the guanfacine.

In one embodiment of the invention, the guanfacine-containing layer is a guanfacine-containing matrix layer. In another embodiment, the guanfacine-containing layer is a guanfacine-containing reservoir layer. It is preferred that the guanfacine-containing layer is a guanfacine-containing matrix layer.

In one embodiment, the guanfacine-containing layer comprises
i) guanfacine, preferably in the form of the free base; and
ii) the at least one polymer; and
iii) the at least one additive, which is selected from the group consisting of dispersing agents, permeation enhancers, and solubilizers.

As explained above, the at least one polymer is preferably selected from the group consisting of silicone polymers, acrylate polymers, silicone acrylic hybrid polymers, polyisobutylenes, and styrene-isoprene-styrene block copolymers. In connection with the at least one additive, it is preferred that at least two additives, e.g. the combination of a dispersing agent and a permeation enhancer, or the combination of a dispersing agent and a solubilizer, or the combination of a permeation enhancer and a solubilizer, particularly preferably at least three additives additives, in particular the combination of a dispersing agent, a permeation enhancer and a solubilizer are present.

In a preferred embodiment, the guanfacine-containing layer is a guanfacine-containing matrix layer comprising
i) guanfacine, preferably in the form of the free base;
ii) the at least one polymer; and
iii) the at least one additive, which is selected from the group consisting of dispersing agents, permeation enhancers, and solubilizers.

As explained above, the at least one polymer is preferably selected from the group consisting of silicone polymers, acrylate polymers, silicone acrylic hybrid polymers, polyisobutylenes, and styrene-isoprene-styrene block copolymers. In connection with the at least one additive, it is preferred that at least two additives, e.g. the combination of a dispersing agent and a permeation enhancer, or the combination of a dispersing agent and a solubilizer, or the combination of a permeation enhancer and a solubilizer, particularly preferably at least three additives additives, in particular the combination of a dispersing agent, a permeation enhancer and a solubilizer are present.

In a preferred embodiment, the guanfacine-containing layer comprises at least one polymer, which is a hybrid pressure-sensitive adhesive polymer. Thus, the guanfacine-containing layer is preferably a guanfacine-containing matrix layer, and particularly preferably a guanfacine-containing pressure sensitive adhesive matrix layer.

In one embodiment of the invention, the guanfacine-containing layer is obtainable by dispersing the guanfacine, preferably in the form of the free base. As a result, the guanfacine-containing layer of the TTS according to the invention typically comprises guanfacine in the form of the free base. In addition, the guanfacine may, in certain embodiments of the invention, partly be present in protonated form. However, it is preferred that at least 50 mol %, preferably at least 75 mol % of the guanfacine in the guanfacine-containing layer are present in the form of the free base. In a particular preferred embodiment, at least 90 mol %, preferably at least 95 mol %, more preferably at least 99 mol % of the guanfacine in the guanfacine-containing layer are present in the form of the free base.

In one embodiment of the invention, the guanfacine-containing layer structure, preferably the guanfacine-containing layer, more preferably the guanfacine-containing matrix layer of a transdermal therapeutic system according to the invention comprises guanfacine in an amount of from 1 to 100 mg/TTS, preferably from 8 to 72 mg/TTS. In a preferred embodiment, the guanfacine-containing layer structure, preferably the guanfacine-containing layer, more preferably the guanfacine-containing matrix layer comprises guanfacine in an amount of from 8 to 30 mg/TTS, e.g. in an amount of from 8 to 10 mg/TTS or from 17 to 19 mg/TTS. In other words, the total amount of guanfacine in the guanfacine-containing layer structure ranges from 1 to 100 mg/TTS, preferably from 8 to 72 mg/TTS, more preferably from 8 to 30 mg/TTS, e.g. from 8 to 10 mg/TTS or from 17 to 19 mg/TTS.

In another embodiment, the guanfacine loading in the guanfacine-containing layer structure ranges from 0.2 to 1.6 mg/cm$^2$, preferably from 0.4 to 1.2 mg/cm$^2$. Furthermore, it is preferred that the area of release of the TTS ranges from 1 to 100 cm$^2$, preferably from 2.5 to 50 cm$^2$.

In one embodiment of the invention, the guanfacine-containing layer comprises guanfacine in an amount of from 1 to 20% by weight, preferably from 3 to 16% by weight, more preferably from 4 to 14% by weight, most preferably from 5 to 13% by weight, based on the total weight of the guanfacine-containing layer. Particularly preferably, the guanfacine-containing layer comprises guanfacine in an amount of from 4 to 8% by weight, preferably from to 7% by weight, or in an amount of from 10 to 14% by weight, preferably from 11 to 13% by weight, based on the total weight of the guanfacine-containing layer, depending on the desired dosing strength of the TTS.

The guanfacine-containing layer structure, and preferably the guanfacine-containing layer, comprises at least one polymer. In a preferred embodiment, the at least one polymer is selected from the group consisting of silicone polymers, acrylate polymers, silicone acrylic hybrid polymers, polyisobutylenes, and styrene-isoprene-styrene block copolymers. In a more preferred embodiment, the at least one polymer is selected from the group consisting of silicone polymers and silicone acrylic hybrid polymers.

The guanfacine-containing layer structure, and preferably the guanfacine-containing layer, may also comprise at least two polymers. In a preferred embodiment, the guanfacine-containing layer comprises a first polymer selected from silicone polymers and silicone acrylic hybrid polymers, and optionally a second polymer selected from acrylate polymers, silicone acrylic hybrid polymers, and silicone polymers. In certain preferred embodiments, the guanfacine-containing layer comprises two different silicone acrylic hybrid polymers, two different silicone polymers, or a combination of a silicone acrylic hybrid polymer with an acrylate or silicone polymer.

The guanfacine-containing layer structure, and preferably the guanfacine-containing layer, may also comprise at least three polymers. In a preferred embodiment, the guanfacine-containing layer comprises a first polymer selected from silicone polymers and silicone acrylic hybrid polymers, and a second polymer selected from silicone polymers and silicone acrylic hybrid polymers, and optionally a third polymer selected from silicone polymers and acrylate polymers. In certain preferred embodiments, the guanfacine-containing layer comprises two different silicone acrylic hybrid polymers and a third polymer selected from silicone polymers and acrylate polymers.

Silicone polymers are obtainable by polycondensation of silanol endblocked polydimethylsiloxane with a silicate resin. The endblocking group is preferably a trimethylsilyl group. Preferred silicone polymers are amine-compatible silicone polymers. Amine-compatible silicone polymers can be obtained by reacting the silicone polymers with trimethylsilyl (e.g. hexamethyldisilazane) in order to reduce the silanol content of the polymer. Thus, it is preferred in the context of silicone polymers as used herein that the residual silanol functionality of the at least one silicone polymer is at least partly, preferably mostly or fully capped with trimethylsiloxy groups. Such silicone polymers are available from Dow Corning as explained in further detail below.

Acrylate polymers are obtainable from one or more monomers selected from acrylic acid, butylacrylate, 2-ethylhexylacrylate, glycidylmethacrylate, 2-hydroxyethylacrylate, methylacrylate, methylmethacrylate, t-octylacrylamide, and vinylacetate, preferably from one or more monomers selected from ethylhexylacrylate, glycidylmethacrylate, 2-hydroxyethylacrylate, and vinylacetate. Such acrylate polymers are available from Henkel as explained in further detail below.

Silicone acrylic hybrid polymers comprise a silicone phase a silicone phase and an acrylate phase, preferably in a weight ratio of from 60:40 to 40:60, most preferably in a weight ratio of 50:50. The silicone acrylic hybrid polymer typically comprises the reaction product of (a) a silicone-containing pressure-sensitive adhesive composition comprising acrylate or methacrylate functionality, (b) an ethylenically unsaturated monomer; and (c) an initiator. Further details regarding components (a), (b) and (c) are provided further below. It is to be understood that component (a) mainly forms the silicone phase, while component (b) mainly forms the acrylate phase of the silicone acrylic hybrid polymer. The acrylate phase influences the tackiness and the viscosity of the silicone acrylic hybrid polymer. It is therefore preferred that the ethylenically unsaturated monomer forming the acrylate phase is a combination of 2-ethylhexyl acrylate and methyl acrylate, preferably in a ratio of from 40:60 to 70:30. Preferred in terms of a high tackiness is a ratio of 60:40, although the viscosity is then lower. Preferred in terms of a higher viscosity is a ratio of 50:50, although the tackiness is then reduced. The silicone acrylic hybrid polymer in the guanfacine-containing layer preferably contains a continuous, acrylic external phase and a discontinuous, silicone internal phase.

Suitable polymers according to the present invention are described in further detail below in the sections "non-hybrid polymers" and "hybrid polymers". As indicated above, it is to be understood that the TTS according to the invention may comprise combinations of non-hybrid polymers as well as combinations of hybrid polymers as well as combinations of a non-hybrid polymer and a hybrid polymer. Preferred combinations of polymers include silicone and silicone, silicone and silicone acrylic hybrid polymer, silicone and acrylate, silicone acrylic hybrid polymer and acrylate, and silicone acrylic hybrid polymer and silicone acrylic hybrid polymer. In addition, a third polymer selected from silicone, acrylate, and silicone acrylic hybrid polymer may be present. The release properties and the adhesive properties of the TTS may thus be optimized.

In one embodiment of the invention, the guanfacine-containing layer comprises the at least one polymer in an amount of from 20 to 97%, preferably from 30 to 94%, most preferably from 35 to 94% by weight, based on the total weight of the guanfacine-containing layer. In a preferred embodiment, the guanfacine-containing layer comprises the at least one polymer in an amount of from 70 to 94% by weight, preferably from 74 to 89% by weight, based on the total weight of the guanfacine-containing layer. It is to be understood that the above indicated amounts of the at least one polymer may refer to one polymer, but also to a combination of polymers. Thus, the given amount refers to the overall amount of polymers.

In one preferred embodiment of the invention, the guanfacine-containing layer comprises only one polymer in an amount of form 60 to 97% by weight, preferably in an amount of from 70 to 94% by weight, based on the total weight of the guanfacine-containing layer. As indicated above, preferred polymers in this regard include silicone polymers and silicone acrylic hybrid polymers.

In another preferred embodiment of the invention, the guanfacine-containing layer comprises a first polymer and a second polymer, wherein the overall amount of the at least two polymers is from 60 to 97% by weight, preferably from 74 to 94% by weight, based on the total weight of the guanfacine-containing layer. Preferably, the guanfacine-containing layer comprises a first polymer in an amount of from 30 to 90% by weight, and a second polymer in an amount of from 1 to 40% by weight, based on the total weight of the guanfacine-containing layer. More preferably, the guanfacine-containing layer comprises a first polymer in an amount of from 38 to 85% by weight, and a second polymer in an amount of from 3 to 38% by weight, based on the total weight of the guanfacine-containing layer.

In one particularly preferred embodiment, the guanfacine-containing layer comprises a first polymer in an amount of from 70 to 78% by weight, preferably from 73 to 75% by weight, and a second polymer in an amount of from 1 to 8% by weight, preferably from 3 to 5% by weight, based on the total weight of the guanfacine-containing layer. In another particularly preferred embodiment, the guanfacine-containing layer comprises a first polymer in an amount of from 77 to 85% by weight, preferably from 79 to 83% by weight, and a second silicone acrylic hybrid polymer in an amount of from 1 to 8% by weight, preferably from 3 to 5% by weight, based on the total weight of the guanfacine-containing layer. In connection with these particularly preferred embodiments, it is preferred that the first and the second polymer are both silicone acrylic hybrid polymers.

In another particularly preferred embodiment, the guanfacine-containing layer comprises a first polymer in an amount of from 40 to 70% by weight, preferably from 40 to 60% by weight, and a second polymer in an amount of from 20 to 40% by weight, preferably from 25 to 40% by weight, based on the total weight of the guanfacine-containing layer. In connection with this particularly preferred embodiment, it is also preferred that the first and the second polymer are both silicone acrylic hybrid polymers.

In another particularly preferred embodiment, the guanfacine-containing layer comprises a first polymer in an amount of from 54 to 64% by weight, and a second polymer in an amount of from 15 to 25% by weight, based on the total weight of the guanfacine-containing layer. In connection with these particularly preferred embodiments, it is preferred that the first and the second polymer are both silicone polymers.

In another preferred embodiment of the invention, the guanfacine-containing layer comprises a first polymer, a second polymer, and a third polymer, wherein the overall amount of the at least two silicone acrylic hybrid polymers is from 60 to 97% by weight, preferably from 74 to 94% by weight, based on the total weight of the guanfacine-containing layer. Preferably, the guanfacine-containing layer comprises a first polymer in an amount of from 30 to 50% by weight, and a second polymer in an amount of from 1 to 10% by weight, and a third polymer in an amount of from 30 to 50% by weight, based on the total weight of the guanfacine-containing layer. More preferably, the guanfacine-containing layer comprises a first polymer in an amount of from 30 to 45% by weight, and a second polymer in an amount of from 1 to 5% by weight, and a third polymer in an amount of from 30 to 45% by weight, based on the total weight of the guanfacine-containing layer. In connection with these embodiments, it is preferred that the first and the second polymer are both silicone acrylic hybrid polymers, and the third polymer is a silicone polymer.

It is most preferred according to the invention that at least two polymers are present in the guanfacine-containing layer, wherein both polymers are silicone acrylic hybrid polymers. It is to be understood that the above-indicated preferences regarding the silicone acrylic hybrid polymers, in particular regarding the weight ratio of the acrylate to the silicone phase, regarding the components from which the silicone acrylic hybrid polymer is obtained, regarding the ethylenically unsaturated monomers from which the silicone acrylic hybrid polymer is formed as well as regarding the acrylic external phase and the silicone internal phase apply to both, the first and the second silicone acrylic hybrid polymer. In particular, it is preferred that the weight ratio of silicone phase to acrylate phase in the first silicone acrylic hybrid polymer is from 55:45 to 45:55, and that the ethylenically unsaturated monomers forming the acrylate comprise 2-ethylhexyl acrylate and methyl acrylate in a ratio of from 55:45 to 45:55. It is more preferred that the weight ratio of silicone phase to acrylate phase in the first silicone acrylic hybrid polymer is 50:50, and that the ethylenically unsaturated monomers forming the acrylate comprise 2-ethylhexyl acrylate and methyl acrylate in a ratio of 50:50. On the other hand, it is preferred that the weight ratio of silicone phase to acrylate phase in the second silicone acrylic hybrid polymer is from 55:45 to 45:55, and that the ethylenically unsaturated monomers forming the acrylate comprise 2-ethylhexyl acrylate and methyl acrylate in a ratio of from 65:35 to 55:45. It is more preferred that the weight ratio of silicone phase to acrylate phase in the second silicone acrylic hybrid polymer is 50:50, and that the ethylenically unsaturated monomers forming the acrylate comprise 2-ethylhexyl acrylate and methyl acrylate in a ratio of 60:40. Furthermore, it is for both silicone acrylic hybrid polymers preferred that the silicone phase is the internal phase and the acrylate phase is the external phase.

In one embodiment of the invention, the TTS according to the invention, and in particular the guanfacine-containing layer, more particularly the guanfacine-containing matrix layer, comprises at least one additive selected from the group consisting of dispersing agent, permeation enhancers, and solubilizers. Suitable additives are defined below and are preferably each present in an amount of from 0.5 to 10% by weight or from 1 to 10% by weight, based on the total weight of the guanfacine-containing layer. In one preferred embodiment, the at least one additive is a dispersing agent. In another preferred embodiment, the at least one additive is a permeation enhancer. In yet another preferred embodiment, the at least one additive is a solubilizer. In certain preferred embodiment, also combinations of the afore-mentioned additives are preferred, e.g. the combination of a dispersing agent and a permeation enhancer, or the combination of a dispersing agent and a solubilizer, or the combination of a permeation enhancer and a solubilizer, or the combination of a dispersing agent, a permeation enhancer and a solubilizer. The afore-mentioned additives are of particular advantage for providing the guanfacine in homogeneously dispersed and releasable form. It is to be understood that a dispersing agent may also act as permeation enhancer and vice versa. Similarly, also a solubilizer may additionally act as dispersing agent or permeation enhancer. Furthermore, the solubilizer may stabilize the guanfacine dispersion in the TTS and avoid crystallization. Moreover, the solubilizer can be helpful in optimizing the cohesion of the TTS. In certain preferred embodiments, the guanfacine-containing layer comprises at least one dispersing agent and at least one permeation enhancer, and optionally also at least one solubilizer.

In one preferred embodiment, the at least one additive is a dispersing agent, which is present in an amount of from 1 to 10% by weight, based on the total weight of the guanfacine-containing layer. Preferably, the dispersing agent is present in an amount of from 2 to 6% by weight, more preferably 3 to 5% by weight, based on the total weight of the guanfacine-containing layer.

In another preferred embodiment, the at least one additive is a permeation enhancer, which is present in an amount of from 1 to 10% by weight, based on the total weight of the guanfacine-containing layer. Preferably, the permeation enhancer is present in an amount of from 2 to 9% by weight, more preferably 3 to 5% by weight, based on the total weight of the guanfacine-containing layer.

In another embodiment, the at least one additive is a solubilizer, which is present in an amount of from 0.5 to 10% by weight, based on the total weight of the guanfacine-containing layer. Preferably, the solubilizer is present in an amount of from 0.5 to 4% by weight, more preferably 0.5 to 3% by weight, based on the total weight of the guanfacine-containing layer.

In one embodiment, the TTS according to the invention, and in particular the guanfacine-containing layer, more particularly the guanfacine-containing matrix layer, comprises at least two additives selected from the group consisting of dispersing agents, permeation enhancers, and solubilizers. Preferably, the guanfacine-containing layer, in particular the guanfacine-containing matrix layer comprises the combination of a dispersing agent and a permeation enhancer, or the combination of a dispersing agent and a solubilizer, or the combination of a permeation enhancer and a solubilizer, wherein each of the additives is present in an amount of from 0.5 to 10% by weight or from 1 to 10% by weight, based on the total weight of the guanfacine-containing layer.

In one preferred embodiment, the transdermal therapeutic system, and in particular the guanfacine-containing layer, more particularly the guanfacine-containing matrix layer, comprises at least two additives, wherein the first additive is a dispersing agent, which is present in an amount of from 1 to 10% by weight based on the total weight of the guanfacine-containing layer, and the second additive is a permeation enhancer, which is present in an amount of from 1 to 10% by weight based on the total weight of the guanfacine-containing layer. Preferably, the dispersing agent is present in an amount of from 1 to 6% by weight, and the permeation enhancer is present in an amount of from 2 to 9% by weight. More preferably, the dispersing agent is present in an amount of from 3 to 5% by weight, and the permeation enhancer is present in an amount of from 3 to 5% by weight.

In another preferred embodiment, the transdermal therapeutic system, and in particular the guanfacine-containing layer, more particularly the guanfacine-containing matrix layer, comprises at least two additives, wherein the first additive is a dispersing agent, which is present in an amount of from 1 to 10% by weight based on the total weight of the guanfacine-containing layer, and the second additive is a solubilizer, which is present in an amount of from 0.5 to 10% by weight based on the total weight of the guanfacine-containing layer. Preferably, the dispersing agent is present in an amount of from 1 to 6% by weight, and the solubilizer is present in an amount of from 0.5 to 4% by weight. More preferably, the dispersing agent is present in an amount of from 3 to 5% by weight, and the solubilizer is present in an amount of from 0.5 to 3% by weight.

In another preferred embodiment, the transdermal therapeutic system, and in particular the guanfacine-containing layer, more particularly the guanfacine-containing matrix layer, comprises at least two additives, wherein the first additive is a permeation enhancer, which is present in an amount of from 1 to 10% by weight based on the total weight of the guanfacine-containing layer, and the second additive is a solubilizer, which is present in an amount of from 0.5 to 10% by weight based on the total weight of the guanfacine-containing layer. Preferably, the permeation enhancer is present in an amount of from 2 to 9% by weight, and the solubilizer is present in an amount of from 0.5 to 4% by weight. Preferably, the permeation enhancer is present in an amount of from 3 to 5% by weight, and the solubilizer is present in an amount of from 0.5 to 3% by weight.

In one embodiment, the TTS according to the invention, and in particular the guanfacine-containing layer, more particularly the guanfacine-containing matrix layer, comprises at least three additives selected from the group consisting of dispersing agents, permeation enhancers, and solubilizers. Preferably, the guanfacine-containing layer, in particular the guanfacine-containing matrix layer comprises the combination of a dispersing agent, a permeation enhancer, and a solubilizer, wherein each of the additives is present in an amount of from 0.5 to 10% by weight or from 1 to 10% by weight, based on the total weight of the guanfacine-containing layer.

In one embodiment, the transdermal therapeutic system, and in particular the guanfacine-containing layer, more particularly the guanfacine-containing matrix layer, comprises at least three additives, wherein the first additive is a dispersing agent, which is present in an amount of from 1 to 10% by weight, based on the total weight of the guanfacine-containing layer, the second additive is a permeation enhancer, which is present in an amount of from 1 to 10% by weight, based on the total weight of the guanfacine-containing layer, and the third additive is a solubilizer, which is present in an amount of from 0.5 to 10% by weight, based on the total weight of the guanfacine-containing layer. Preferably, the dispersing agent is present in an amount of from 1 to 6% by weight, the permeation enhancer is present in an amount of from 2 to 9% by weight, and the solubilizer is present in an amount of from 0.5 to 4% by weight. More preferably, the dispersing agent is present in an amount of from 3 to 5% by weight, the permeation enhancer is present in an amount of from 3 to 5% by weight, and the solubilizer is present in an amount of from 0.5 to 3% by weight.

In connection with the above embodiments regarding the number of additives and the amounts of additives in the TTS according to the invention, and in particular the guanfacine-containing layer, more particularly the guanfacine-containing matrix layer, the following specific additives are preferred.

In a preferred embodiment, the dispersing agent is selected from the group consisting of esters of fatty acids with polyols, fatty alcohols, polyethylene glycols having a number average molecular weight of from 300 to 400, polyethylene glycol alkyl ethers, and wherein the dispersing agent is preferably polyethylene glycol $C_8$-$C_{20}$-alkyl ether having from 2 to 10 EO units, preferably from 2 to 6 EO units. A particularly preferred dispersing agent is polyoxyethylene (4) lauryl ether ($C_{12}H_{25}(OCH_2CH_2)_4OH$). This dispersing agent is, e.g., available from Merck under the tradename Brij L4®.

In a preferred embodiment, the permeation enhancer is selected from the group consisting of diethylene glycol monoethyl ether (transcutol), oleic acid, levulinic acid, caprylic/capric triglycerides, diisopropyl adipate, isopropyl myristate, isopropyl palmitate, lauryl lactate, triacetin, dimethylpropylene urea, and oleyl alcohol, and is preferably oleyl alcohol. Oleylalcohol is, e.g., available from BASF under the tradename Kollicream® OA.

In a preferred embodiment, the solubilizer is selected from the group consisting of copolymers derived from esters of acrylic and methacrylic acid, polyvinylpyrrolidone, vinylpyrrolidone-vinyl acetate copolymers, and polyvinyl caprolactam-polyvinyl acetate-polyethylene glycol graft copolymers. Preferably, the solubilizer is selected from polyvinylpyrrolidone and polyvinyl caprolactam-polyvinyl acetate-polyethylene glycol graft copolymers. Particularly preferred solubilizers are polyvinyl caprolactam-polyvinyl acetate-polyethylene glycol graft copolymers. Suitable polyvinyl caprolactam-polyvinyl acetate-polyethylene glycol graft copolymers are, e.g., available from BASF under the tradename Soluplus®, and preferably have the following structural formula, wherein l, m, and n are selected such that an average molecular weight determined by gel permeation chromatography is in the range of 90000 to 140000 g/mol.

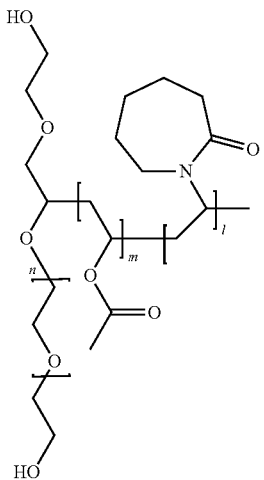

In certain preferred embodiments, the guanfacine-containing layer comprises at least one dispersing agent in an amount of from 2 to 6% by weight, at least one permeation enhancer in an amount of from 2 to 9% by weight, and optionally at least one solubilizer in an amount of from 0.5 to 4% by weight, in each case based on the total weight of the guanfacine-containing layer. Preferably, the guanfacine-containing layer comprises at least one dispersing agent in a amount of from 3 to 5% by weight, at least one permeation enhancer in an amount of from 3 to 5% by weight, and optionally at least one solubilizer in an amount of from 0.5 to 3% by weight, in each case based on the total weight of the guanfacine-containing layer. In connection with the above preferred weight-% amounts, the above preferred dispersing agents, permeation enhancers and solubilizers are preferred.

Accordingly, in a particularly preferred embodiment, the guanfacine-containing layer comprises a polyethylene glycol $C_8$-$C_{20}$-alkyl ether having from 2 to 10 EO units, preferably polyoxyethylene (4) lauryl ether, in an amount of from 2 to 6% by weight, oleyl alcohol in an amount of from 2 to 9% by weight, and optionally a polyvinyl caprolactam-polyvinyl acetate-polyethylene glycol graft copolymer, preferably as specified above, in an amount of from 0.5 to 4% by weight, in each case based on the total weight of the guanfacine-containing layer. Most preferably, the guanfacine-containing layer comprises a polyethylene glycol $C_8$-$C_{20}$-alkyl ether having from 2 to 10 EO units, preferably polyoxyethylene (4) lauryl ether, in an amount of from 3 to 5% by weight, oleyl alcohol in an amount of from 3 to 5% by weight, and optionally a polyvinyl caprolactam-polyvinyl acetate-polyethylene glycol graft copolymer, preferably as specified above, in an amount of from 0.5 to 3% by weight, in each case based on the total weight of the guanfacine-containing layer.

In one embodiment of the invention, the area weight of the guanfacine-containing layer ranges from 40 to 250 $g/m^2$, preferably from 50 to 180 $g/m^2$, more preferably from 70 to 180 $g/m^2$, e.g. from 75 to 150 $g/m^2$ or from 100 to 150 $g/m^2$. In certain preferred embodiments, the area weight ranges from 80 to 120 $g/m^2$, preferably from 90 to 100 $g/m^2$.

In view of the above, the present invention relates in one embodiment to a transdermal therapeutic system for the transdermal administration of guanfacine comprising a guanfacine-containing layer structure, said layer structure comprising:
A) a backing layer; and
B) a guanfacine-containing layer, preferably a guanfacine-containing matrix layer, comprising
  i) guanfacine in an amount of from 3 to 13% by weight, based on the total weight of the guanfacine-containing layer;
  ii) at least one silicone acrylic hybrid polymer in an amount of from 74 to 89% by weight, based on the total weight of the guanfacine-containing layer;
  iii) at least one dispersing agent in an amount of from 2 to 6% by weight, based on the total weight of the guanfacine-containing layer;
  iv) at least one permeation enhancer in an amount of from 2 to 6% by weight, based on the total weight of the guanfacine-containing layer; and
  v) optionally at least one solubilizer in an amount of from 0.5 to 4% by weight, based on the total weight of the guanfacine-containing layer.

In connection with this embodiment, it is further preferred that the guanfacine-containing layer structure does not comprise an additional skin-contact layer. Thus, the guanfacine-containing layer, preferably the guanfacine-containing matrix layer, preferably represents the skin contact layer and has pressure sensitive adhesive properties due to the silicone acrylic hybrid polymer.

In a preferred embodiment, the guanfacine-containing layer is a guanfacine-containing matrix layer, which comprises
  i) guanfacine in an amount of from 3 to 13% by weight, based on the total weight of the guanfacine-containing layer;
  ii) at least one silicone acrylic hybrid polymer in an amount of from 74 to 89% by weight, based on the total weight of the guanfacine-containing layer;
  iii) a polyethylene glycol $C_8$-$C_{20}$-alkyl ether having from 2 to 10 EO units in an amount of from 2 to 6% by weight, based on the total weight of the guanfacine-containing layer;
  iv) oleyl alcohol in an amount of from 2 to 6% by weight, based on the total weight of the guanfacine-containing layer; and
  v) optionally a polyvinyl caprolactam-polyvinyl acetate-polyethylene glycol graft copolymer in an amount of from 0.5 to 4% by weight, based on the total weight of the guanfacine-containing layer.

In one particularly preferred embodiment, the guanfacine-containing layer is a guanfacine-containing matrix layer, which comprises
  i) guanfacine in an amount of from 11 to 13% by weight, based on the total weight of the guanfacine-containing layer;
  ii) a first silicone acrylic hybrid polymer in an amount of from 73 to 75% by weight, based on the total weight of the guanfacine-containing layer, and a second silicone acrylic hybrid polymer in an amount of from 3 to 5% by weight, based on the total weight of the guanfacine-containing layer;
iii) a polyethylene glycol $C_8$-$C_{20}$-alkyl ether having from 2 to 10 EO units, preferably polyoxyethylene (4) lauryl ether, in an amount of from 3 to 5% by weight, based on the total weight of the guanfacine-containing layer;
iv) oleyl alcohol in an amount of from 3 to 5% by weight, based on the total weight of the guanfacine-containing layer; and
v) a polyvinyl caprolactam-polyvinyl acetate-polyethylene glycol graft copolymer in an amount of from 0.5 to 3% by weight, based on the total weight of the guanfacine-containing layer.

In connection with this embodiment, also the preferences regarding the first and the second silicone acrylic hybrid polymer as outlined above are preferred. In particular, it is preferred that the weight ratio of silicone phase to acrylate phase in the first silicone acrylic hybrid polymer is from 55:45 to 45:55, preferably about 50:50, and that the ethylenically unsaturated monomers forming the acrylate comprise 2-ethylhexyl acrylate and methyl acrylate in a ratio of 55:45 to 45:55, preferably 50:50. Furthermore, it is preferred that the weight ratio of silicone phase to acrylate phase in the second silicone acrylic hybrid polymer is from 55:45 to 45:55, preferably about 50:50, and that the ethylenically unsaturated monomers forming the acrylate comprise 2-ethylhexyl acrylate and methyl acrylate in a ratio of from 65:35 to 55:45, preferably 60:40. Furthermore, it is for both silicone acrylic hybrid polymers preferred that the silicone phase is the internal phase and the acrylate phase is the external phase. Moreover, it is preferred that the area weight of the guanfacine-containing layer ranges from 80 to 120 $g/m^2$, preferably from 90 to 100 $g/m^2$.

In another particularly preferred embodiment, the guanfacine-containing layer is a guanfacine-containing matrix layer, which comprises
i) guanfacine in an amount of from 5 to 7% by weight, based on the total weight of the guanfacine-containing layer;
ii) a first silicone acrylic hybrid polymer in an amount of from 79 to 83% by weight, based on the total weight of the guanfacine-containing layer, and a second silicone acrylic hybrid polymer in an amount of from 3 to 5% by weight, based on the total weight of the guanfacine-containing layer;
iii) a polyethylene glycol $C_8$-$C_{20}$-alkyl ether having from 2 to 10 EO units, preferably polyoxyethylene (4) lauryl ether, in an amount of from 3 to 5% by weight, based on the total weight of the guanfacine-containing layer; and
iv) oleyl alcohol in an amount of from 3 to 5% by weight, based on the total weight of the guanfacine-containing layer.

In connection with this embodiment, also the preferences regarding the first and the second silicone acrylic hybrid polymer as outlined above are preferred. In particular, it is preferred that the weight ratio of silicone phase to acrylate phase in the first silicone acrylic hybrid polymer is from 55:45 to 45:55, preferably about 50:50, and that the ethylenically unsaturated monomers forming the acrylate comprise 2-ethylhexyl acrylate and methyl acrylate in a ratio of from 55:45 to 45:55, preferably 50:50. Furthermore, it is preferred that the weight ratio of silicone phase to acrylate phase in the second silicone acrylic hybrid polymer is from 55:45 to 45:55, preferably about 50:50, and that the ethylenically unsaturated monomers forming the acrylate comprise 2-ethylhexyl acrylate and methyl acrylate in a ratio of from 65:35 to 55:45, preferably 60:40. Furthermore, it is for both silicone acrylic hybrid polymers preferred that the silicone phase is the internal phase and the acrylate phase is the external phase. Moreover, it is preferred that the area weight of the guanfacine-containing layer ranges from 80 to 120 $g/m^2$, preferably from 90 to 100 $g/m^2$.

Guanfacine

The TTS according to the invention comprises a guanfacine-containing layer structure, said guanfacine containing layer structure comprising A) a backing layer; and B) a guanfacine containing layer; wherein the transdermal therapeutic system comprises a silicone acrylic hybrid polymer. The guanfacine-containing layer, which is preferably a guanfacine-containing matrix layer, has been described in detail above.

In one embodiment of the invention, the amount of guanfacine contained in the guanfacine-containing layer structure ranges from to 100 mg/TTS, preferably from 8 to 72 mg/TTS, more preferably from 8 to 30 mg/TTS, e.g. from 8 to 10 mg/TTS or from 17 to 19 mg/TTS. Further details in this regard have been provided above.

In one embodiment of the invention, the guanfacine-containing layer structure preferably contains a therapeutically effective amount of guanfacine. More preferably, the therapeutically effective amount of guanfacine is present in the guanfacine-containing layer of the guanfacine-containing layer structure. Preferably, the guanfacine in the guanfacine-containing layer structure is present in the form of the free base.

In one embodiment of the invention, at least 50 mol %, preferably at least 75 mol % of the total amount of guanfacine in the TTS are present in the form of the free base. In a particular preferred embodiment, at least 90 mol %, preferably at least 95 mol %, more preferably at least 99 mol % of the total amount of guanfacine in the TTS are present in the form of the free base. Thus, it is preferred that at least 50 mol %, preferably at least 75 mol % of the guanfacine in the guanfacine-containing layer are present in the form of the free base. In a particular preferred embodiment, at least 90 mol %, preferably at least 95 mol %, more preferably at least 99 mol % of the guanfacine in the guanfacine-containing layer are present in the form of the free base. In certain embodiments, the guanfacine-containing layer is free of guanfacine salts.

In certain embodiments, the amount of guanfacine in the guanfacine-containing layer ranges from 1 to 20% by weight, preferably from 3 to 16% by weight, most preferably from 5 to 13% by weight, e.g. from 11 to 13% by weight or from 5 to 7% by weight, based on the total weight of the guanfacine-containing layer.

In one embodiment of the invention, the guanfacine-containing layer is obtainable by dispersing the guanfacine in the form of the free base. If the guanfacine-containing layer is a guanfacine-containing matrix layer, said layer is preferably obtainable by dispersing the guanfacine in the form of the free base in the polymeric carrier, which particularly preferably comprises the silicone acrylic hybrid polymer, and optionally at least one additive as defined above, in particular at least one dispersing agent.

In one embodiment, the guanfacine-containing layer comprises a pharmaceutically acceptable salt of guanfacine, such as guanfacine hydrochloride or guanfacine tartrate, preferably guanfacine hydrochloride. However, it is preferred according to the invention that the guanfacine in the guanfacine-containing layer is present in the form of the free base.

In certain embodiments, the guanfacine has a purity of at least 95%, preferably of at least 98%, and more preferably of at least 99% as determined by quantitative HPLC. Quantitative HPLC may be performed with Reversed-Phase-HPLC with UV detection.

Silicone Acrylic Hybrid Polymer

The TTS according to the present invention may comprise a silicone acrylic hybrid polymer. The silicone acrylic hybrid polymer comprises a polymerized hybrid species that includes silicone-based sub-species and acrylate-based sub-species that have been polymerized together. The silicone acrylic hybrid polymer thus comprises a silicone phase and an acrylic phase. Preferably, the silicone acrylic hybrid polymer is a silicone acrylic hybrid pressure-sensitive adhesive.

The silicone acrylic hybrid pressure-sensitive adhesives are usually supplied and used in solvents like n-heptane and ethyl acetate. The solids content of the pressure-sensitive adhesives is usually between 30% and 80%. The skilled person is aware that the solids content may be modified by adding a suitable amount of solvent.

Preferably, the weight ratio of silicone to acrylate in the silicone acrylic hybrid pressure-sensitive adhesive is from 5:95 to 95:5, or from 20:80 to 80:20, more preferably from 40:60 to 60:40, and most preferably the ratio of silicone to acrylate is about 50:50. Suitable silicone acrylic hybrid pressure-sensitive adhesives having a weight ratio of silicone to acrylate of 50:50 are, for example, the commercially available silicone acrylic hybrid pressure-sensitive adhesives 7-6102, Silicone/Acrylate Ratio 50/50, and 7-6302, Silicone/Acrylate Ratio 50/50, supplied in ethyl acetate by Dow Corning.

The preferred silicone acrylic hybrid pressure-sensitive adhesives in accordance with the invention are characterized by a solution viscosity at 25° C. and about 50% solids content in ethyl acetate of more than about 400 cP, or from about 500 cP to about 3,500 cP, in particular from about 1,000 cP to about 3,000 cP, more preferred from about 1,200 cP to about 1,800, or most preferred of about 1,500 cP or alternatively more preferred from about 2,200 cP to about 2,800 cP, or most preferred of about 2,500 cP, preferably as measured using a Brookfield RVT viscometer equipped with a spindle number 5 at 50 RPM.

These silicone acrylic hybrid pressure-sensitive adhesives may also be characterized by a complex viscosity at 0.1 rad/s at 30° C. of less than about 1.0e9 Poise, or from about 1.0e5 Poise to about 9.0e8 Poise, or more preferred from about 9.0e5 Poise to about 1.0e7 Poise, or most preferred about 4.0e6 Poise, or alternatively more preferred from about 2.0e6 Poise to about 9.0e7 Poise, or most preferred about 1.0e7 Poise, preferably as measured using a Rheometrics ARES rheometer, wherein the rheometer is equipped with 8 mm plates and the gap zeroed.

To prepare samples for measuring the rheological behavior using a Rheometrics ARES rheometer, between 2 and 3 grams of adhesive solution can be poured onto a SCOTCH-PAK 1022 fluoropolymer release liner and allow to sit for 60 minutes under ambient conditions. To achieve essentially solvent-free films of the adhesive, they can be placed in an oven at 110° C.+/−10° C. for 60 minutes. After removing from the oven and letting equilibrate to room temperature. The films can be removed from the release liner and folded over to form a square. To eliminate air bubbles the films can be compressed using a Carver press. The samples can then be loaded between the plates and are compressed to 1.5+/−0.1 mm at 30° C. The excess adhesive is trimmed and the final gap recorded. A frequency sweep between 0.01 to 100 rad/s can be performed with the following settings: Temperature=30° C.; strain=0.5-1% and data collected at 3 points/decade.

Suitable silicone acrylic hybrid pressure-sensitive adhesives which are commercially available include the PSA series 7-6100 and 7-6300 manufactured and supplied in n-heptane or ethyl acetate by Dow Corning (7-610X and 7-630X; X=1 n-heptane-based/X=2 ethyl acetate-based). For example, the 7-6102 silicone acrylic hybrid PSA having a silicone/acrylate ratio of 50/50 is characterized by a solution viscosity at 25° C. and about 50% solids content in ethyl acetate of 2,500 cP and a complex viscosity at 0.1 rad/s at 30° C. of 1.0e7 Poise. The 7-6302 silicone acrylic hybrid PSA having a silicone/acrylate ratio of 50/50 has a solution viscosity at 25° C. and about 50% solids content in ethyl acetate of 1,500 cP and a complex viscosity at 0.1 rad/s at 30° C. of 4.0e6 Poise.

Depending on the solvent in which the silicone acrylic hybrid pressure-sensitive adhesive is supplied, the arrangement of the silicone phase and the acrylic phase providing a silicone or acrylic continuous external phase and a corresponding discontinuous internal phase is different. If the silicone acrylic hybrid pressure-sensitive adhesive is provided in n-heptane, the composition contains a continuous, silicone external phase and a discontinuous, acrylic internal phase. If the silicone acrylic hybrid pressure-sensitive adhesive is provided in ethyl acetate, the composition contains a continuous, acrylic external phase and a discontinuous, silicone internal phase. After evaporating the solvent in which the silicone acrylic hybrid pressure-sensitive adhesive is provided, the phase arrangement of the resulting pressure-sensitive adhesive film or layer corresponds to the phase arrangement of the solvent-containing adhesive coating composition. For example, in the absence of any substance that may induce an inversion of the phase arrangement in a silicone acrylic hybrid pressure sensitive adhesive composition, a pressure-sensitive adhesive layer prepared from a silicone acrylic hybrid pressure-sensitive adhesive in n-heptane provides a continuous, silicone external phase and a discontinuous, acrylic internal phase, a pressure-sensitive adhesive layer prepared from a silicone acrylic hybrid pressure-sensitive adhesive in ethyl acetate provides a continuous, acrylic external phase and a discontinuous, silicone internal phase. The phase arrangement of the compositions can, for example, be determined in peel force tests with pressure-sensitive adhesive films or layers prepared from the silicone acrylic hybrid PSA compositions which are attached to a siliconized release liner. The pressure-sensitive adhesive film contains a continuous, silicone external phase if the siliconized release liner cannot or can only hardly be removed from the pressure-sensitive adhesive film (laminated to a backing film) due to the blocking of the two silicone surfaces. Blocking results from the adherence of two silicone layers which comprise a similar surface energy. The silicone adhesive shows a good spreading on the siliconized liner and therefore can create a good adhesion to the liner. If the siliconized release liner can easily be removed the pressure-sensitive adhesive film contains a continuous, acrylic external phase. The acrylic adhesive has no good spreading due to the different surface energies and thus has a low or almost no adhesion to the siliconized liner.

According to a preferred embodiment of the invention the silicone acrylic hybrid polymer is a silicone acrylic hybrid pressure-sensitive adhesive obtainable from a silicon-containing pressure-sensitive adhesive composition comprising acrylate or methacrylate functionality. It is to be understood that the silicon-containing pressure-sensitive adhesive composition comprising acrylate or methacrylate functionality can include only acrylate functionality, only methacrylate functionality, or both acrylate functionality and methacrylate functionality.

According to certain embodiments of the invention the silicone acrylic hybrid pressure-sensitive adhesive comprises the reaction product of (a) a silicon-containing pressure-sensitive adhesive composition comprising acrylate or methacrylate functionality, (b) an ethylenically unsaturated monomer, and (c) an initiator. That is, the silicone acrylic hybrid pressure-sensitive adhesive is the product of the chemical reaction between these reactants ((a), (b), and (c)). In particular, the silicone acrylic hybrid pressure-sensitive adhesive includes the reaction product of (a) a silicon-containing pressure-sensitive adhesive composition comprising acrylate or methacrylate functionality, (b) a (meth)acrylate monomer, and (c) an initiator (i.e., in the presence of the initiator). That is, the silicone acrylic hybrid pressure-sensitive adhesive includes the product of the chemical reaction between these reactants ((a), (b), and (c)).

The reaction product of (a) a silicon-containing pressure-sensitive adhesive composition comprising acrylate or methacrylate functionality, (b) an ethylenically unsaturated monomer, and (c) an initiator may contain a continuous, silicone external phase and a discontinuous, acrylic internal phase or the reaction product of (a), (b), and (c) may contain a continuous, acrylic external phase and a discontinuous, silicone internal phase.

The silicon-containing pressure-sensitive adhesive composition comprising acrylate or methacrylate functionality (a) is typically present in the silicone acrylic hybrid pressure-sensitive adhesive in an amount of from 5 to 95, more typically 25 to 75, parts by weight based on 100 parts by weight of the hybrid pressure-sensitive adhesive.

The ethylenically unsaturated monomer (b) is typically present in the silicone acrylic hybrid pressure-sensitive adhesive in an amount of from 5 to 95, more typically 25 to 75, parts by weight based on 100 parts by weight of the hybrid pressure-sensitive adhesive.

The initiator (c) is typically present in the silicone acrylic hybrid pressure-sensitive adhesive in an amount of from 0.005 to 3, more typically from 0.01 to 2, parts by weight based on 100 parts by weight of the hybrid pressure-sensitive adhesive.

According to certain embodiments of the invention the silicon-containing pressure-sensitive adhesive composition comprising acrylate or methacrylate functionality (a) comprises the condensation reaction product of (a1) a silicone resin, (a2) a silicone polymer, and (a3) a silicon-containing capping agent which provides said acrylate or methacrylate functionality. The silicone resin (a1) may also be referred to as silicate resin or silica resin. Preferably, the silicone polymer (a2) is a polysiloxane, preferably polydimethylsiloxane. It is to be understood that (a1) and (a2) form a silicone-based pressure sensitive adhesive by polycondensation, and that the acrylate or methacrylate functionality is introduced by reaction with (a3).

According to certain embodiments of the invention the silicon-containing pressure-sensitive adhesive composition comprising acrylate or methacrylate functionality (a) comprises the condensation reaction product of:

(a1) a silicone resin,
(a2) a silicone polymer, and
(a3) a silicon-containing capping agent which provides said acrylate or methacrylate functionality, wherein said silicon-containing capping agent is of the general formula $XYR'_bSiZ_{3-b}$ wherein
  X is a monovalent radical of the general formula AE- where E is —O— or —NH— and A is an acryl group or a methacryl group,
  Y is a divalent alkylene radical having from 1 to 6 carbon atoms,
  R' is a methyl or a phenyl radical,
  Z is a monovalent hydrolyzable organic radical or a halogen, and
  b is 0 or 1;
wherein the silicone resin and silicone polymer are reacted to form a pressure-sensitive adhesive, wherein the silicon-containing capping agent is introduced prior to, during, or after the silicone resin and silicone polymer are reacted, and wherein:
  the silicon-containing capping agent reacts with the pressure-sensitive adhesive after the silicone resin and silicone polymer have been condensation reacted to form the pressure-sensitive adhesive; or
  the silicon-containing capping agent reacts in-situ with the silicone resin and silicone polymer.

According to certain embodiments of the invention the silicon-containing pressure-sensitive adhesive composition comprising acrylate or methacrylate functionality comprises the condensation reaction product of a pressure sensitive adhesive and a silicon-containing capping agent which provides said acrylate or methacrylate functionality. That is, the silicon-containing pressure sensitive adhesive composition comprising acrylate or methacrylate functionality is essentially a pressure sensitive adhesive that has been capped or endblocked with the silicon-containing capping agent which provides said acrylate or methacrylate functionality, wherein the pressure sensitive adhesive comprises the condensation reaction product of the silicone resin and the silicone polymer. Preferably, the silicone resin reacts in an amount of from 30 to 80 parts by weight to form the pressure sensitive adhesive, and the silicone polymer reacts in an amount of from 20 to 70 parts by weight to form the pressure sensitive adhesive. Both of these parts by weight are based on 100 parts by weight of the pressure sensitive adhesive. Although not required, the pressure sensitive adhesive may comprise a catalytic amount of a condensation catalyst. A wide array of silicone resins and silicone polymers are suitable to make up the pressure sensitive adhesive.

According to certain embodiments of the invention the silicone acrylic hybrid pressure-sensitive adhesive is the reaction product of:

(a) a silicon-containing pressure-sensitive adhesive composition comprising acrylate or methacrylate functionality that comprises the condensation reaction product of:
  (a1) a silicone resin,
  (a2) a silicone polymer, and
  (a3) a silicon-containing capping agent which provides said acrylate or methacrylate functionality, wherein said silicon-containing capping agent is of the general formula $XYR'_bSiZ_{3-b}$, wherein
    X is a monovalent radical of the general formula AE- where E is —O— or —NH— and A is an acryl group or a methacryl group,
    Y is a divalent alkylene radical having from 1 to 6 carbon atoms,
    R' is a methyl or a phenyl radical, Z is a monovalent hydrolyzable organic radical or a halogen, and b is 0 or 1;

wherein the silicone resin and silicone polymer are reacted to form a pressure-sensitive adhesive, wherein the silicon-containing capping agent is introduced prior to, during, or after the silicone resin and silicone polymer are reacted, and wherein:

the silicon-containing capping agent reacts with the pressure-sensitive adhesive after the silicone resin and silicone polymer have been condensation reacted to form the pressure-sensitive adhesive; or the silicon-containing capping agent reacts in-situ with the silicone resin and silicone polymer;

(b) an ethylenically unsaturated monomer; and
(c) an initiator.

The silicone acrylic hybrid composition used in the present invention may be described by being prepared by a method comprising the steps of:

(i) providing a silicon-containing pressure-sensitive adhesive composition comprising acrylate or methacrylate functionality that comprises the condensation reaction product of:

a silicone resin, a silicone polymer, and a silicon-containing capping agent which provides said acrylate or methacrylate functionality, wherein said silicon-containing capping agent is of the general formula $XYR'_bSiZ_{3-b}$, wherein X is a monovalent radical of the general formula AE- where E is —O— or —NH— and A is an acryl group or a methacryl group, Y is a divalent alkylene radical having from 1 to 6 carbon atoms, R' is a methyl or a phenyl radical, Z is a monovalent hydrolyzable organic radical or a halogen, and b is 0 or 1;

wherein the silicone resin and silicone polymer are reacted to form a pressure-sensitive adhesive, wherein the silicon-containing capping agent is introduced prior to, during, or after the silicone resin and silicone polymer are reacted, and wherein:

the silicon-containing capping agent reacts with the pressure-sensitive adhesive after the silicone resin and silicone polymer have been condensation reacted to form the pressure-sensitive adhesive; or the silicon-containing capping agent reacts in-situ with the silicone resin and silicone polymer;

(ii) polymerizing an ethylenically unsaturated monomer and the silicon-containing pressure-sensitive adhesive composition comprising acrylate or methacrylate functionality of step (i) in the presence of an initiator to form a silicone acrylic hybrid composition, optionally at a temperature of from 50° C. to 100° C., or from 65° C. to 90° C.

During the polymerization of the ethylenically unsaturated monomer and the silicon-containing pressure-sensitive adhesive composition comprising acrylate or methacrylate functionality, the silicone to acrylic ratio can be controlled and optimized as desired. The silicone to acrylic ratio can be controlled by a wide variety of mechanisms in and during the method. An illustrative example of one such mechanism is the rate controlled addition of the ethylenically unsaturated monomer or monomers to the silicon-containing pressure-sensitive adhesive composition comprising acrylate or methacrylate functionality. In certain applications, it may be desirable to have the silicone-based sub-species, or the overall silicone content, to exceed the acrylate-based sub-species, or the overall acrylic content. In other applications, it may be desirable for the opposite to be true. Independent of the end application, it is generally preferred, as already described above, that the silicon-containing pressure-sensitive adhesive composition comprising acrylate or methacrylate functionality is preferably present in the silicone acrylic hybrid composition in an amount of from about 5 to about 95 parts by weight, more preferably from about 25 to about 75 parts by weight, and still more preferably from about 40 to about 60 parts by weight based on 100 parts by weight of the silicone acrylic hybrid composition.

According to a certain embodiment of the invention, the silicone acrylic hybrid composition used in the present invention may be described by being prepared by a method comprising the steps of:

(i) providing a silicon-containing pressure-sensitive adhesive composition comprising acrylate or methacrylate functionality that comprises the condensation reaction product of:

a silicone resin, a silicone polymer, and a silicon-containing capping agent which provides said acrylate or methacrylate functionality, wherein said silicon-containing capping agent is of the general formula $XYR'_bSiZ_{3-b}$, wherein X is a monovalent radical of the general formula AE- where E is —O— or —NH— and A is an acryl group or a methacryl group, Y is a divalent alkylene radical having from 1 to 6 carbon atoms, R' is a methyl or a phenyl radical, Z is a monovalent hydrolyzable organic radical or a halogen, and b is 0 or 1;

wherein the silicone resin and silicone polymer are reacted to form a pressure-sensitive adhesive, wherein the silicon-containing capping agent is introduced prior to, during, or after the silicone resin and silicone polymer are reacted, and wherein:

the silicon-containing capping agent reacts with the pressure-sensitive adhesive after the silicone resin and silicone polymer have been condensation reacted to form the pressure-sensitive adhesive; or the silicon-containing capping agent reacts in-situ with the silicone resin and silicone polymer;

(ii) polymerizing an ethylenically unsaturated monomer and the silicon-containing pressure-sensitive adhesive composition comprising acrylate or methacrylate functionality of step (i) in a first solvent in the presence of an initiator at a temperature of from 50° C. to 100° C. to form a silicone acrylic hybrid composition;

(iii) removing the first solvent; and (iv) adding a second solvent to form the silicone acrylic hybrid composition, wherein the phase arrangement of the silicone acrylic hybrid composition is selectively controlled by selection of the second solvent.

The silicone acrylic hybrid PSA composition used in the present invention may also be described by being prepared by a method comprising the steps of:

(i) providing a silicon-containing pressure-sensitive adhesive composition comprising acrylate or methacrylate functionality that comprises the condensation reaction product of:

a silicone resin, a silicone polymer, and a silicon-containing capping agent which provides said acrylate or methacrylate functionality, wherein said silicon-containing capping agent is of the general formula XYR'$_b$SiZ$_{3-b}$, wherein
- X is a monovalent radical of the general formula AE- where E is —O— or —NH— and A is an acryl group or a methacryl group,
- Y is a divalent alkylene radical having from 1 to 6 carbon atoms,
- R' is a methyl or a phenyl radical,
- Z is a monovalent hydrolyzable organic radical or a halogen, and
- b is 0 or 1;

wherein the silicone resin and silicone polymer are reacted to form a pressure-sensitive adhesive, wherein the silicon-containing capping agent is introduced prior to, during, or after the silicone resin and silicone polymer are reacted, and wherein:
- the silicon-containing capping agent reacts with the pressure-sensitive adhesive after the silicone resin and silicone polymer have been condensation reacted to form the pressure-sensitive adhesive; or
- the silicon-containing capping agent reacts in-situ with the silicone resin and silicone polymer;

(ii) polymerizing an ethylenically unsaturated monomer and the silicon-containing pressure-sensitive adhesive composition comprising acrylate or methacrylate functionality of step (i) in a first solvent in the presence of an initiator at a temperature of from 50° C. to 100° C. to form a silicone acrylic hybrid composition;

(iii) adding a processing solvent, wherein the processing solvent has a higher boiling point than the first solvent, and (iv) applying heat at a temperature of from 70° C. to 150° C. such that a majority of the first solvent is selectively removed;

(v) removing the processing solvent; and.

(vi) adding a second solvent to form the silicone acrylic hybrid composition, wherein the phase arrangement of the silicone acrylic hybrid composition is selectively controlled by selection of the second solvent.

The silicone resin according to the previous paragraphs may contain a copolymer comprising triorganosiloxy units of the formula R$^X_3$SiO$_{1/2}$ and tetrafunctional siloxy units of the formula SiO$_{4/2}$ in a ratio of from 0.1 to 0.9, preferably of about 0.6 to 0.9, triorganosiloxy units for each tetrafunctional siloxy unit. Preferably, each R$^X$ independently denotes a monovalent hydrocarbon radical having from 1 to 6 carbon atoms, vinyl, hydroxyl or phenyl groups.

The silicone polymer according to the previous paragraphs may comprise at least one polydiorganosiloxane and is preferably end-capped (end-blocked) with a functional group selected from the group consisting of hydroxyl groups, alkoxy groups, hydride groups, vinyl groups, or mixtures thereof. The diorganosubstituent may be selected from the group consisting of dimethyl, methylvinyl, methylphenyl, diphenyl, methylethyl, (3,3,3-trifluoropropyl) methyl and mixtures thereof. Preferably, the diorganosubstituents contain only methyl groups. The molecular weight of polydiorganosiloxane will typically range from about 50,000 to about 1,000,000, preferably, from about 80,000 to about 300,000. Preferably, the polydiorganosiloxane comprises AR$^X$SiO units terminated with endblocking TR$^X$A-SiO$_{1/2}$ units, wherein the poly-diorganosiloxane has a viscosity of from about 100 centipoise to about 30,000,000 centipoise at 25° C., each A radical is independently selected from R$^X$ or halohydrocarbon radicals having from 1 to 6 carbon atoms, each T radical is independently selected from the group consisting of R$^X$, OH, H or OR$^Y$, and each R$^Y$ is independently an alkyl radical having from 1 to 4 carbon atoms.

As an example using forms of the preferred silicone resin and the preferred silicone polymer, one type of pressure sensitive adhesive is made by:

mixing (i) from 30 to 80 inclusive parts by weight of at least one resin copolymer containing silicon-bonded hydroxyl radicals and consisting essentially of R$^X_3$SiO$_{1/2}$ units and SiO$_{4/2}$ units in a mole ratio of 0.6 to 0.9 R$^X_3$SiO$_{1/2}$ units for each SiO$_{4/2}$ unit present, (ii) between about 20 and about 70 parts by weight of at least one polydiorganosiloxane comprising AR$^X$SiO units terminated with endblocking TR$^X$A-SiO$_{1/2}$ units, wherein the polydiorganosiloxane has a viscosity of from about 100 centipoise to about 30,000,000 centipoise at 25° C. and each R$^X$ is a monovalent organic radical selected from the group consisting of hydrocarbon radicals of from 1 to 6 inclusive carbon atoms, each A radical is independently selected from R$^X$ or halohydrocarbon radicals having from 1 to 6 inclusive carbon atoms, each T radical is independently selected from the group consisting of R$^X$, OH, H or OR$^Y$, and each R$^Y$ is independently an alkyl radical of from 1 to 4 inclusive carbon atoms; a sufficient amount of (iii) at least one of the silicon-containing capping agents, also referred to throughout as endblocking agents, described below and capable of providing a silanol content, or concentration, in the range of 5,000 to 15,000, more typically 8,000 to 13,000, ppm, when desirable an additional catalytic amount of (iv) a mild silanol condensation catalyst in the event that none is provided by (ii), and when necessary, an effective amount of (v) an organic solvent which is inert with respect to (i), (ii), (iii) and (iv) to reduce the viscosity of a mixture of (i), (ii), (iii), and (iv), and condensing the mixture of (i), (ii), (iii) and (iv) at least until a substantial amount of the silicon-containing capping agent or agents have reacted with the silicon-bonded hydroxyl radicals and T radicals of (i) and (ii). Additional organosilicon endblocking agents can be used in conjunction with the silicon-containing capping agent or agents (iii) of the present invention.

The silicon-containing capping agent according to the previous paragraphs may be selected from the group of acrylate functional silanes, acrylate functional silazanes, acrylate functional disilazanes, acrylate functional disiloxanes, methacrylate functional silanes, methacrylate functional silazanes, methacrylate functional disilazanes, methacrylate functional disiloxanes, and combinations thereof and may be described as to be of the general formula XYR'$_b$SiZ$_{3-b}$, wherein X is a monovalent radical of the general formula AE- where E is —O— or —NH— and A is an acryl group or a methacryl group, Y is a divalent alkylene radical having from 1 to 6 carbon atoms, R' is a methyl or a phenyl radical, Z is a monovalent hydrolyzable organic radical or a halogen, and b is 0, 1 or 2. Preferably, the monovalent hydrolyzable organic radical is of the general formula R"O— where R" is an alkylene radical. Most preferably, this particular endblocking agent is selected from the group of 3-methacryloxypropyldimethylchlorosilane, 3-methacryloxypropyldichlorosilane, 3-methacryloxypropyltrichlorosilane, 3-methacryloxypropyldimethylmethoxysilane, 3-methacryloxypropylmethyldimethoxysilane, 3-meth-acryloxypropyltrimethoxysilane, 3-methacryloxypropyldimethylethoxysilane, 3-methacryloxypropylmethyldiethoxysilane, 3-methacryloxypropyltriethoxysilane, (methacryloxymethyl)dimethylmethoxysilane, (methacryloxymethyl)methyldimethoxysilane, (methacryloxymethyl) trimethoxysilane, (methacryloxymethyl)dimethylethoxysilane, (methacryloxymethyl)methyldiethoxysilane, methacryloxymethyltriethoxysilane, methacryloxy-propyl-triisopropoxysilane, 3-methacryloxypropyldimethylsilazane, 3-acryloxy-propyldimethylchlorosilane, 3-acryloxy-propyldichlorosilane, 3-acryloxypropyl-trichlorosilane, 3-acryloxypropyldimethylmethoxysilane, 3-acryloxy-propylmethyldimethoxysilane, 3-acryloxypropyltrimethoxysilane, 3-acryloxypropyl-dimethylsilazane, and combinations thereof.

The ethylenically unsaturated monomer according to the previous paragraphs can be any monomer having at least one carbon-carbon double bond. Preferably, the ethylenically unsaturated monomer according to the previous paragraphs may be a compound selected from the group consisting of aliphatic acrylates, aliphatic methacrylates, cycloaliphatic acrylates, cycloaliphatic methacrylates, and combinations thereof. It is to be understood that each of the compounds, the aliphatic acrylates, the aliphatic methacrylates, the cycloaliphatic acrylates, and the cycloaliphatic methacrylates, include an alkyl radical. The alkyl radicals of these compounds can include up to 20 carbon atoms. The aliphatic acrylates that may be selected as one of the ethylenically unsaturated monomers are selected from the group consisting of methyl acrylate, ethyl acrylate, propyl acrylate, n-butyl acrylate, iso-butyl acrylate, tert-butyl acrylate, hexyl acrylate, 2-ethylhexyl acrylate, iso-octyl acrylate, iso-nonyl acrylate, iso-pentyl acrylate, tridecyl acrylate, stearyl acrylate, lauryl acrylate, and mixtures thereof. The aliphatic methacrylates that may be selected as one of the ethylenically unsaturated monomers are selected from the group consisting of methyl methacrylate, ethyl methacrylate, propyl methacrylate, n-butyl methacrylate, iso-butyl meth-acrylate, tert-butyl methacrylate, hexyl methacrylate, 2-eth-ylhexyl methacrylate, iso-octyl methacrylate, iso-nonyl methacrylate, iso-pentyl methacrylate, tridecyl methacrylate, stearyl methacrylate, lauryl methacrylate, and mixtures thereof. The cycloaliphatic acrylate that may be selected as one of the ethylenically unsaturated monomers is cyclohexyl acrylate, and the cycloaliphatic methacrylate that may be selected as one of the ethylenically unsaturated monomers is cyclohexyl methacrylate.

It is to be understood that the ethylenically unsaturated monomer used for preparing the silicone acrylic hybrid pressure sensitive adhesive may be more than one ethylenically unsaturated monomer. That is, a combination of ethylenically unsaturated monomers may be polymerized, more specifically co-polymerized, along with the silicon-containing pressure sensitive adhesive composition comprising acrylate or methacrylate functionality and the initiator. According to a certain embodiment of the invention, the silicone acrylic hybrid pressure-sensitive adhesive is prepared by using at least two different ethylenically unsaturated monomers, preferably selected from the group of 2-ethylhexyl acrylate and methyl acrylate, more preferably in a ratio of 50% 2-ethylhexyl acrylate and 50% methyl acrylate, or in a ratio of 60% 2-ethylhexyl acrylate and 40% methyl acrylate as the acrylic monomer.

The initiator according to the previous paragraphs may be any substance that is suitable to initiate the polymerization of the silicon-containing pressure sensitive adhesive composition comprising acrylate or methacrylate functionality and the ethylenically unsaturated monomer to form the silicone acrylic hybrid. For example, free radical initiators selected from the group of peroxides, azo compounds, redox initiators, and photo-initiators may be used.

Further suitable silicone resins, silicone polymers, silicon-containing capping agents, ethylenically unsaturated monomers, and initiators that can be used in accordance with the previous paragraphs are detailed in WO 2007/145996, EP2 599 847 A1, and WO 2016/130408.

According to a certain embodiment of the invention, the silicone acrylic hybrid polymer comprises a reaction product of a silicone polymer, a silicone resin and an acrylic polymer, wherein the acrylic polymer is covalently self-cross-linked and covalently bound to the silicone polymer and/or the silicone resin.

According to a certain other embodiment of the invention, the silicone acrylic hybrid polymer comprises a reaction product of a silicone polymer, a silicone resin and an acrylic polymer, wherein the silicone resin contains triorganosiloxy units $R_3SiO_{1/2}$ where R is an organic group, and tetrafunctional siloxy units $SiO_{4/2}$ in a mole ratio of from 0.1 to 0.9 $R_3SiO_{1/2}$ units for each $SiO_{4/2}$.

The acrylic polymer may comprise at least an alkoxysilyl functional monomer, polysiloxane-containing monomer, halosilyl functional monomer or alkoxy halosilyl functional monomer. Preferably, the acrylic polymer is prepared from alkoxysilyl functional monomers selected from the group consisting of trialkoxylsilyl (meth)acrylates, dialkoxyalkylsilyl (meth)acrylates, and mixtures thereof, or comprises end-capped alkoxysilyl functional groups. The alkoxysilyl functional groups may preferably be selected from the group consisting of trimethoxylsilyl groups, dimethoxymethylsilyl groups, triethoxylsilyl, diethoxymethylsilyl groups and mixtures thereof.

The acrylic polymer may also be prepared from a mixture comprising polysiloxane-containing monomers, preferably from a mixture comprising polydimethylsiloxane mono (meth)acrylate.

The silyl functional monomers will typically be used in amounts of from 0.2 to 20% by weight of the acrylic polymer, more preferably the amount of silyl functional monomers will range from about 1.5 to about 5% by weight of the acrylic polymer.

The amount of polysiloxane-containing monomer will typically be used in amounts of from 1.5 to 50% by weight of the acrylic polymer, more preferably the amount of polysiloxane-containing monomers will range from 5 to 15% by weight of the acrylic polymer.

Alternatively, the acrylic polymer comprises a block or grafted copolymer of acrylic and polysiloxane. An example of a polysiloxane block copolymer is polydimethylsiloxane-acrylic block copolymer. The preferred amount of siloxane block is 10 to 50% weight of the whole block polymer.

The acrylic polymer comprises alkyl (meth)acrylate monomers. Preferred alkyl (meth)acrylates which may be used have up to about 18 carbon atoms in the alkyl group, preferably from 1 to about 12 carbon atoms in the alkyl group. Preferred low glass transition temperature (Tg) alkyl acrylate with a homopolymer Tg of less than about 0° C. have from about 4 to about 10 carbon atoms in the alkyl group and include butyl acrylate, amyl acrylate, hexyl acrylate, 2-ethylhexyl acrylate, octyl acrylate, isooctyl acrylate, decyl acrylate, isomers thereof, and combinations thereof. Particularly preferred are butyl acrylate, 2-ethylhexyl acrylate and isooctyl acrylate. The acrylic polymer components may further comprise (meth)acrylate monomers having a high Tg such as methyl acrylate, ethyl acrylate, methyl methacrylate and isobutyl methacrylate.

The acrylic polymer component may further comprise a polyisobutylene group to improve cold flow properties of the resultant adhesive.

The acrylic polymer components may comprise nitrogen-containing polar monomers. Examples include N-vinyl pyrrolidone, N-vinyl caprolactam, N-tertiary octyl acrylamide, dimethyl acrylamide, diacetone acrylamide, N-tertiary butyl acrylamide, N-isopropyl acrylamide, cyanoethylacrylate, N-vinyl acetamide and N-vinyl formamide.

The acrylic polymer component may comprise one or more hydroxyl containing monomers such as 2-hydroxyethyl acrylate, 2-hydroxyethyl methacrylate, hydroxypropyl acrylate and/or hydroxypropyl methacrylate.

The acrylic polymer components may, if desired, comprise carboxylic acid containing monomers. Useful carboxylic acids preferably contain from about 3 to about 6 carbon atoms and include, among others, acrylic acid, methacrylic acid, itaconic acid, β-carboxyethyl acrylate and the like. Acrylic acid is particularly preferred.

Other useful, well known co-monomers include vinyl acetate, styrene, cyclohexyl acrylate, alkyl di(meth)acrylates, glycidyl methacrylate and allyl glycidyl ether, as well as macromers such as, for example, poly(styryl)methacrylate.

One acrylic polymer component that can be used in the practice of the invention is an acrylic polymer that comprises from about 90 to about 99.5 wt % of butyl acrylate and from about 0.5 to about 10 wt % dimethoxymethylsilyl methacrylate.

According to a certain embodiment of the invention the silicone acrylic hybrid polymer may be prepared by a) reacting silicone polymer with silicone resin to form a resultant product, b) reacting the resultant product of a) with an acrylic polymer containing reactive functionality, wherein the components are reacted in an organic solvent.

According to a certain embodiment of the invention the silicone acrylic hybrid polymer may be prepared by a) reacting a silicone resin with an acrylic polymer containing reactive functionality to form a resultant product, b) reacting the resultant product of a) with silicone polymer, wherein the components are reacted in an organic solvent.

According to a certain embodiment of the invention the silicone acrylic hybrid polymer may be prepared by a) reacting a silicone polymer with an acrylic polymer containing reactive functionality to form a resultant product, b) reacting the resultant product of a) with silicone resin, wherein the components are reacted in an organic solvent.

Further suitable acrylic polymers, silicone resins, and silicone polymers that can be used for chemically reacting together a silicone polymer, a silicone resin and an acrylic polymer to provide a silicone acrylic hybrid polymer in accordance with the previous paragraphs are detailed in WO2010/124187.

According to certain embodiments of the invention, the silicone acrylic hybrid polymer used in the TTS is blended with one or more non-hybrid polymers, preferably the silicone acrylic hybrid polymer is blended with one or more non-hybrid pressure sensitive adhesives (e.g. pressure-sensitive adhesives based on polysiloxane or acrylates).

Non-Hybrid Polymers

According to a certain embodiment of the invention, the TTS comprises a non-hybrid polymer (e.g. non-hybrid pressure-sensitive adhesives). Non-hybrid polymers (e.g. non-hybrid pressure-sensitive adhesives) are polymers (e.g. polymer-based pressure-sensitive adhesives) which do not include a hybrid species. Preferred are non-hybrid polymers (e.g. non-hybrid pressure-sensitive adhesives) based on polysiloxanes, acrylates, polyisobutylenes, or styrene-isoprene-styrene block copolymers.

The non-hybrid polymers (e.g. the non-hybrid pressure-sensitive adhesives) may be contained in the active agent-containing layer structure and/or in the adhesive overlay.

Non-hybrid pressure-sensitive adhesives are usually supplied and used in solvents like n-heptane and ethyl acetate. The solids content of the pressure-sensitive adhesives is usually between 30% and 80%.

Suitable non-hybrid polymers according to the invention are commercially available e.g. under the brand names BIO-PSAs (pressure sensitive adhesives based on polysiloxanes), Oppanol™ (polyisobutylenes), JSR-SIS (a styrene-isoprene-styrene copolymer) or Duro-Tak™ (acrylic polymers).

Polymers based on polysiloxanes may also be referred to as silicone-based polymers or silicone polymers, or silicones. These polymers based on polysiloxanes are preferably pressure sensitive adhesives based on polysiloxanes. Pressure-sensitive adhesives based on polysiloxanes may also be referred to as silicone-based pressure-sensitive adhesives, or silicone pressure-sensitive adhesives. These pressure-sensitive adhesives provide for suitable tack and for quick bonding to various skin types, including wet skin, suitable adhesive and cohesive qualities, long lasting adhesion to the skin, a high degree of flexibility, a permeability to moisture, and compatibility to many actives and film-substrates. It is possible to provide them with sufficient amine resistance and therefore enhanced stability in the presence of amines. Such pressure-sensitive adhesives are based on a resin-in-polymer concept wherein, by condensation reaction of silanol endblocked polydimethylsiloxane with a silicate resin (also referred to as silica resin), a pressure-sensitive adhesive based on polysiloxane is prepared, wherein for amine stability the residual silanol functionality is additionally capped with trimethylsiloxy groups. The silanol endblocked polydimethylsiloxane content contributes to the viscous component of the visco-elastic behavior, and impacts the wetting and the spreadability properties of the adhesive. The resin acts as a tackifying and reinforcing agent, and participates in the elastic component. The correct balance between silanol endblocked polydimethylsiloxane and resin provides for the correct adhesive properties.

In view of the above, silicone polymers, and in particular silicone-based pressure sensitive adhesives are generally obtainable by polycondensation of silanol endblocked polydimethylsiloxane with a silicate resin. Amine-compatible silicone polymers can be obtained by reacting the silicone polymer with trimethylsilyl (e.g. hexamethyldisilazane) in order to reduce the silanol content of the polymer. As a result, the residual silanol functionality is at least partly, preferably mostly or fully capped with trimethylsiloxy groups.

As indicated above, the tackiness of the at least one silicone polymer may be modified by the resin-to-polymer ratio, i.e. the ratio of the silanol endblocked polydimethylsiloxane to the silicate resin, which is preferably in the range of from 70:30 to 50:50, preferably from 65:35 to 55:45. The tackiness will be increased with increasing amounts of the polymer relative to the resin. High tack silicone polymers preferably have a resin-to-polymer ratio of 55:45, medium tack silicone polymers preferably have a resin-to-polymer ratio of 60:40, and low tack silicone polymers preferably have a resin-to-polymer ratio of 65:35. High tack silicone polymers preferably have a complex viscosity at 0.01 rad/s and 30° C. of $5 \times 10^6$ Poise, medium tack silicone polymers preferably have a complex viscosity at 0.01 rad/s and 30° C. of $5 \times 10^7$ Poise, and low tack silicone polymers preferably have a complex viscosity at 0.01 rad/s and 30° C. of 5×10⁸ Poise. High tack amine-compatible silicone polymers preferably have a complex viscosity at 0.01 rad/s and 30° C. of 5×10⁶ Poise, medium tack amine-compatible silicone polymers preferably have a complex viscosity at 0.01 rad/s and 30° C. of 5×10⁸ Poise, and low tack amine-compatible silicone polymers preferably have a complex viscosity at 0.01 rad/s and 30° C. of 5×10⁹ Poise.

Examples of silicone-based PSA compositions which are commercially available include the standard BIO-PSA series (7-4400, 7-4500 and 7-4600 series), the amine compatible (endcapped) BIO-PSA series (7-4100, 7-4200 and 7-4300 series) manufactured and typically supplied in n-heptane or ethyl acetate by Dow Corning, and the Soft Skin Adhesives series (7-9800) manufactured and typically supplied solvent-free by Dow Corning. For example, BI-PSA 7-4201 is characterized by a solution viscosity at 25° C. and about 70% solids content in heptane of 450 mPa s and a complex viscosity at 0.01 rad/s at 30° C. of 1×10⁸ Poise. BO-PSA 7-4301 has a solution viscosity at 25° C. and about 70% solids content in heptane of 500 mPa s and a complex viscosity at 0.01 rad/s at 30° C. of 5×10⁶ Poise.

The silicone polymers, in particular the pressure-sensitive adhesives based on polysiloxanes, are supplied and used in solvents like n-heptane, ethyl acetate or other volatile silicone fluids. The solids content of the silicone polymers in the solvents is usually between 60 and 80%, preferably between 70 and 80% or between 60 and 70%. The skilled person is aware that the solids content may be modified by adding a suitable amount of solvent.

Silicone polymers, in particular pressure-sensitive adhesives based on polysiloxanes, which are, e.g., available from Dow Corning, may be obtained according to the following scheme:

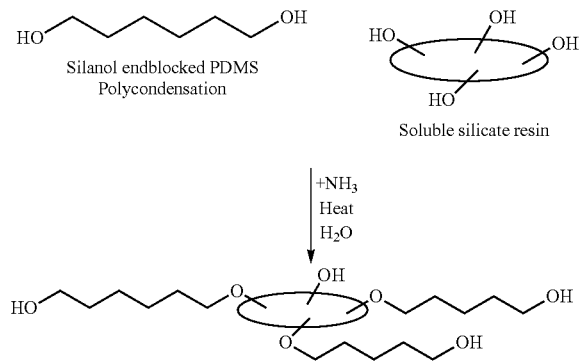

Such silicone polymers are also referred to as standard silicone adhesive and are available from Dow Corning, e.g., under the tradenames BIO-PSA 7-4401, BIO-PSA-7-4501, or BIO-PSA 7-4601, which are provided in the solvent n-heptane (indicated by the code "01"), or under the tradenames BIO-PSA 7-4402, BIO-PSA 7-4502, and BI 7-4602, which are provided in the solvent ethyl acetate (indicated by the code "02"). Typical solids contents in the solvent are in the range of from 60 to 75%. The code "44" indicates a resin-to-polymer ratio of 65:35 resulting in a low tackiness, the code "45" indicates a resin-to-polymer ratio of 60:40 resulting in medium tackiness, the code "46" indicates a resin-to-polymer ratio of 55:45 resulting in high tackiness.

Amine-compatible silicone polymers, in particular amine-compatible pressure-sensitive adhesives based on polysiloxanes, which are, e.g., available from Dow Corning may be obtained according to the following scheme:

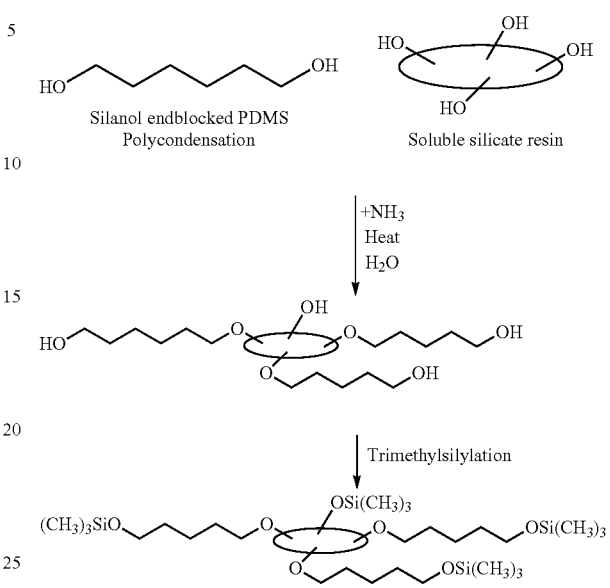

Such amine-compatible silicone polymers are available from Dow Corning, e.g., under the tradenames BIO-PSA 7-4101, BIO-PSA-7-4201, or BIO-PSA 7-4301, which are provided in the solvent n-heptane (indicated by the code "01"), or under the tradenames BIO-PSA 7-4102, BI-PSA 7-4202, and BIO 7-4302, which are provided in the solvent ethyl acetate (indicated by the code "02"). Typical solids contents in the solvent are in the range of from 60 to 75%. The code "41" indicates a resin-to-polymer ratio of 65:35 resulting in a low tackiness, the code "42" indicates a resin-to-polymer ratio of 60:40 resulting in medium tackiness, the code "43" indicates a resin-to-polymer ratio of 55:45 resulting in high tackiness.

The preferred pressure-sensitive adhesives based on polysiloxanes in accordance with the invention are characterized by a solution viscosity at 25° C. and 60% solids content in n-heptane of more than about 150 mPa s, or from about 200 mPa s to about 700 mPa s, preferably as measured using a Brookfield RVT viscometer equipped with a spindle number 5 at 50 rpm. Theses may also be characterized by a complex viscosity at 0.01 rad/s at 30° C. of less than about 1×10⁹ Poise or from about 1×10⁵ to about 9×10⁸ Poise.

Suitable polyisobutylenes according to the invention are available under the tradename Oppanol®. Combinations of high-molecular weight polyisobutylenes (B100/B80) and low-molecular weight polyisobutylenes (B10, B11, B12, B13) may be used. Suitable ratios of low-molecular weight polyisobutylene to high-molecular weight polyisobutylene are in the range of from 100:1 to 1:100, preferably from 95:5 to 40:60, more preferably from 90:10 to 80:20. A preferred example for a polyisobutylene combination is B10/B100 in a ratio of 85/15. Oppanol® B100 has a viscosity average molecular weight $M_v$ of 1,110,000, and a weight average molecular weight $M_w$ of 1,550,000, and an average molecular weight distribution $M_w/M_n$ of 2.9. Oppanol® B10 has a viscosity average molecular weight $M_v$ of 40,000, and a weight average molecular weight $M_w$ of 53,000, and an average molecular weight distribution $M_w/M_n$ of 3.2. In certain embodiments, polybutene may be added to the polyisobutylenes. The solids content of polyisobutylenes in solvents is usually between 30 and 50%, preferably between 35 and 40%. The skilled person is aware that the solids content may be modified by adding a suitable amount of solvent.

Pressure-sensitive adhesives based on acrylates may also be referred to as acrylate-based pressure-sensitive adhesives, or acrylate pressure-sensitive adhesives. Pressure-sensitive adhesives based on acrylates may have a solids content preferably between 30% and 60%. Such acrylate-based pressure-sensitive adhesives may or may not comprise functional groups such as hydroxy groups, carboxylic acid groups, neutralized carboxylic acid groups and mixtures thereof. Thus, the term "functional groups" in particular refers to hydroxy- and carboxylic acid groups, and deprotonated carboxylic acid groups.

Corresponding commercial products are available e.g. from Henkel under the tradename Duro Tak®. Such acrylate-based pressure-sensitive adhesives are based on monomers selected from one or more of acrylic acid, butylacrylate, 2-ethylhexylacrylate, glycidylmethacrylate, 2-hydroxyethylacrylate, methylacrylate, methylmethacrylate, t-octylacrylamide and vinylacetate, and are provided in ethyl acetate, heptanes, n-heptane, hexane, methanol, ethanol, isopropanol, 2,4-pentanedione, toluene or xylene or mixtures thereof.

Specific acrylate-based pressure-sensitive adhesives are available as:
- Duro-Tak™ 387-2287 or Duro-Tak™ 87-2287 (a copolymer based on vinyl acetate, 2-ethylhexyl-acrylate, 2-hydroxyethyl-acrylate and glycidyl-methacrylate provided as a solution in ethyl acetate without cross-linking agent),
- Duro-Tak™ 387-2516 or Duro-Tak™ 87-2516 (a copolymer based on vinyl acetate, 2-ethylhexyl-acrylate, 2-hydroxyethyl-acrylate and glycidyl-methacrylate provided as a solution in ethyl acetate, ethanol, n-heptane and methanol with a titanium cross-linking agent),
- Duro-Tak™ 387-2051 or Duro-Tak™ 87-2051 (a copolymer based on acrylic acid, butylacrylate, 2-ethylhexylacrylate and vinyl acetate, provided as a solution in ethyl acetate and heptane),
- Duro-Tak™ 387-2353 or Duro-Tak™ 87-2353 (a copolymer based on acrylic acid, 2-ethylhexylacrylate, glycidylmethacrylate and methylacrylate, provided as a solution in ethyl acetate and hexane),
- Duro-Tak™ 87-4098 (a copolymer based on 2-ethylhexyl-acrylate and vinyl acetate, provided as a solution in ethyl acetate).

Additional polymers may also be added to enhance cohesion and/or adhesion.

Certain polymers in particular reduce the cold flow and are thus in particular suitable as additional polymer. A polymeric matrix may show a cold flow, since such polymer compositions often exhibit, despite a very high viscosity, the ability to flow very slowly. Thus, during storage, the matrix may flow to a certain extent over the edges of the backing layer. This is a problem with storage stability and can be prevented by the addition of certain polymers. A basic acrylate polymer (e.g. Eudragit® E100) may e.g. be used to reduce the cold flow. Thus, in certain embodiments, the matrix layer composition comprises additionally a basic polymer, in particular an amine-functional acrylate as e.g. Eudragit® E100. Eudragit® E100 is a cationic copolymer based on dimethylaminoethyl methacrylate, butyl methacrylate, and methyl methacrylate with a ratio of 2:1:1. The monomers are randomly distributed along the copolymer chain. Based on SEC method, the weight average molar mass (Mw) of Eudragit® E100 is approximately 47,000 g/mol. Further, polymers such as Plastoid B, acrylic polymers such as Eudragits, Chitosan, celluloses and derivatives thereof, and polystyrene may be useful to increase the dryness of the adhesive (e.g. the matrix layer).

Further Additives

The TTS according to the invention, and in particular the guanfacine-containing layer, comprises at least one additive selected from the group consisting of dispersing agents, permeation enhancers, and solubilizers. Details in this regard are provided above. However, the TTS according to the invention, and in particular the guanfacine-containing layer, may also include further additives or excipients.

In general, additives or excipients are preferably selected from the group consisting of dispersing agents, solubilizers, permeation enhancers, film-forming agents, softeners/plasticizers, tackifiers, substances for skincare, pH regulators, preservatives, stabilizing agents, and fillers. Such additives may be present in the guanfacine-containing layer in an amount of from 0.001% to 15% by weight, e.g. from 0.5 to 10% by weight or from 1 to 10% by weight or from 0.01 to 6% by weight, based on the total weight of the guanfacine-containing layer, and wherein the weight % amounts refer to a single additive.

It should be noted that in pharmaceutical formulations, the formulation components are categorized according to their physicochemical and physiological properties, and in accordance with their function. This means in particular that a substance or a compound falling into one category is not excluded from falling into another category of formulation component. E.g. a certain polymer can be a film-forming agent, but also a tackifier. Some substances may e.g. be a typical softener but at the same time act as a permeation enhancer. The skilled person is able to determine based on his general knowledge in which category or categories of formulation components a certain substance or compound belongs to. In the following, details on the excipients and additives are provided which are, however, not to be understood as being exclusive. Other substances not explicitly listed in the present description may be as well used in accordance with the present invention, and substances and/or compounds explicitly listed for one category of formulation component are not excluded from being used as another formulation component in the sense of the present invention.

In one embodiment, the guanfacine-containing layer comprises a dispersing agent as defined above, preferably a dispersing agent selected from the group consisting of esters of fatty acids with polyols, fatty alcohols, polyethylene glycols having a number average molecular weight of from 300 to 400, polyethylene glycol alkyl ethers. As explained above, the dispersing agent is preferably polyethylene glycol $C_8$-$C_{20}$-alkyl ether having from 2 to 10 EO units, in particular polyoxyethylene (4) lauryl ether. Alternatively or additionally, silicone polyethers may be used as dispersing agents. The dispersing agent is helpful in order to homogeneously disperse the guanfacine within the guanfacine-containing layer, in particular the guanfacine-containing matrix layer, thereby improving the release properties of the TTS.

In one embodiment, the guanfacine-containing layer comprises a solubilizer. The solubilizer preferably improves the dispersibility of the guanfacine in the guanfacine-containing layer and stabilizes the guanfacine-containing layer. Furthermore, the solubilizer may positively influence cohesion.

Preferred solubilizers include, e.g., glycerol-, polyglycerol-, propylene glycol- and polyoxyethylene-esters of medium chain and/or long chain fatty acids, such as glyceryl monolinoleate, medium chain glycerides and medium chain triglycerides, non-ionic solubilizers made by reacting castor oil with ethylene oxide, and any mixtures thereof which may further contain fatty acids or fatty alcohols; cellulose and methylcellulose and derivatives thereof such as hydroxypropylcellulose and hypromellose acetate succinate; various cyclodextrins and derivatives thereof; non-ionic tri-block copolymers having a central hydrophobic chain of polyoxypropylene flanked by two hydrophilic chains of polyoxyethylene known as poloxamers; water-soluble derivatives of vitamin E; pharmaceutical graded or agglomerated spherical isomalt; a polyethylene glycol, polyvinyl acetate and polyvinylcaprolactame-based graft copolymer, also abbreviated as PVAc-PVCap-PEG and known as Soluplus®; vinylpyrrolidone-vinyl acetate copolymers such as Kollidon® VA64; purified grades of naturally derived castor oil, of polyethylene glycol 400, of polyoxyethylene sorbitan monooleate (such as polysorbate 80) or of propylene glycols; diethylene glycol monoethyl ether; glucono-delta-lactone; maize and potato starch; as well as any of the below mentioned soluble polyvinylpyrrolidones, but also insoluble/cross-linked polyvinylpyrrolidones such as crospovidones.

However, also the permeation enhancers mentioned below can act as solubilizers. Furthermore, also the film-forming agents described below may act at the same time as solubilizers and vice versa.

In one embodiment, the guanfacine-containing layer comprises a permeation enhancer. Preferences in this regard are provided above. Permeation enhancers are substances, which influence the barrier properties of the stratum corneum in the sense of increasing the active agent permeability. Some examples of permeation enhancers are polyhydric alcohols such as dipropylene glycol, propylene glycol, and polyethylene glycol; oils such as olive oil, squalene, and lanolin; fatty ethers such as cetyl ether and oleyl ether; fatty acid esters such as isopropyl myristate; urea and urea derivatives such as allantoin; polar solvents such as dimethyldecylphosphoxide, methylcetylsulfoxide, dimethylaurylamine, dodecyl pyrrolidone, isosorbitol, dimethylacetonide, dimethylsulfoxide, decylmethylsulfoxide, and dimethylformamide; salicylic acid; amino acids; benzyl nicotinate; and higher molecular weight aliphatic surfactants such as lauryl sulfate salts. Other agents include oleic and linoleic acids, ascorbic acid, panthenol, butylated hydroxytoluene, tocopherol, tocopheryl acetate, tocopheryl linoleate, propyl oleate, and isopropyl palmitate. If the guanfacine-containing layer comprises a permeation enhancer, the permeation enhancer is preferably selected from the group consisting of diethylene glycol monoethyl ether (transcutol), oleic acid, levulinic acid, caprylic/capric triglycerides, diisopropyl adipate, isopropyl myristate, isopropyl palmitate, lauryl lactate, triacetin, dimethylroylene urea, and oleyl alcohol, and is preferably oleyl alcohol.

In one embodiment, the guanfacine-containing layer further comprises a film-forming agent. It is to be understood that the above mentioned solubilizers, such as Soluplus®, may also act as film forming agents and control cohesion. Suitable examples of further film-forming agents include polyvinylpyrrolidone, vinyl acetate/vinylpyrrolidone copolymers and cellulose derivatives, preferably polyvinylpyrrolidone, more preferably soluble polyvinylpyrrolidone.

If the guanfacine-containing layer is required to have self-adhesive properties and one or more polymers is/are selected, which does/do not provide sufficient self-adhesive properties, a tackifier is added. Preferred tackifiers include Miglyol, which is a liquid wax ester based on long-chain, unsaturated, even-numbered fatty acids and long-chain, unsaturated, even-numbered fatty alcohols of vegetable origin, and polyethylene glycols. In particular, the tackifier may be selected from polyvinylpyrrolidone (which, due to its ability to absorb water, is able to maintain the adhesive properties of the matrix layer and thus can be regarded as a tackifier in a broad sense), triglycerides, polyethylene glycols, dipropylene glycol, resins, resin esters, terpenes and derivatives thereof, ethylene vinyl acetate adhesives, dimethylpolysiloxanes and polybutenes, preferably polyvinylpyrrolidone and more preferably soluble polyvinylpyrrolidone. Preferably, the tackifier may be selected from polyvinylpyrrolidone, triglycerides, dipropylene glycol, resins, resin esters, terpenes and derivatives thereof, ethylene vinyl acetate adhesives, dimethylpolysiloxanes and polybutenes, preferably polyvinylpyrrolidone and more preferably soluble polyvinylpyrrolidone.

The term "soluble polyvinylpyrrolidone" refers to polyvinylpyrrolidone, also known as povidone, which is soluble with more than 10% in at least ethanol, preferably also in water, diethylene glycol, methanol, n-propanol, 2 propanol, n-butanol, chloroform, methylene chloride, 2-pyrrolidone, macrogol 400, 1,2 propylene glycol, 1,4 butanediol, glycerol, triethanolamine, propionic acid and acetic acid. Examples of polyvinylpyrrolidones which are commercially available include Kollidon 12 PF, Kollidon® 17 PF, Kollidon® 25, Kollidon® 30 and Kollidon® 90 F supplied by BASF, or povidone K90F. The different grades of Kollidon® are defined in terms of the K-Value reflecting the average molecular weight of the polyvinylpyrrolidone grades. Kollidon 12 PF is characterized by a K-Value range of 10.2 to 13.8, corresponding to a nominal K-Value of 12. Kollidon® 17 PF is characterized by a K-Value range of 15.3 to 18.4, corresponding to a nominal K-Value of 17. Kollidon® 25 is characterized by a K-Value range of 22.5 to 27.0, corresponding to a nominal K-Value of 25, Kollidon® 30 is characterized by a K-Value range of 27.0 to 32.4, corresponding to a nominal K-Value of 30. Kollidon® 90 F is characterized by a K-Value range of 81.0 to 97.2, corresponding to a nominal K-Value of 90. Preferred Kollidon® grades are Kollidon® 12 PF, Kollidon 30 and Kollidon® 90 F. Within the meaning of this invention, the term "K-Value" refers to a value calculated from the relative viscosity of polyvinylpyrrolidone in water according to the European Pharmacopoeia (Ph. Eur.) and USP monographs for "Povidone".

In one embodiment, the guanfacine-containing layer further comprises a softener/plasticizer. Exemplary softeners/plasticizers include linear or branched, saturated or unsaturated alcohols having 6 to 20 carbon atoms, triglycerides and polyethylene glycols.

In one embodiment, the guanfacine-containing layer further comprises a stabilizing agent. Stabilizing agents include tocopherol and ester derivatives thereof and ascorbic acid and ester derivatives thereof. Further stabilizing agents include sodium metabisulfite, ascorbyl esters of fatty acids such as ascorbyl palmitate, ascorbic acid, butylated hydroxytoluene, tocopherol, tocopheryl acetate and tocopheryl linoleate.

In one embodiment, the guanfacine-containing layer further comprises a pH regulator. Suitable pH regulators include mild acids and bases including amine derivatives, inorganic alkali derivatives, and polymers with basic or acidic functionality.

In one embodiment, the guanfacine-containing layer further comprises a preservative. Suitable preservatives include parabens, formaldehyde releasers, isothiazolinones, phenoxyethanol, and organic acids such as benzoic acid, sorbic acid, levulinic acid and anisic acid.

In one embodiment, the guanfacine-containing layer further comprises a substance for skincare. Such substances may be used to avoid or reduce skin irritation as detectable by the dermal response score. Suitable substances for skincare include sterol compounds such as cholesterol, dexpanthenol, alpha-bisabolol, and antihistamines.

In one embodiment, the guanfacine-containing layer further comprises a filler. Fillers such as silica gels, titanium dioxide and zinc oxide may be used in conjunction with the polymer in order to influence certain physical parameters, such as cohesion and bond strength, in the desired way.

Release Characteristics

The TTS in accordance with the invention are designed for transdermally administering guanfacine to the systemic circulation for a predefined extended period of time, preferably for at least 24 hours, more preferably at least 72 hours, in particular for about 84 hours.

In one embodiment, the TTS according to the invention provides by transdermal delivery at steady state a mean plasma concentration of guanfacine of from 1 to 20 ng/ml, preferably from 1 to 15 ng/ml, more preferably 1 to 10 ng/ml.

Preferably, the TTS provides therapeutically effective plasma concentrations of guanfacine within less than 8 hours, preferably less than 6 hours, more preferably less than 4 hours after application of the TTS to the skin. Furthermore, the therapeutically effective plasma concentrations are preferably maintained over the whole administration period of at least 24 hours, preferably at least 72 hours, more preferably about 84 hours.

In one embodiment, the TTS according to the invention provides an $AUC_{0-24\ h}$ of 10 to 600 ng*h/ml, preferably of 20 to 400 ng*h/ml. In another embodiment, the TTS according to the invention provides an $AUC_{0-72\ h}$ of 30 to 1800 ng*h/ml, preferably of 60 to 1200 ng*h/ml. In another embodiment, the TTS according to the invention provides an $AUC_{0-84\ h}$ of 35 to 2100 ng*h/ml, preferably of 70 to 1400 ng*h/ml. It is to be understood that the AUC values preferably refer to the AUC values obtained at steady state.

In one embodiment, the TTS according to the invention provides a $C_{max}$ to $C_{84}$ ratio of less than 3.5. In another embodiment, the TTS according to the invention provides a $C_{max}$ to $C_{72}$ ratio of less than 3.0. In another embodiment, the TTS according to the invention provides a $C_{max}$ to $C_{24}$ ratio of less than 2.0. These ratios indicate a flat blood plasma curve, which is advantageous in terms of a continuous treatment of the patient.

In one embodiment, the TTS according to the invention provides a skin permeation rate of guanfacine as measured in a Franz diffusion cell with dermatomed human skin of
0.01 μg/(cm²*h) to 8 μg/(cm²*h) in the first 24 hours,
0.05 μg/(cm²*h) to 10 μg/(cm²*h) from hour 24 to hour 72.

In one embodiment, the TTS according to the invention provides a skin permeation rate of guanfacine as measured in a Franz diffusion cell with dermatomed human skin of 0.01 mg/cm² to 0.7 mg/cm², preferably 0.05 mg/cm² to 0.6 mg/cm², more preferably 0.15 to 0.3 mg/cm² over a time period of 72 hours.

In view of the above, the present invention relates in one aspect also to a transdermal therapeutic system for the transdermal administration of guanfacine comprising a guanfacine-containing layer structure, wherein the transdermal therapeutic system provides by transdermal delivery one or more pharmacokinetic parameter(s) selected from the group consisting of
an $AUC_{0-24}$ from 10 to 600 (ng/mL) h,
an $AUC_{0-72}$ from 30 to 1800 (ng/mL) h,
an $AUC_{0-84}$ from 35 to 2100 (ng/mL) h,
a $C_{max}$ to $C_{24}$ ratio of less than 2.0,
a $C_{max}$ to $C_{72}$ ratio of less than 3.0, and
a $C_{max}$ to $C_{84}$ ratio of less than 3.5.

In a preferred embodiment of the present invention relates to a transdermal therapeutic system for the transdermal administration of guanfacine comprising a guanfacine-containing layer structure,
wherein the transdermal therapeutic system provides by transdermal delivery one or more pharmacokinetic parameter(s) selected from the group consisting of
an $AUC_{0-24}$ from 20 to 400 (ng/mL) h,
an $AUC_{0-72}$ from 60 to 1200 (ng/mL) h,
an $AUC_{0-84}$ from 70 to 1400 (ng/mL) h,
a $C_{max}$ to $C_{24}$ ratio of less than 1.5,
a $C_{max}$ to $C_{72}$ ratio of less than 2.5, and
a $C_{max}$ to $C_{84}$ ratio of less than 3.0.

Method of Treatment/Medical Use

In one embodiment of the present invention, the TTS according to the invention are suitable for use in a method of treating a human patient, preferably a patient at the age of from 6 to 17. In particular, the TTS according to the invention are suitable for use in a method of treating hypertension or attention deficit hyperactivity disorder (ADHD) and/or as adjunctive therapy to stimulant medications in a human patient, preferably in a human patient at the age of from 6 to 17.

In a preferred embodiment in connection with the above medical use, the TTS is applied to the skin of the patient for at least 24 hours, preferably at least 72 hours, more preferably about 84 hours.

In one embodiment, the present invention relates to a method of treating a human patient, preferably a human patient at the age of from 6 to 17, by applying a transdermal therapeutic system as defined in any one of items 1 to 37 to the skin of the patient. In particular, the present invention relates to a method of treating hypertension or attention deficit hyperactivity disorder (ADHD) in a human patient, preferably a human patient at the age of from 6 to 17, by applying a transdermal therapeutic system according to the invention to the skin of the patient.

In a preferred embodiment of the above methods of treatment, the transdermal therapeutic system is applied to the skin of the patient for at least 24 hours, preferably at least 72 hours, more preferably about 84 hours.

In view of the above, the present invention relates in one aspect to a transdermal therapeutic system comprising guanfacine for use in a method of treating a human patient, preferably a human patient at the age of from 6 to 17, by transdermal administration of guanfacine, wherein the transdermal therapeutic system is applied to the skin of a patient for at least 24 hours, preferably at least 72 hours, more preferably about 84 hours. In a preferred embodiment, the transdermal therapeutic system is for use in a method of treating hypertension or attention deficit hyperactivity disorder (ADHD) and/or as adjunctive therapy to stimulant medications in a human patient. In a more preferred embodiment, the transdermal therapeutic system is a transdermal therapeutic system according to the invention, in particular a transdermal therapeutic system providing one or more of the pharmacokinetic parameter(s) selected from the group consisting of an $AUC_{0-24}$ from 10 to 600 (ng/mL) h,
an $AUC_{0-72}$ from 30 to 1800 (ng/mL) h,
an $AUC_{0-84}$ from 35 to 2100 (ng/mL) h,
a $C_{max}$ to $C_{24}$ ratio of less than 2.0,
a $C_{max}$ to $C_{72}$ ratio of less than 3.0, and
a $C_{max}$ to $C_{84}$ ratio of less than 3.5;

and preferably selected from the group consisting of an $AUC_{0-24}$ from 20 to 400 (ng/mL) h,
an $AUC_{0-72}$ from 60 to 1200 (ng/mL) h,
an $AUC_{0-84}$ from 70 to 1400 (ng/mL) h,
a $C_{max}$ to $C_{24}$ ratio of less than 1.5,
a $C_{max}$ to $C_{72}$ ratio of less than 2.5, and
a $C_{max}$ to $C_{84}$ ratio of less than 3.0.

In another aspect, the present invention relates to guanfacine for use in a method of treating a human patient, preferably a human patient at the age of from 6 to 17, by transdermal administration of guanfacine with a transdermal therapeutic system, wherein the transdermal therapeutic system is applied to the skin of a patient for at least 24 hours, preferably at least 72 hours, more preferably about 84 hours. In a preferred embodiment, the guanfacine is for use in a method of treating hypertension or attention deficit hyperactivity disorder (ADHD) and/or as adjunctive therapy to stimulant medications in a human patient. In a more preferred embodiment, the transdermal therapeutic system is a transdermal therapeutic system according to the invention, in particular a transdermal therapeutic system providing one or more of the pharmacokinetic parameter(s) selected from the group consisting of an $AUC_{0-24}$ from 10 to 600 (ng/mL) h,
an $AUC_{0-72}$ from 30 to 1800 (ng/mL) h,
an $AUC_{0-84}$ from 35 to 2100 (ng/mL) h,
a $C_{max}$ to $C_{24}$ ratio of less than 2.0,
a $C_{max}$ to $C_{72}$ ratio of less than 3.0, and
a $C_{max}$ to $C_{84}$ ratio of less than 3.5;

and preferably selected from the group consisting of an $AUC_{0-24}$ from 20 to 400 (ng/mL) h,
an $AUC_{0-72}$ from 60 to 1200 (ng/mL) h,
an $AUC_{0-84}$ from 70 to 1400 (ng/mL) h,
a $C_{max}$ to $C_{24}$ ratio of less than 1.5,
a $C_{max}$ to $C_{72}$ ratio of less than 2.5, and
a $C_{max}$ to $C_{84}$ ratio of less than 3.0.

In another aspect, the present invention relates to a method of treating a human patient, preferably a human patient at the age of from 6 to 17, by transdermal administration of guanfacine, wherein the transdermal therapeutic system is applied to the skin of a patient for at least 24 hours, preferably at least 72 hours, more preferably about 84 hours. In a preferred embodiment, the method is for treating hypertension or attention deficit hyperactivity disorder (ADHD) and/or as adjunctive therapy to stimulant medications in a human patient. In a more preferred embodiment, the transdermal therapeutic system is a transdermal therapeutic system according to the invention, in particular a transdermal therapeutic system providing one or more of the pharmacokinetic parameter(s) selected from the group consisting of an $AUC_{0-24}$ from 10 to 600 (ng/mL) h,
an $AUC_{0-72}$ from 30 to 1800 (ng/mL) h,
an $AUC_{0-84}$ from 35 to 2100 (ng/mL) h,
a $C_{max}$ to $C_{24}$ ratio of less than 2.0,
a $C_{max}$ to $C_{72}$ ratio of less than 3.0, and
a $C_{max}$ to $C_{84}$ ratio of less than 3.5;

and preferably selected from the group consisting of an $AUC_{0-24}$ from 20 to 400 (ng/mL) h,
an $AUC_{0-72}$ from 60 to 1200 (ng/mL) h,
an $AUC_{0-84}$ from 70 to 1400 (ng/mL) h,
a $C_{max}$ to $C_{24}$ ratio of less than 1.5,
a $C_{max}$ to $C_{72}$ ratio of less than 2.5, and
a $C_{max}$ to $C_{84}$ ratio of less than 3.0.

In connection with the above uses and methods of treatment, the TTS according to the invention is preferably applied to at least one body surface on the subject selected from the upper outer art, upper chest, upper back or the side of the chest for the defined dosing intervals.

The preferred application time of a TTS according to the invention is at least 24 hours (1 day), preferably at least 72 hours (3 days), more preferably about 84 hours (3.5 days). After this time, the TTS may be removed, and optionally a new TTS may be applied, so as to allow an around-the-clock treatment.

Process of Manufacture

The invention further relates to a process for manufacturing a guanfacine-containing layer, preferably a guanfacine-containing matrix layer, for use in a transdermal therapeutic system.

In accordance with the invention, the process for manufacturing a guanfacine-containing layer for use in a transdermal therapeutic system according to the invention comprises the steps of:

1) combining at least the components
   i) guanfacine;
   ii) the at least one polymer; and
   iii) the at least one additive selected from dispersing agents, permeation enhancers, and solubilizers;
   to obtain a coating composition;
2) coating the coating composition onto a backing layer or a release liner to obtain a coated coating composition; and
3) drying the coated coating composition to form the guanfacine-containing layer.

In step 1) of the above process of manufacture, the guanfacine is preferably dispersed in the polymer to obtain a homogenous coating composition.

Preferably, a solvent is added in step 1) of the process, and/or a solvent is present because the one or more polymer(s) are provided in the form of a solution. The solvent is preferably selected from alcoholic solvents, in particular methanol, ethanol, isopropanol and mixtures thereof, and from non-alcoholic solvents, in particular ethyl acetate, hexane, heptane, petroleum ether, toluene, and mixtures thereof. Preferably, the solvent comprises ethyl acetate or n-heptane.

In a preferred embodiment, the at least one polymer is provided as a solution with a solids content of from 40 to 60% by weight.

In step 2) of the process the coating composition is applied to a backing layer or a release liner. As a result a coated coating composition, i.e. a coating composition being coated on a backing layer or a release liner is obtained.

After the guanfacine-containing layer is formed in step 3), the process may thus further comprise a step, wherein a release liner or backing layer is applied to the other side of the guanfacine-containing layer.

In step 3) of the above process of manufacture, drying is performed preferably at a temperature of from 20 to 90° C., more preferably from 40 to 70° C. Drying may preferably take at least 1 hour, preferably at least 8 hours, e.g. one day.

EXAMPLES

The present invention will now be more fully described with reference to the accompanying examples. It should be understood, however, that the following description is illustrative only and should not be taken in any way as a restriction of the invention. Numerical values provided in the examples regarding the amount of ingredients in the composition or the area weight may vary slightly due to manufacturing variability.

Example 1A-D

Coating Composition

The formulations of the guanfacine-containing coating compositions of Examples 1a-d are summarized in Table 1.1a and 1.1b below. The %-values refer to the amounts (Amt) in % by weight.

TABLE 1.1a

| Ingredient (Trade Name) | Ex. 1a | | Ex. 1b | |
|---|---|---|---|---|
| | Amt [g] | Solids [%] | Amt [g] | Solids [%] |
| Guanfacine base | 10.81 | 11.98 | 10.8 | 8.00 |
| Silicone acrylic hybrid pressure sensitive adhesive in ethyl acetate Solids content of 50% by weight (PSA SilAc 7-6102 from Dow Corning Healthcare) | 81.94 | 45.58 | 130.5 | 48.52 |
| Silicone acrylic hybrid pressure sensitive adhesive in ethyl acetate Solids content of 50% by weight (PSA SilAc 7-6302 from Dow Corning Healthcare) | 54.48 | 30.42 | 86.97 | 32.47 |
| Polyvinyl caprolactam-polyvinyl acetate-polyethylene graft copolymer (Soluplus) | 1.82 | 2.02 | 2.72 | 2.01 |
| Olcylalcohol | 5.41 | 5.99 | 12.15 | 9.00 |
| Polyoxyethylene (4) lauryl ether (Brij L4) | 3.62 | 4.01 | — | — |
| Total | 158.08 | 100.0 | 243.14 | 100.0 |
| Area Weight [g/m²] | 100 | | 158 | |
| Loading API [µg/cm²] | 1198 | | 1264 | |

TABLE 1.1b

| Ingredient (Trade Name) | Ex. 1c | | Ex. 1d | |
|---|---|---|---|---|
| | Amt [g] | Solids [%] | Amt [g] | Solids [%] |
| Guanfacine base | 3.56 | 3.95 | 10.79 | 8.00 |
| Silicone acrylic hybrid pressure sensitive adhesive in ethyl acetate Solids content of 50% by weight (PSA SilAc 7-6102 from Dow Corning Healthcare) | 92.51 | 51.59 | 120.52 | 44.79 |
| Silicone acrylic hybrid pressure sensitive adhesive in ethyl acetate Solids content of 50% by weight (PSA SilAc 7-6302 from Dow Corning Healthcare) | 61.41 | 34.38 | 80.21 | 29.93 |

TABLE 1.1b-continued

| Ingredient (Trade Name) | Ex. 1c | | Ex. 1d | |
|---|---|---|---|---|
| | Amt [g] | Solids [%] | Amt [g] | Solids [%] |
| Acrylate-vinylacetate adhesive in ethyl acetate/ethanol/heptane/methanol Solids content of 42% by weight (DURO-TAK ® 387-2516) | — | — | 26.63 | 8.28 |
| Oleylalcohol | 5.44 | 6.04 | 12.15 | 9.00 |
| Polyoxyethylene (4) lauryl ether (Brij L4) | 3.63 | 4.03 | — | — |
| Total | 166.5 | 100 | 250.3 | 100.0 |
| Area Weight [g/m²] | 97 | | 155 | |
| Loading API [µg/cm²] | 383 | | 1240 | |

Preparation of the Coating Composition

Drug substance and enhancers used were dispersed in the solvent ethyl acetate and ultrasonic treated for approx. 10 min. The adhesives were added. These two steps can be done also in reverse order. With a dissolver stirrer the mixture was homogenized at 2000 rpm for 2-4 minutes. The mass was stirred again for 30 minutes at 1500 rpm.

In case of compositions 1a and 1b Soluplus was added after the mixture was homogenized at 2000 rpm for 2 minutes. The mass was stirred for additional 2 min at 2000 rpm and further homogenized at 1500 rpm for 30 min.

Coating of the Coating Composition

The resulting guanfacine-containing coating composition was coated on a polyethylene terephthalate film (Scotchpak 9755, which may function as a release liner) using for example a film applicator from the company Erichsen according to the solid content of the mixture under consideration of the desired coating dry weight and dried at approx. 50° C. for approx. 10 min. Depending on the target area weight the corresponding film applicator gap is between 150-350 µm.

The coating thickness was chosen such that removal of the solution results in an area weight of the guanfacine-containing layer of approx. 100 (Ex. 1a), 158 (Ex. 1b), 97 (Ex. 1c), 155 (Ex. 1d) g/m². The dried film was then laminated with a backing layer (PET 15 µm tsp) to provide a guanfacine-containing self-adhesive layer structure.

Preparation of the TTS (Concerning all Examples)

The individual systems (TTS) were then punched out from the guanfacine-containing self-adhesive layer structure obtained as described above. Then, the TTS were sealed into pouches of the primary packaging material.

Measurement of Skin Permeation

The permeated amount of TTS prepared according to Examples 1a-d was determined by experiments in accordance with the OECD Guideline (adopted Apr. 13, 2004) carried out with a 10.0 mL Franz diffusion cell. Split thickness human skin from cosmetic surgeries (e.g., female abdomen, date of birth 1985) was used. A dermatome was used to prepare skin to a thickness of 500 µm, with an intact epidermis for all TTS. Die-cuts with an area of release of 1.191 cm² were punched from the TTS. The guanfacine permeated amount in the receptor medium of the Franz diffusion cell (phosphate buffer solution pH 5.5 with 0.1% sodium azide as bacteriological agent) at a temperature of 32±1° C. was measured and the corresponding cumulative permeated amount was calculated.

The results are shown in Table 1.2a and Table 1.2b and FIG. 1.

TABLE 1.2a

Cumulative permeated amount with SD [µg/cm$^2$]

| Elapsed time [h] | Ex. 1a (n = 3) Amount | SD | Ex. 1b (n = 3) Amount | SD | Ex. 1e (n = 3) Amount | SD |
|---|---|---|---|---|---|---|
| 8 | 3.34 | 1.28 | 0.39 | 0.45 | 3.91 | 1.28 |
| 24 | 76.14 | 11.3 | 25.52 | 8.86 | 53.58 | 4.43 |
| 32 | 134.34 | 15.86 | 44.82 | 13.2 | 83.28 | 6.59 |
| 48 | 248.01 | 22.19 | 83.12 | 20.15 | 134.51 | 9.44 |
| 72 | 404.67 | 24.48 | 139.22 | 28.59 | 203.74 | 12.85 |

TABLE 1.2b

Cumulative permeated amount with SD [µg/cm$^2$]

| Elapsed time [h] | Ex. 1d (n = 3) Amount | SD |
|---|---|---|
| 8 | 0.09 | 0.02 |
| 24 | 15.82 | 0.88 |
| 32 | 30.46 | 2.55 |
| 48 | 60.72 | 5.92 |
| 72 | 106.26 | 11.49 |

Example 2A-E

Coating Composition

The formulations of the guanfacine-containing coating compositions of Examples 2a-e are summarized in Table 2.1a and 2.1b below. The %-values refer to the amounts in % by weight.

TABLE 2.1a

| Ingredient (Trade Name) | Ex. 2a Amt [g] | Solids [%] | Ex. 2b Amt [g] | Solids [%] | Ex. 2c Amt [g] | Solids [%] |
|---|---|---|---|---|---|---|
| Guanfacine base | 2.15 | 11.90 | 2.15 | 5.97 | 1.12 | 6.22 |
| Silicone acrylic hybrid pressure sensitive adhesive in ethyl acetate Solids content of 50% by weight (PSA SilAc 7-6102 from Dow Corning Healthcare) | 26.4 | 73.80 | 58.28 | 81.74 | 29.79 | 83.54 |
| Silicone acrylic hybrid pressure sensitive adhesive in ethyl acetate Solids content of 50% by weight (PSA SilAc 7-6302 from Dow Corning Healthcare) | 1.38 | 3.84 | 3.05 | 4.26 | 1.54 | 4.30 |
| Oleylalcohol | 0.72 | 3.99 | 1.45 | 4.03 | 0.71 | 3.94 |
| Polyoxyethylene (4) lauryl ether (Brij L4) | 0.76 | 4.21 | 1.44 | 4.00 | 0.36 | 2.00 |
| Polyvinyl caprolactam-polyvinyl acetate-polyethylene graft copolymer (Soluplus) | 0.41 | 2.27 | — | — | — | — |
| Total | 31.82 | 100.0 | 66.37 | 100.0 | 33.52 | 100.0 |
| Area Weight [g/m$^2$] | 76 | | 74 | | 101 | |
| Loading API [µg/cm$^2$] | 904 | | 442 | | 628 | |

TABLE 2.1b

| Ingredient (Trade Name) | Ex. 2d Amt [g] | Solids [%] | Ex. 2e Amt [g] | Solids [%] |
|---|---|---|---|---|
| Guanfacine base | 1.06 | 5.84 | 1.08 | 5.99 |
| Silicone acrylic hybrid pressure sensitive adhesive in ethyl acetate Solids content of 50% by weight (PSA SilAc 7-6102 from Dow Corning Healthcare) | 30.53 | 84.98 | 29.85 | 83.61 |
| Silicone acrylic hybrid pressure sensitive adhesive in ethyl acetate Solids content of 50% by weight (PSA SilAc 7-6302 from Dow Corning Healthcare) | 1.68 | 4.66 | 1.58 | 4.41 |
| Oleylalcohol | 0.43 | 2.37 | 0.35 | 1.94 |
| Polyoxyethylene (4) lauryl ether (Brij L4) | 0.39 | 2.15 | 0.73 | 4.05 |
| Total | 34.09 | 100.0 | 33.59 | 100.0 |
| Area Weight [g/m$^2$] | 95 | | 98 | |
| Loading API [µg/cm$^2$] | 555 | | 587 | |

Preparation of the Coating Composition

Drug substance and enhancers used were dispersed in the solvent ethyl acetate and ultrasonic treated for approx. 5 minutes. The adhesives were added. These two steps can be done also in reverse order. With a stirrer the mixture was homogenized at 2000 rpm for 5 minutes. The mass was stirred again for 10-15 minutes at 1000-1500 rpm.

In case of composition 2a Soluplus was added after the mixture was homogenized at 2000 rpm for 5 minutes. The mass was stirred for additional 2 min at 2000 rpm and further homogenized at 1500 rpm for 30 min.

Coating of the Coating Composition

See Example 1a-d for the coating process. The coating thickness gave an area weight of the guanfacine-containing layer of 76 (Ex. 2a), 74 (Ex. 2b), 101 (Ex. 2c), 95 (Ex. 2d) and 98 (Ex. 2e) g/m$^2$. The dried film was laminated with a backing layer (e.g. PET 15 µm tsp) to provide a guanfacine-containing self-adhesive layer structure.

Preparation of the TTS
See Example 1.

Measurement of Skin Permeation

The permeated amount of TTS prepared according to Examples 2a-e was determined as described for Examples 1a-d above. Die-cuts with an area of release of 1.188 cm² were punched from the TTS.

Figure 2:
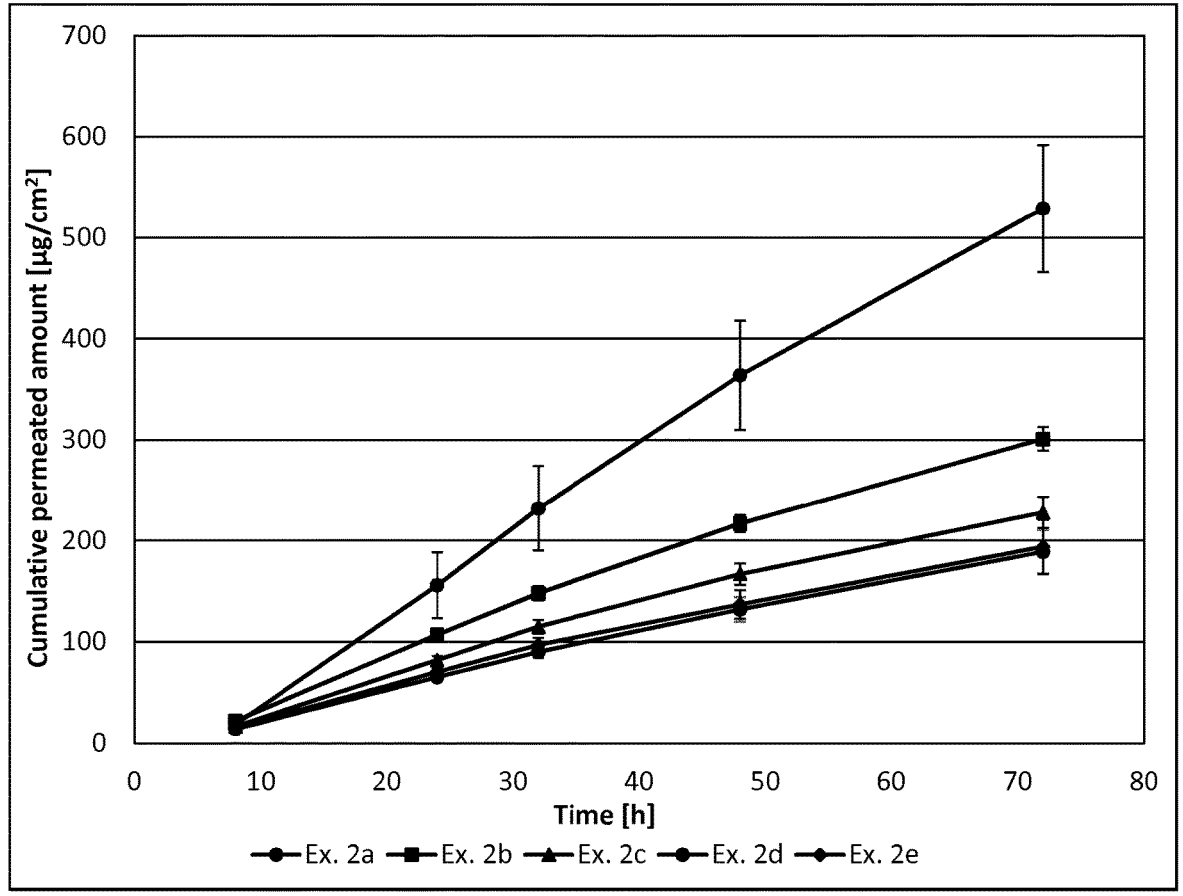
FIG. 2 depicts the guanfacine permeated amount of TTS prepared according to Examples 2a-e.

The results are shown in Table 2.2a and 2.2b and FIG. 2.

TABLE 2.2a

Cumulative permeated amount with SD [µg/cm²]

| Elapsed time [h] | Ex. 2a (n = 3) Amount | SD | Ex. 2b (n = 3) Amount | SD | Ex. 2c (n = 3) Amount | SD |
|---|---|---|---|---|---|---|
| 8 | 18.50 | 5.43 | 21.77 | 2.84 | 16.37 | 0.29 |
| 24 | 155.83 | 32.64 | 106.60 | 6.22 | 82.17 | 3.62 |
| 32 | 232.37 | 41.91 | 148.07 | 7.01 | 115.17 | 6.73 |
| 48 | 363.70 | 53.79 | 216.97 | 8.75 | 166.60 | 10.66 |
| 72 | 529.03 | 63.04 | 301.03 | 11.82 | 228.33 | 15.69 |

TABLE 2.2b

Cumulative permeated amount with SD [µg/cm²]

| Elapsed time [h] | Ex. 2d (n = 3) Amount | SD | Ex. 2e (n = 3) Amount | SD |
|---|---|---|---|---|
| 8 | 13.83 | 3.07 | 14.90 | 2.94 |
| 24 | 65.17 | 3.21 | 70.43 | 4.05 |
| 32 | 90.10 | 6.02 | 97.03 | 7.40 |
| 48 | 132.43 | 12.10 | 137.23 | 14.02 |
| 72 | 188.30 | 21.54 | 194.00 | 26.96 |

Example 3A-3F

Coating Composition

The formulations of the guanfacine-containing coating compositions of Examples 3a-f are summarized in Table 3.1a, 3.1b and 3.1c below. The %-values refer to the amounts in % by weight.

TABLE 3.1a

| Ingredient (Trade Name) | Ex. 3a Amt [g] | Solids [%] | Ex. 3b Amt [g] | Solids [%] | Ex. 3c Amt [g] | Solids [%] |
|---|---|---|---|---|---|---|
| Guanfacine base | 1.21 | 8.04 | 0.29 | 1.92 | 0.76 | 4.17 |
| Silicone acrylic hybrid pressure sensitive adhesive in ethyl acetate Solids content of 50% by weight (PSA SilAc 7-6102 from Dow Corning Healthcare) | 23.03 | 76.67 | 25.01 | 82.82 | — | — |
| Silicone acrylic hybrid pressure sensitive adhesive in ethyl acetate Solids content of 50% by weight (PSA SilAc 7-6302 from Dow Corning Healthcare) | — | — | — | — | 33.56 | 93.74 |
| Oleylalcohol | 1.36 | 9.04 | 1.37 | 9.05 | — | — |
| 2-(2-Ethoxyethoxy)ethanol | 0.94 | 6.25 | 0.94 | 6.21 | — | — |
| Polyoxyethylene (4) lauryl ether (Brij L4) | — | — | — | — | 0.38 | 2.09 |
| Total | 26.54 | 100.0 | 27.61 | 100.0 | 34.7 | 100.0 |
| Area Weight [g/m²] | 151 | | 150 | | 153 | |
| Loading API [µg/cm²] | 1214 | | 288 | | 638 | |

TABLE 3.1b

| Ingredient (Trade Name) | Ex. 3d Amt [g] | Solids [%] | Ex. 3e Amt [g] | Solids [%] |
|---|---|---|---|---|
| Guanfacine base | 0.35 | 1.94 | 0.77 | 4.22 |
| Silicone acrylic hybrid pressure sensitive adhesive in ethyl acetate Solids content of 50% by weight (PSA SilAc 7-6302 from Dow Corning Healthcare) | 31.15 | 87.86 | 33.68 | 93.97 |
| Poly(butylmethacrylate-co-(2-dimethylaminoethyl)methacrylate-co-methyl methacrylate) (Eudragit E100) | 1.84 | 10.20 | — | — |
| Polyoxyethylene (10) oleyl ether (Brij O10) | — | — | 0.33 | 1.81 |
| Total | 33.34 | 100.0 | 34.78 | 100.0 |
| Area Weight [g/m²] | 143 | | 143 | |
| Loading API [µg/cm²] | 277 | | 604 | |

TABLE 3.1c

| Ingredient (Trade Name) | Ex. 3f Amt [g] | Solids [%] |
|---|---|---|
| Guanfacine base | 1.01 | 4.03 |
| Silicone acrylic hybrid pressure sensitive adhesive in ethyl acetate Solids content of 50% by weight (PSA SilAc 7-6102 from Dow Corning Healthcare) | 30.33 | 60.70 |
| Acrylate-vinylacetate adhesive in ethyl acetate/ethanol/heptane/methanol Solids content of 42% by weight (DURO-TAK ® 387-2516) | 12.04 | 20.25 |
| Oleylalcohol | 2.24 | 8.95 |
| 2-(2-Ethoxyethoxy)ethanol | 1.52 | 6.07 |
| Total | 47.14 | 100.0 |
| Area Weight [g/m²] | 143 | |
| Loading API [µg/cm²] | 576 | |

Preparation of the Coating Composition

In case of compositions 3a and 3b, drug substance and enhancers used were dispersed and ultrasonic treated for 5 minutes. The adhesives and the solvent ethyl acetate were added. With a dissolver stirrer the mixture was homogenized at 1500 rpm for 10 minutes. In case of compositions 3c, 3e and 3f, drug substance and used enhancers were dispersed in the solvent ethyl acetate and ultrasonic treated for 5-10 min. The adhesives were added. These two steps can be done also in reverse order. With a turbine stirrer (composition 3c) or a dissolver stirrer (compositions 4e and 4f), the mixture was homogenized at 1500-2000 rpm for 10 minutes. In case of compositions 3d, drug substance was dispersed in the solvent ethyl acetate and ultrasonic treated for 5 min. The adhesive was added. These two steps can be done also in reverse order. With a stirrer, the mixture was homogenized at 2000 rpm for approx. 5 minutes. The enhancer was added and the mixture was homogenized at 2000 rpm for approx. 15 minutes. The mass was further stirred for approx. 60 minutes at 500 rpm.

Coating of the Coating Composition

See Example 1a-d for the coating process. The coating thickness gave an area weight of the guanfacine-containing layer of 151 (Ex. 3a), 150 (Ex. 3b), 153 (Ex. 3c), 143 (Ex. 3d), 143 (Ex. 3e) and 143 (Ex. 3) g/m². The dried film was laminated with a backing layer (e.g. PET 15 µm trsp) to provide a guanfacine-containing self-adhesive layer structure.

Preparation of the TTS

See Example 1.

Measurement of Skin Permeation

The permeated amount of TTS prepared according to Examples 3a-f was determined by experiments in accordance with the OECD Guideline (adopted Apr. 13, 2004) carried out with a 10.0 mL Franz diffusion cell. Split thickness Goettinger minipig skin (female) was used. A dermatome was used to prepare skin to a thickness of 800 µm, with an intact epidermis for all TTS. Die-cuts with an area of release of 1.179 cm² were punched from the TTS. The guanfacine permeated amount in the receptor medium of the Franz diffusion cell (phosphate buffer solution pH5.5 with 0.1% sodium azide as antibacteriological agent) at a temperature of 32±1° C. was measured and the corresponding cumulative permeated amount was calculated.

Figure 3:
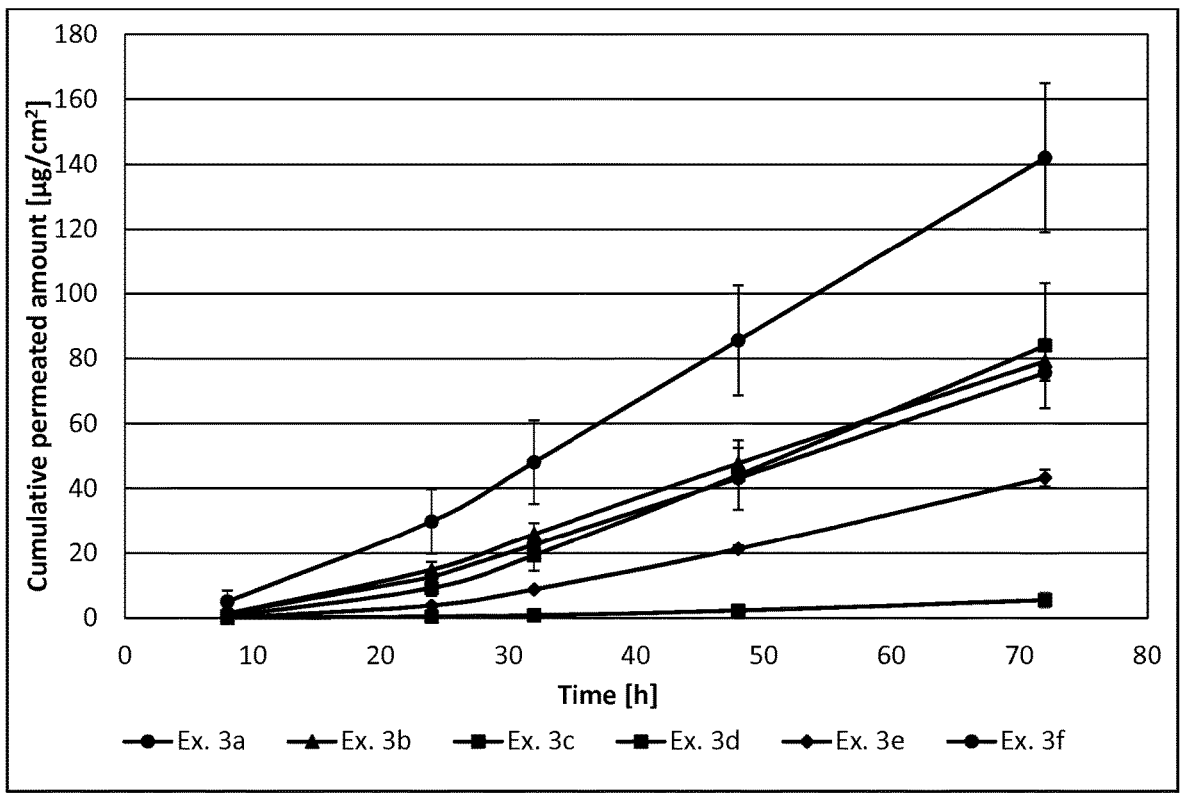
FIG. 3 depicts the guanfacine permeated amount of TTS prepared according to Examples 3a-f.

The results are shown in Table 3.2a and 3.2b and FIG. 3.

TABLE 3.2a

| | Cumulative permeated amount with SD [µg/cm²] | | | | | |
|---|---|---|---|---|---|---|
| | Ex. 3a (n = 3) | | Ex. 3b (n = 3) | | Ex. 3c (n = 3) | |
| Elapsed time [h] | Amount | SD | Amount | SD | Amount | SD |
| 8 | 5.00 | 3.46 | 1.33 | 0.63 | 0.47 | 0.24 |
| 24 | 29.80 | 9.99 | 14.83 | 2.38 | 9.15 | 2.36 |
| 32 | 48.14 | 12.88 | 25.86 | 3.32 | 19.34 | 4.84 |
| 48 | 85.57 | 16.85 | 47.79 | 4.63 | 44.08 | 10.76 |
| 72 | 142.44 | 22.89 | 79.16 | 6.07 | 84.04 | 19.24 |

TABLE 3.2b

| | Cumulative permeated amount with SD [µg/cm²] | | | | | |
|---|---|---|---|---|---|---|
| | Ex. 3d (n = 3) | | Ex. 3e (n = 3) | | Ex. 3f (n = 3) | |
| Elapsed time [h] | Amount | SD | Amount | SD | Amount | SD |
| 8 | <DL* | n.a. | <DL | n.a. | 1.35 | 1.53 |
| 24 | 0.36 | 0.19 | 3.80 | 0.15 | 12.51 | 5.34 |
| 32 | 0.81 | 0.43 | 8.77 | 0.38 | 22.57 | 5.34 |
| 48 | 2.22 | 1.05 | 21.34 | 1.10 | 43.21 | 7.40 |
| 72 | 5.47 | 2.24 | 43.34 | 2.6 | 75.57 | 9.50 |

*DL = Detection limit

Example 4A-4G

Coating Composition

The formulations of the guanfacine-containing coating compositions of Examples 4a-g are summarized in Table 4.1a, 4b and 4.1c below. The %-values refer to the amounts in % by weight.

TABLE 4.1 a

| | Ex. 4a | | Ex. 4b | | Ex. 4c | |
|---|---|---|---|---|---|---|
| Ingredient (Trade Name) | Amt [g] | Solids [%] | Amt [g] | Solids [%] | Amt [g] | Solids [%] |
| Guanfacine base | 1.65 | 8.21 | 1.01 | 8.04 | 1.6 | 7.98 |
| Silicone acrylic hybrid pressure sensitive adhesive in ethyl acetate Solids content of 50% by weight (PSA SilAc 7-6102 from Dow Corning Healthcare) | 33.17 | 82.68 | 20.77 | 82.88 | 33.55 | 83.88 |
| Oleylalcohol | 1.83 | 9.11 | 1.14 | 9.08 | — | — |
| Polyoxyethylene (4) lauryl ether (Brij L4) | — | — | — | — | 0.43 | 2.15 |
| Poly(ethylene glycol) average $M_n$ 300 (PEG 300) | — | — | — | — | 1.2 | 5.99 |
| Total | 36.65 | 100.0 | 22.92 | 100.0 | 36.78 | 100.0 |
| Area Weight [g/m²] | 154 | | 156 | | 149 | |
| Loading API [µg/cm²] | 1264 | | 1254 | | 1189 | |

TABLE 4.1b

| Ingredient (Trade Name) | Ex. 4d Amt [g] | Ex. 4d Solids [%] | Ex. 4e Amt [g] | Ex. 4e Solids [%] | Ex. 4f Amt [g] | Ex. 4f Solids [%] |
|---|---|---|---|---|---|---|
| Guanfacine base | 1.6 | 7.99 | 1.61 | 7.89 | 1.09 | 8.07 |
| Silicone acrylic hybrid pressure sensitive adhesive in ethyl acetate Solids content of 50% by weight (PSA SilAc 7-6102 from Dow Corning Healthcare) | 33.53 | 83.91 | — | — | — | — |
| Silicone acrylic hybrid pressure sensitive adhesive in ethyl acetate Solids content of 50% by weight (PSA SilAc 7-6302 from Dow Corning Healthcare) | — | — | 29.79 | 73.44 | 21.72 | 80.84 |
| Oleylalcohol | 1.2 | 5.99 | 1.8 | 8.82 | 1.24 | 9.17 |
| Polyoxyethylene (4) lauryl ether (Brij L4) | 0.42 | 2.10 | — | — | — | — |
| Cetearyl alcohol (and) sodium lauryl sulfate (and) sodium cetearyl sulfate | — | — | 2.01 | 9.85 | — | — |
| Glycerol monooleate | — | — | — | — | 0.26 | 1.92 |
| Total | 36.75 | 100.0 | 35.21 | 100.0 | 24.31 | 100.0 |
| Area Weight [g/m$^2$] | 188 | | 142 | | 152 | |
| Loading API [µg/cm$^2$] | 1502 | | 1120 | | 1227 | |

TABLE 4.1c

| Ingredient (Trade Name) | Ex. 4g Amt [g] | Ex. 4g Solids [%] |
|---|---|---|
| Guanfacine base | 0.63 | 4.13 |
| Silicone acrylic hybrid pressure sensitive adhesive in ethyl acetate Solids content of 50% by weight (PSA SilAc 7-6102 from Dow Corning Healthcare) | 24.5 | 80.52 |
| Oleylalcohol | 1.41 | 9.25 |
| Lactic acid | 0.93 | 6.10 |
| Total | 27.47 | 100.0 |
| Area Weight [g/m$^2$] | 154 | |
| Loading API [µg/cm$^2$] | 636 | |

Preparation of the Coating Composition

Drug substance and enhancers used were dispersed in the solvent ethyl acetate and ultrasonic treated for 2-10 minutes. The adhesives were added. These two steps can be done also in reverse order. With a dissolver stirrer (turbine stirrer for composition 4b and 4g), the mixture was homogenized at 1400-2000 rpm for approx. 10 minutes.

In case of composition 4e, the enhancers were dispersed by magnetic stirring at 60° C. for 10 minutes. Drug substance and the solvent ethyl acetate were added and the mixture was ultrasonic treated for 3 minutes. Then the adhesive was added, and the mass was further homogenized by magnetic stirring at 1400 rpm.

Coating of the Coating Composition

See Example 1a-d for the coating process. The coating thickness gave an area weight of the guanfacine-containing layer of 154 (Ex. 4a), 156 (Ex. 4b), 149 (Ex. 4c), 188 (Ex. 4d), 142 (Ex. 4e), 152 (Ex. 4f) and 154 (Ex. 4g) g/m$^2$. The dried film was laminated with a backing layer (PET 15 µm tsp) to provide a guanfacine-containing self-adhesive layer structure.

Preparation of the TTS

See Example 1.

Measurement of Skin Permeation

The permeated amount of TTS prepared according to Examples 4a-g was determined as described for Examples 1a-d above. Die-cuts with an area of release of 1.179 cm$^2$ were punched from the TTS.

Figure 4A:
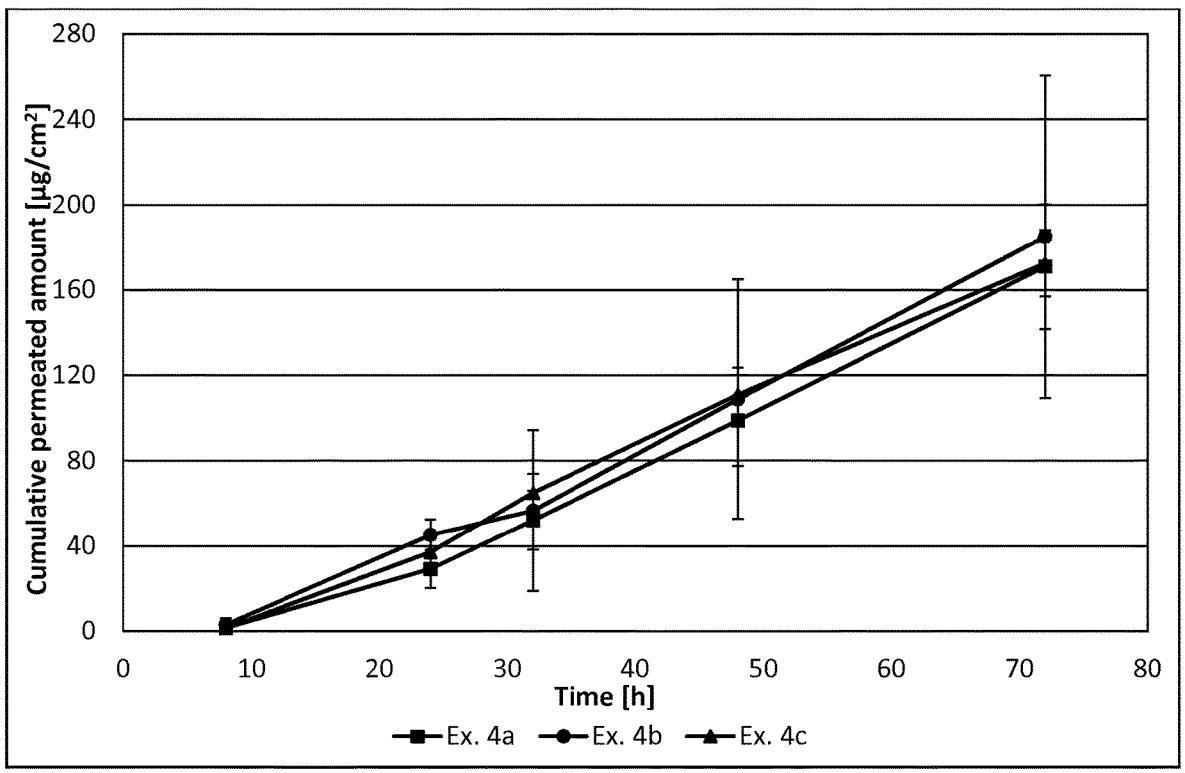
FIGS. 4a and 4b depict the guanfacine permeated amount of TTS prepared according to Examples 4a-g.
Figure 4B:
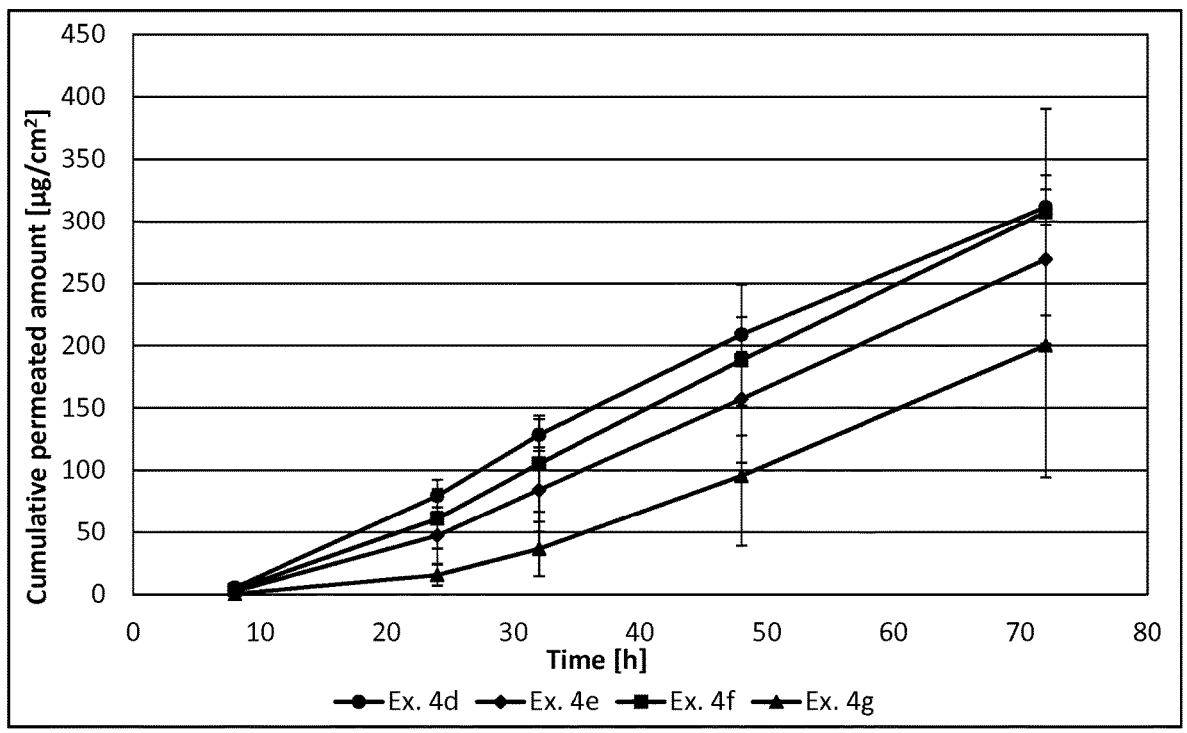

The results are shown in Table 4.2a and 4.2b and FIGS. 4a and 4b.

TABLE 4.2a

| | Cumulative permeated amount with SD [µg/cm$^2$] | | | | | |
|---|---|---|---|---|---|---|
| | Ex. 4a (n = 3) | | Ex. 4b (n = 3) | | Ex. 4c (n = 3) | |
| Elapsed time [h] | Amount | SD | Amount | SD | Amount | SD |
| 8 | 1.59 | 0.92 | 3.02 | 2.93 | 1.42 | 0.36 |
| 24 | 29.26 | 8.97 | 45.17 | 7.43 | 37.18 | 5.80 |
| 32 | 52.09 | 13.86 | 56.59 | 37.82 | 64.98 | 8.80 |
| 48 | 98.83 | 21.22 | 108.79 | 56.00 | 110.98 | 12.62 |
| 72 | 170.96 | 29.21 | 185.02 | 75.59 | 172.45 | 15.61 |

TABLE 4.2b

| | Cumulative permeated amount with SD [µg/cm$^2$] | | | | | | | |
|---|---|---|---|---|---|---|---|---|
| | Ex. 4d (n = 3) | | Ex. 4e (n = 3) | | Ex. 4f (n = 3) | | Ex. 4g (n = 3) | |
| Elapsed time [h] | Amount | SD | Amount | SD | Amount | SD | Amount | SD |
| 8 | 5.31 | 2.00 | 2.54 | 2.23 | 3.75 | 1.70 | 0.41 | 0.35 |
| 24 | 79.51 | 13.21 | 47.30 | 22.94 | 60.88 | 24.06 | 15.58 | 8.56 |
| 32 | 128.51 | 12.80 | 84.30 | 33.97 | 105.35 | 38.64 | 36.60 | 22.02 |

TABLE 4.2b-continued

| | Cumulative permeated amount with SD [µg/cm$^2$] | | | | | | |
|---|---|---|---|---|---|---|---|
| | Ex. 4d (n = 3) | | Ex. 4e (n = 3) | | Ex. 4f (n = 3) | | Ex. 4g (n = 3) |
| Elapsed time [h] | Amount | SD | Amount | SD | Amount | SD | Amount | SD |
| 48 | 208.94 | 13.78 | 157.30 | 50.97 | 188.42 | 60.31 | 95.60 | 56.42 |
| 72 | 311.54 | 14.41 | 269.30 | 67.90 | 307.45 | 83.11 | 200.23 | 106.06 |

Example 5A-D

Coating Composition

The formulations of the guanfacine-containing coating compositions of Examples 5a-d are summarized in Table 5.1a and 5.1b below. The %-values refer to the amounts in % by weight.

TABLE 5.1a

| | Ex. 5a | | Ex. 5b | |
|---|---|---|---|---|
| Ingredient (Trade Name) | Amt [g] | Solids [%] | Amt [g] | Solids [%] |
| Guanfacine base | 2.71 | 12.00 | 3.61 | 11.63 |
| Silicone acrylic hybrid pressure sensitive adhesive in ethyl acetate Solids content of 50% by weight (PSA SilAc 7-6102 from Dow Corning Healthcare) | 16.71 | 37.00 | — | — |
| Silicone acrylic hybrid pressure sensitive adhesive in ethyl acetate Solids content of 50% by weight (PSA SilAc 7-6302 from Dow Corning Healthcare) | 0.91 | 2.01 | — | — |
| Amine-compatible silicone adhesive (silanol endblocked polydimethylsiloxane polycondensed with a silicate resin and reacted with trimethylsilyl) in ethyl acetate Solids content of 60% by weight (DOW CORNING ® BIO-PSA Q7-4302) | 14.67 | 38.98 | — | — |
| Amine-compatible silicone adhesive (silanol endblocked polydimethylsiloxane polycondensed with a silicate resin and reacted with trimethylsilyl) in heptane Solids content of 73% by weight (DOW CORNING ® BIO-PSA Q7-4201) | — | — | 8.38 | 19.76 |
| Amine-compatible silicone adhesive (silanol endblocked polydimethylsiloxane polycondensed with a silicate resin and reacted with trimethylsilyl) in heptane Solids content of 73% by weight (DOW CORNING ® BIO-PSA Q7-4301) | — | — | 24.33 | 56.89 |
| Polyvinyl caprolactam-polyvinyl acetate-polyethylene graft copolymer (Soluplus) | 0.45 | 1.99 | 0.61 | 1.96 |
| Oleylalcohol | 0.89 | 3.94 | 1.81 | 5.83 |
| Polyoxyethylene (4) lauryl ether (Brij L4) | 0.92 | 4.07 | 1.22 | 3.93 |
| Total | 37.26 | 100.0 | 39.96 | 100.0 |
| Area Weight [g/m$^2$] | | 100 | | 91 |
| Loading API [µg/cm$^2$] | | 1200 | | 1058 |

TABLE 5.1b

| | Ex. 5c | | Ex. 5d | |
|---|---|---|---|---|
| Ingredient (Trade Name) | Amt [g] | Solids [%] | Amt [g] | Solids [%] |
| Guanfacine base | 2.70 | 11.92 | 2.70 | 11.76 |
| Silicone acrylic hybrid pressure sensitive adhesive in ethyl acetate Solids content of 50% by weight (PSA SilAc 7-6102 from Dow Corning Healthcare) | 16.77 | 37.02 | 16.75 | 36.48 |

TABLE 5.1b-continued

| Ingredient (Trade Name) | Ex. 5c Amt [g] | Ex. 5c Solids [%] | Ex. 5d Amt [g] | Ex. 5d Solids [%] |
|---|---|---|---|---|
| Silicone acrylic hybrid pressure sensitive adhesive in ethyl acetate Solids content of 50% by weight (PSA SilAc 7-6302 from Dow Corning Healthcare) | 0.88 | 1.94 | 0.94 | 2.05 |
| Amine-compatible silicone adhesive (silanol endblocked polydimethylsiloxane polycondensed with a silicate resin and reacted with trimethylsilyl) in ethyl acetate Solids content of 60% by weight (DOW CORNING ® BIO-PSA Q7-5202) | 14.68 | 38.96 | — | — |
| Silicone adhesive (silanol endblocked polydimethylsiloxane polycondensed with a silicate resin) in ethyl acetate Solids content of 60% by weight (DOW CORNING ® BIO-PSA Q7-5502) | — | — | 15.13 | 39.74 |
| Polyvinyl caprolactam-polyvinyl acetate-polyethylene graft copolymer (Soluplus) | 0.46 | 2.03 | 0.44 | 1.92 |
| Oleylalcohol | 0.94 | 4.15 | 0.94 | 4.09 |
| Polyoxyethylene (4) lauryl ether (Brij L4) | 0.90 | 3.97 | 0.91 | 3.96 |
| Total | 37.33 | 100.0 | 37.81 | 100.0 |
| Area Weight [g/m$^2$] | | 106 | | 110 |
| Loading API [µg/cm$^2$] | | 1265 | | 1294 |

Preparation of the Coating Composition

Drug substance and enhancers used were dispersed in the solvent ethyl acetate and ultrasonic treated for approx. 10 minutes. The adhesives were added. These two steps can be done also in reverse order. With a dissolver stirrer, the mixture was homogenized at 2000 rpm for 2 minutes. Soluplus was added, and the mass was stirred for additional 2 min at 2000 rpm and further homogenized at 1500 rpm for at least 30 min.

In case of composition 5b, enhancer polyoxyethylene (4) lauryl ether and Soluplus were dispersed in the solvent ethanol and ultrasonic treated for 10 minutes. Drug substance and enhancer Oleylalcohol were added and the mixture was ultrasonic treated for additional 10 min. The adhesives were added.

In case of composition 5d, drug substance and enhancers were dispersed in the solvent ethyl acetate and ultrasonic treated for approx. 10 minutes. The adhesives and Soluplus were added. These two steps can be done also in reverse order. With a dissolver stirrer, the mixture was homogenized at 2000 rpm for approx. 2 minutes. The mass was further stirred at 1500 rpm for at least 30 minutes.

Coating of the Coating Composition

See Example 1a-d for the coating process. The coating thickness gave an area weight of the guanfacine-containing layer of 100 (Ex. 5a), 91 (Ex. 5b), 106 (Ex. 5c) and 110 (Ex. 5d) g/m$^2$. The dried film was laminated with a backing layer (PET 15 µm tsp) to provide a guanfacine-containing self-adhesive layer structure.

Preparation of the TTS

See Example 1.

Measurement of Skin Permeation

The permeated amount of TTS prepared according to Examples 5a-d was determined as described for Examples 1a-d above. Die-cuts with an area of release of 1.188 cm$^2$ were punched from the TTS.

Figure 5:
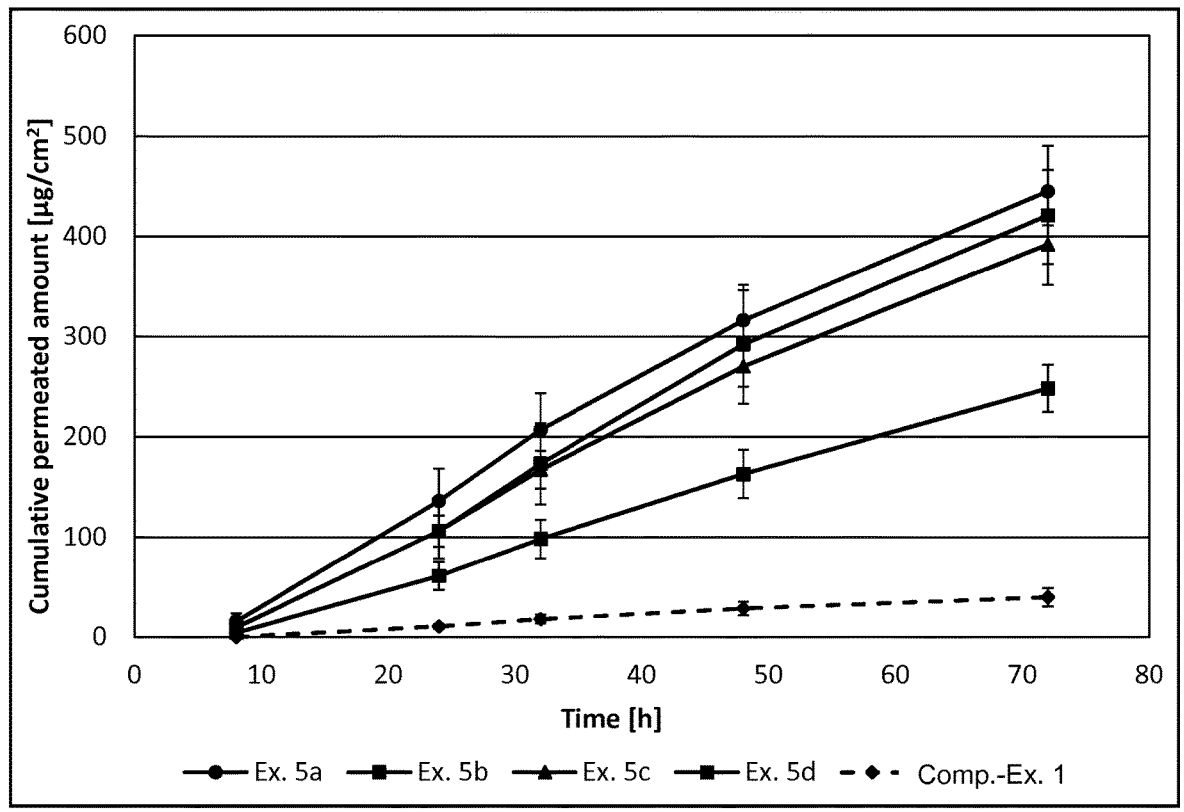
FIG. 5 depicts the guanfacine permeated amount of TTS prepared according to Examples 5a-d and Comparative Example 1.

The results are shown in Table 5.2a and 5.2b and FIG. 5.

TABLE 5.2a

Cumulative permeated amount with SD [µg/cm$^2$]

| Elapsed time [h] | Ex. 5a (n = 3) Amount | SD | Ex. 5b (n = 3) Amount | SD | Ex. 5c (n = 3) Amount | SD |
|---|---|---|---|---|---|---|
| 8 | 15.47 | 7.78 | 9.59 | 4.15 | 9.29 | 3.43 |
| 24 | 135.81 | 32.65 | 105.52 | 27.41 | 105.76 | 15.46 |
| 32 | 206.74 | 36.20 | 172.82 | 40.35 | 167.26 | 18.72 |
| 48 | 316.41 | 30.37 | 292.39 | 59.19 | 269.59 | 19.98 |
| 72 | 444.74 | 21.26 | 420.72 | 69.42 | 391.59 | 19.42 |

TABLE 5.2b

Cumulative permeated amount with SD [µg/cm$^2$]

| Elapsed time [h] | Ex. 5d (n = 3) Amount | SD |
|---|---|---|
| 8 | 4.26 | 1.29 |
| 24 | 61.19 | 13.91 |
| 32 | 98.09 | 19.36 |
| 48 | 163.39 | 24.05 |
| 72 | 247.69 | 23.57 |

Example 6

Coating Composition

The formulation of the guanfacine-containing coating composition of Examples 6 is summarized in Table 6.1. The %-values refer to the amounts in % by weight.

TABLE 6.1

| Ingredient (Trade Name) | Ex. 6 | |
|---|---|---|
| | Amt [g] | Solids [%] |
| Guanfacine base | 0.80 | 4.01 |
| Silicone acrylic hybrid pressure sensitive adhesive in ethyl acetate Solids content of 50% by weight (PSA SilAc 7-6102 from Dow Corning Healthcare) | — | — |
| Acrylate-vinylacetate adhesive in ethyl acetate/ethanol/heptane/methanol Solids content of 42% by weight (DURO-TAK ® 387-2516) | 38.44 | 81.02 |
| Oleylalcohol | 1.79 | 8.96 |
| 2-(2-Ethoxyethoxy)ethanol | 1.20 | 6.01 |
| Total | 42.23 | 100.0 |
| Area Weight [g/m²] | 125 | |
| Loading API [µg/cm²] | 501 | |

Preparation of the Coating Composition

Drug substance and enhancers used were dispersed and ultrasonic treated for approx. 5 min. Then the adhesives and ethyl acetate were added. With a dissolver stirrer the mixture was homogenized at 1500 rpm for approx. 10 minutes.

Coating of the Coating Composition

See Example 1a-d for the coating process. The coating thickness gave an area weight of the guanfacine-containing layer of 125 g/m². The dried film was laminated with a backing layer (PET 15 µm tsp) to provide a guanfacine-containing self-adhesive layer structure.

Preparation of the TTS

See Example 1.

Measurement of Skin Permeation

The permeated amount of TTS prepared according to Examples 6 was determined by experiments in accordance with the OECD Guideline (adopted Apr. 13, 2004) carried out with a 10.0 mL Franz diffusion cell. Split thickness Goettinger minipig skin (female) was used. A dermatome was used to prepare skin to a thickness of 800 µm, with an intact epidermis for all TTS. Diecuts with an area of release of 1.188 cm² were punched from the TTS. The guanfacine permeated amount in the receptor medium of the Franz diffusion cell (phosphate buffer solution pH5.5 with 0.1% sodium azide as antibacteriological agent) at a temperature of 32±1° C. was measured and the corresponding cumulative permeated amount was calculated.

Figure 6:
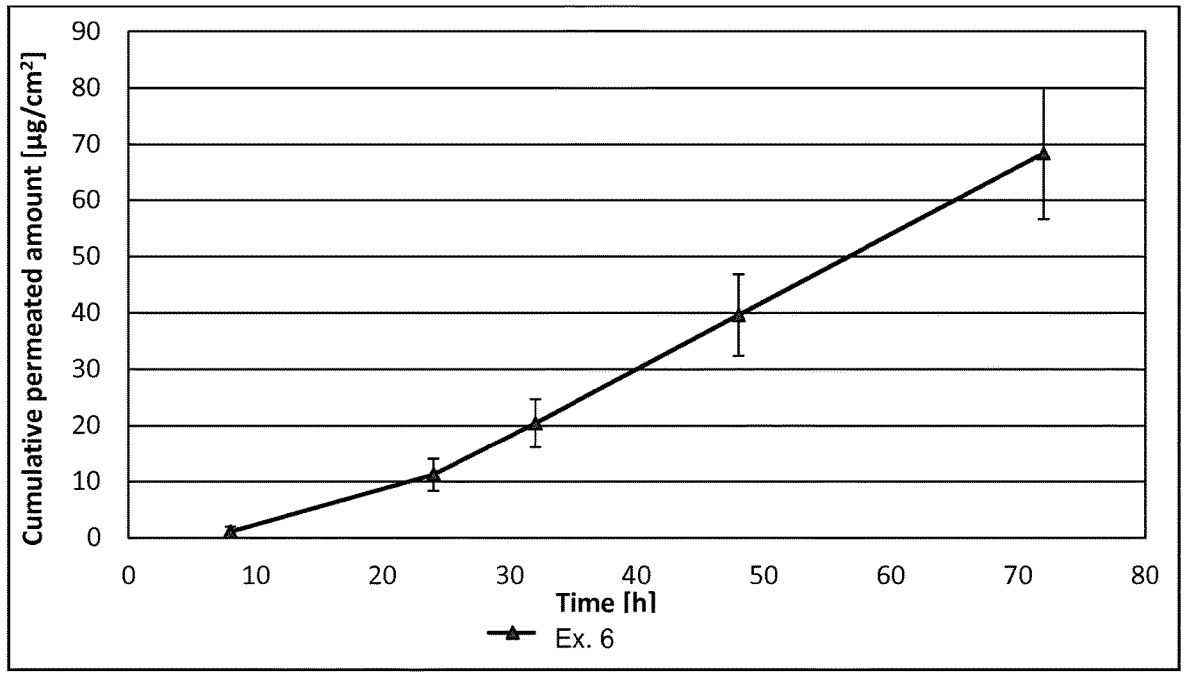

The results are shown in Table 6.2 and FIG. 6.

TABLE 6.2

| | Cumulative permeated amount with SD [µg/cm²] | |
|---|---|---|
| | Ex. 6 (n = 3) | |
| Elapsed time [h] | Amount | SD |
| 8 | 1.07 | 0.92 |
| 24 | 11.16 | 2.86 |
| 32 | 20.45 | 4.24 |
| 48 | 39.58 | 7.22 |
| 72 | 68.31 | 11.64 |

Example 7A-C

The formulations of the guanfacine-containing coating compositions of Examples 7a-7c are summarized in Table 7.1. The %-values refer to the amounts in % by weight.

TABLE 7.1

| | Ex. 7a | | Ex. 7b | | Ex. 7c | |
|---|---|---|---|---|---|---|
| Ingredient (Trade Name) | Amt [g] | Solids [%] | Amt [g] | Solids [%] | Amt [g] | Solids [%] |
| Guanfacine base | 3.60 | 11.99 | 1.60 | 8.0 | 0.80 | 3.98 |
| Acrylate-vinylacetate adhesive in ethyl acetate/ethanol/heptane/methanol Solids content of 42% by weight (DURO-TAK ® 387-2516) | 54.4 | 76.09 | 39.52 | 83.0 | 41.02 | 85.81 |
| Polyvinyl caprolactama-polyvinyl acetate-polyethylene graft copolymer (Soluplus) | 0.6 | 1.99 | — | — | — | — |
| Oleylalcohol | 1.78 | 5.93 | 1.8 | 9.0 | 1.23 | 6.13 |
| Polyoxyethylene (4) lauryl ether (Brij L4) | 1.2 | 4.00 | — | — | 0.82 | 4.08 |
| Total | 61.58 | 100.0 | 42.92 | 100.0 | 43.87 | 100.0 |
| Area Weight [g/m²] | 98 | | 140 | | 100 | |
| Loading API [µg/cm²] | 1175 | | 1120 | | 398 | |

Preparation of the Coating Composition

Drug substance and enhancers used were dispersed in the solvent ethyl acetate and ultrasonic treated for approx. 10 minutes. The adhesives were added. These two steps can be done also in reverse order. With a dissolver stirrer, the mixture was homogenized at 2000 rpm for 2 minutes. The mass was stirred again for 10 minutes at 1000 rpm.

In case of composition 7a, Soluplus was added after the mixture was homogenized at 2000 rpm for 2 minutes. The mass was stirred for additional 2 min at 2000 rpm and further homogenized at 1500 rpm for 30 min.

Coating of the Coating Composition

See Example 1a-d for the coating process. The coating thickness gave an area weight of the guanfacine-containing layer of 98 (Ex. 7a), 140 (Ex. 7b) and 100 (Ex. 7c) g/m². The dried film was laminated with a backing layer (PET 15 µm tsp) to provide guanfacine-containing self-adhesive layer structure.

Preparation of the TTS

See Example 1.

Measurement of Skin Permeation

The permeated amount of TTS prepared according to Examples 7a-7c was determined as described for Examples 1a-d above. Die-cuts with an area of release of 1.188 cm² were punched from the TTS.

Figure 7:
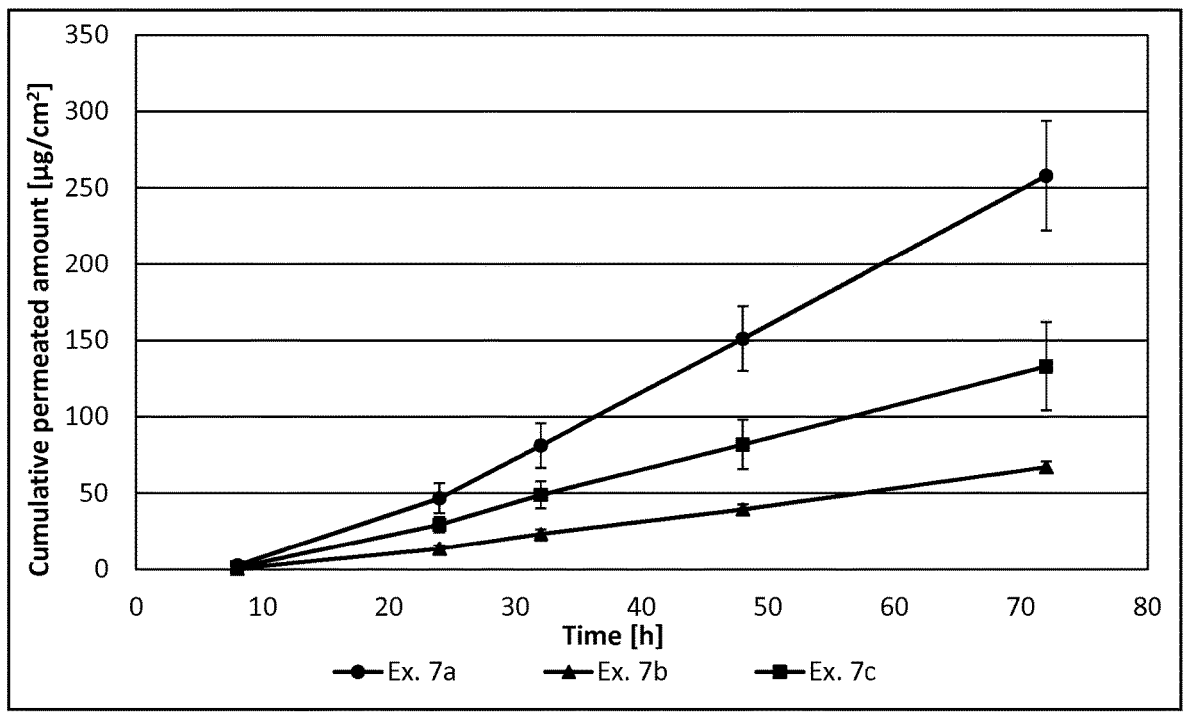
FIG. 7 depicts the guanfacine permeated amount of TTS prepared according to Examples 7a-c.

The results are shown in Table 7.2 and FIG. 7.

TABLE 7.2

| | Cumulative permeated amount with SD [µg/cm²] | | | | | |
|---|---|---|---|---|---|---|
| | Ex. 7a (n = 3) | | Ex. 7b (n = 3) | | Ex. 7c (n = 3) | |
| Elapsed time [h] | Amount | SD | Amount | SD | Amount | SD |
| 8 | 2.49 | 0.88 | 0.48 | 0.23 | 1.30 | 0.38 |
| 24 | 46.83 | 9.72 | 13.62 | 1.92 | 29.40 | 4.93 |
| 32 | 81.23 | 14.52 | 23.27 | 2.88 | 49.00 | 8.82 |
| 48 | 151.03 | 21.19 | 39.50 | 3.24 | 81.93 | 16.19 |
| 72 | 257.59 | 35.95 | 67.10 | 3.70 | 132.86 | 28.77 |

Example 8A-B

Coating Composition

The formulations of the guanfacine-containing coating compositions of Examples 8a-b are summarized in Table 8.1 below. The %-values refer to the amounts in % by weight.

TABLE 8.1

| | Ex. 8a | | Ex. 8b | |
|---|---|---|---|---|
| Ingredient (Trade Name) | Amt [g] | Solids [%] | Amt [g] | Solids [%] |
| Guanfacine base | 2.43 | 8.05 | 1.18 | 3.92 |
| Amine-compatible silicone adhesive (silanol endblocked polydimethylsiloxane polycondensed with a silicate resin and reacted with trimethylsilyl) in ethyl acetate Solids content of 60% by weight (DOW CORNING ® BIO-PSA Q7-4302) | 31.20 | 62.02 | 32.28 | 64.33 |
| Amine-compatible silicone adhesive (silanol endblocked polydimethylsiloxane polycondensed with a silicate resin and reacted with trimethylsilyl) in ethyl acetate Solids content of 62% by weight (DOW CORNING ® BIO-PSA Q7-4202) | 10.18 | 20.91 | 10.61 | 21.85 |
| Oleylalcohol | 2.72 | 9.01 | 1.78 | 5.91 |
| Polyoxyethylene (4) lauryl ether (Brij L4) | — | — | 1.2 | 3.99 |
| Total | 46.53 | 100.0 | 47.05 | 100.0 |
| Area Weight [g/m²] | 115 | | 113 | |
| Loading API [µg/cm²] | 926 | | 443 | |

Preparation of the Coating Composition

Drug substance and enhancers used were dispersed in the solvent ethyl acetate and ultrasonic treated for approx. 10 minutes. The adhesives were added. These two steps can be done also in reverse order. With a dissolver stirrer, the mixture was homogenized at 2000 rpm for 2 minutes. The mass was stirred again for 10 minutes at 1000 rpm.

Coating of the Coating Composition

See Example 1a-d for the coating process. The coating thickness gave an area weight of the guanfacine-containing layer of 115 (Ex. 8a) and 113 (Ex. 8b) g/m². The dried film was laminated with a backing layer (e.g. MN 19) to provide a guanfacine-containing self-adhesive layer structure.

Preparation of the TTS

See Example 1.

Measurement of Skin Permeation

The permeated amount of TTS prepared according to Examples 8a-b was determined as described for Examples 1a-d above. Die-cuts with an area of release of 1.188 cm² were punched from the TTS.

Figure 8:
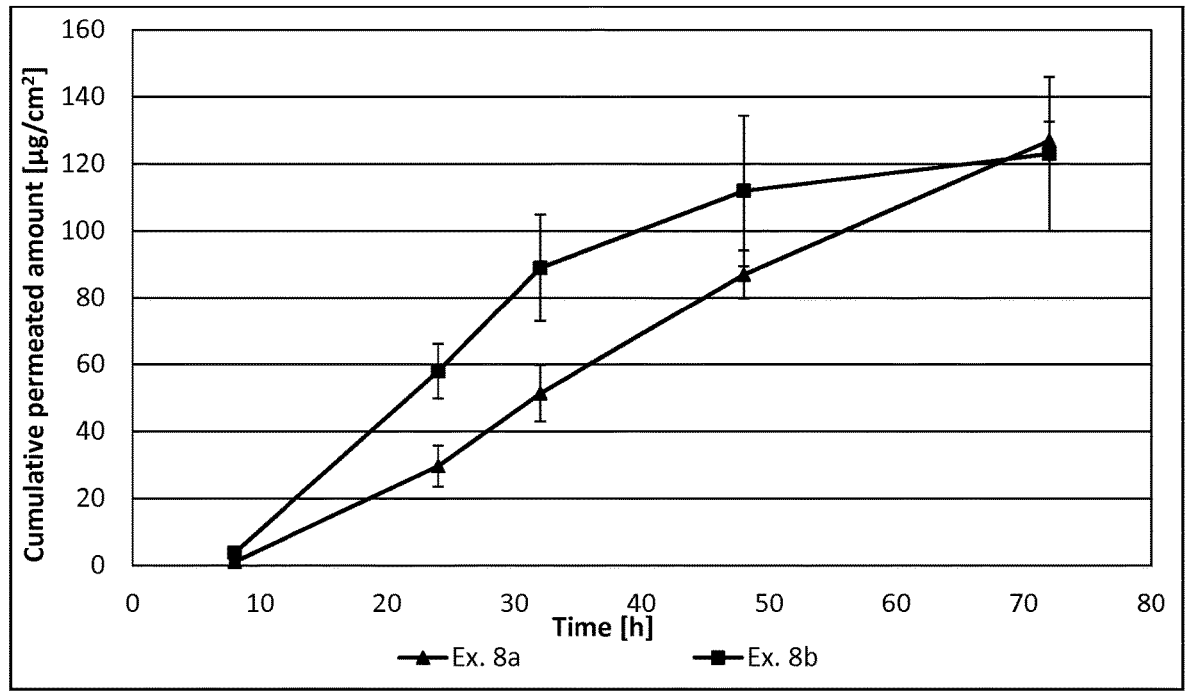
FIG. 8 depicts the guanfacine permeated amount of TTS prepared according to Examples 8a-b.

The results are shown in Tables 8.2 and FIG. 8.

TABLE 8.2

| | Cumulative permeated amount with SD [µg/cm²] | | | |
|---|---|---|---|---|
| | Ex. 8a (n = 3) | | Ex. 8b (n = 3) | |
| Elapsed time [h] | Amount | SD | Amount | SD |
| 8 | 1.12 | 0.42 | 3.85 | 0.69 |
| 24 | 29.72 | 6.22 | 57.95 | 8.12 |
| 32 | 51.39 | 8.43 | 89.02 | 15.99 |
| 48 | 87.02 | 7.18 | 111.58 | 22.49 |
| 72 | 126.59 | 5.60 | 122.71 | 22.96 |

Example 9A-B

The formulations of the guanfacine-containing coating compositions of Examples 9a-b are summarized in Table 9.1 below. The %-values refer to the amounts in % by weight.

TABLE 9.1

| | Ex. 9a | | Ex. 9b | |
|---|---|---|---|---|
| Ingredient (Trade Name) | Amt [g] | Solids [%] | Amt [g] | Solids [%] |
| Guanfacine base | 3.60 | 11.93 | 2.70 | 11.98 |
| Amine-compatible silicone adhesive (silanol | 9.15 | 18.79 | 13.74 | 37.80 |

TABLE 9.1-continued

|  | Ex. 9a | | Ex. 9b | |
| --- | --- | --- | --- | --- |
| Ingredient (Trade Name) | Amt [g] | Solids [%] | Amt [g] | Solids [%] |
| endblocked polydimethylsiloxane polycondensed with a silicate resin and reacted with trimethylsilyl) in ethyl acetate Solids content of 62% by weight (DOW CORNING ® BIO-PSA Q7-4202) | | | | |
| Amine-compatible silicone adhesive (silanol endblocked polydimethylsiloxane polycondensed with a silicate resin and reacted with trimethylsilyl) in ethyl acetate Solids content of 60% by weight (DOW CORNING ® BIO-PSA Q7-4302) | 28.47 | 56.59 | — | — |
| Acrylate-vinylacetate adhesive in ethyl acetate/ethanol/heptane/methanol Solids content of 42% by weight (DURO-TAK ® 387-2516) | — | — | 20.45 | 38.11 |
| Polyvinyl caprolactam-polyvinyl acetate-polyethylene graft copolymer (Soluplus) | 0.61 | 2.02 | 0.47 | 2.09 |
| Oleylalcohol | 1.82 | 6.03 | 1.36 | 6.03 |
| Polyoxyethylene (4) lauryl ether (Brij L4) | 1.40 | 4.64 | 0.90 | 3.99 |
| Total | 45.05 | 100.0 | 39.62 | 100.0 |
| Area Weight [g/m$^2$] | 106 | | 103 | |
| Loading API [µg/cm$^2$] | 1265 | | 1234 | |

Preparation of the Coating Composition

Drug substance and used enhancers were dispersed in the solvent ethyl acetate and ultrasonic treated for approx. 10 minutes. The adhesives were added. These two steps can be done also in reverse order. With a dissolver stirrer, the mixture was homogenized at 2000 rpm for 2 minutes. Soluplus was added, and the mass was stirred for additional 2 min at 2000 rpm and further homogenized at 1500 rpm for 30 min.

Coating of the Coating Composition

See Example 1a-d for the coating process. The coating thickness gave an area weight of the guanfacine-containing layer of 106 (Ex. 9a) and 103 (Ex. 9b) g/m$^2$. The dried film was laminated with a backing layer (eg. siliconized MN 19) to provide a guanfacine-containing self-adhesive layer structure.

Preparation of the TTS

See Example 1.

Measurement of Skin Permeation

The permeated amount of TTS prepared according to Examples 9a-b was determined as described for Examples 1a-d above. Die-cuts with an area of release of 1.188 cm$^2$ were punched from the TTS.

Figure 9:
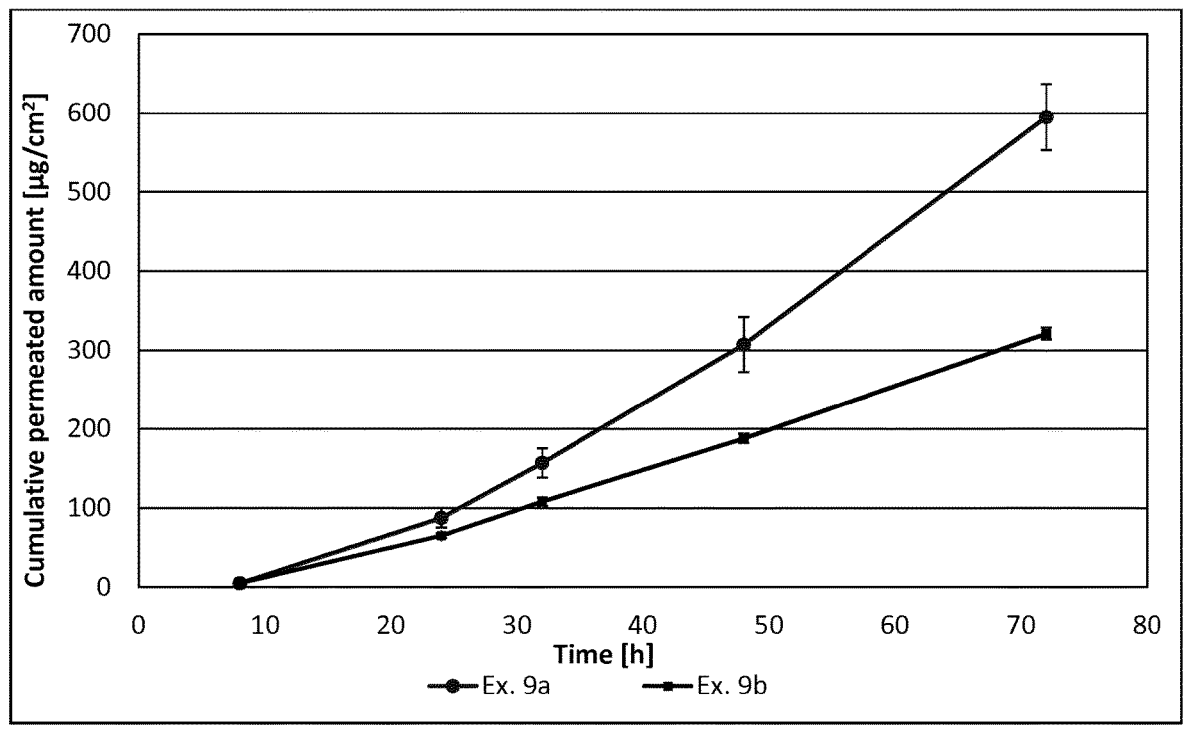
FIG. 9 depicts the guanfacine permeated amount of TTS prepared according to Examples 9a-b.

The results are shown in Table 9.2 and FIG. 9.

TABLE 9.2

Cumulative permeated amount with SD [µg/cm$^2$]

| | Ex. 9a (n = 3) | | Ex. 9b (n = 3) | |
| --- | --- | --- | --- | --- |
| Elapsed time [h] | Amount | SD | Amount | SD |
| 8 | 4.71 | 1.80 | 5.01 | 0.76 |
| 24 | 87.34 | 12.24 | 65.01 | 2.84 |
| 32 | 157.38 | 18.63 | 107.51 | 5.00 |
| 48 | 306.71 | 34.78 | 187.81 | 6.05 |
| 72 | 594.71 | 41.70 | 321.48 | 7.53 |

Example 10A-C

The formulations of the guanfacine-containing coating compositions of Examples 10a-c are summarized in Table 10.1 below. The %-values refer to the amounts in % by weight.

TABLE 10.1

|  | Ex. 10a | | Ex. 10b | | Ex. 10c | |
| --- | --- | --- | --- | --- | --- | --- |
| Ingredient (Trade Name) | Amt [g] | Solids [%] | Amt [g] | Solids [%] | Amt [g] | Solids [%] |
| Guanfacine base | 0.87 | 3.87 | 3.14 | 12.05 | 1.63 | 6.12 |
| Silicone acrylic hybrid pressure sensitive adhesive in ethyl acetate Solids content of 50% by weight (PSA SilAc 7-6102 from Dow Corning Healthcare) | 23.05 | 51.75 | 38.21 | 74.04 | 42.84 | 81.18 |
| Silicone acrylic hybrid pressure sensitive adhesive in ethyl acetate Solids content of 50% by weight (PSA SilAc 7-6302 from Dow Corning Healthcare) | 15.39 | 34.42 | 2.00 | 3.86 | 2.32 | 4.38 |

TABLE 10.1-continued

| Ingredient (Trade Name) | Ex. 10a Amt [g] | Ex. 10a Solids [%] | Ex. 10b Amt [g] | Ex. 10b Solids [%] | Ex. 10c Amt [g] | Ex. 10c Solids [%] |
|---|---|---|---|---|---|---|
| Polyvinyl caprolactam-polyvinyl acetate-polyethylene graft copolymer (Soluplus) | — | — | 0.55 | 2.11 | — | — |
| Oleylalcohol | 1.33 | 5.91 | 1.04 | 3.99 | 1.11 | 4.16 |
| Polyoxyethylene (4) lauryl ether (Brij L4) | 0.91 | 4.05 | 1.03 | 3.95 | 1.11 | 4.16 |
| Total | 41.55 | 100.0 | 45.97 | 100.0 | 49.01 | 100.0 |
| Area Weight [g/m$^2$] | | 104 | | 95 | | 95 |
| Loading API [µg/cm$^2$] | | 403 | | 1145 | | 581 |

Preparation of the Coating Composition

Drug substance and enhancers used were dispersed in the solvent ethyl acetate. Then the adhesives were added. These two steps can be done also in reverse order. With a dissolver stirrer the mixture was homogenized at 2000 rpm for 2-5 minutes. The mass was stirred again for approx. 30 minutes at 1500 rpm.

In case of composition 10b, Soluplus was added after the mixture was homogenized at 2000 rpm for 2 minutes. The mass was stirred for approx. 2 min at 2000 rpm and further homogenized at 1500 rpm for approx. 30 min.

Coating of the Coating Composition

See Example 1a-d for the coating process. The coating thickness gave an area weight of the guanfacine-containing layer of 104 (Ex. 10a), 95 (Ex. 10b) and 95 (Ex. 10c) g/m$^2$. The dried film was laminated with backing layer (PET 15 µm tsp) to provide a guanfacine-containing self-adhesive layer structure.

Preparation of the TTS

See Example 1.

Measurement of Skin Permeation

The permeated amount of TTS prepared according to Examples 10a-c was determined as described for Examples 1a-d above. Die-cuts with an area of release of 1.188 cm$^2$ were punched from the TTS.

Figure 10:
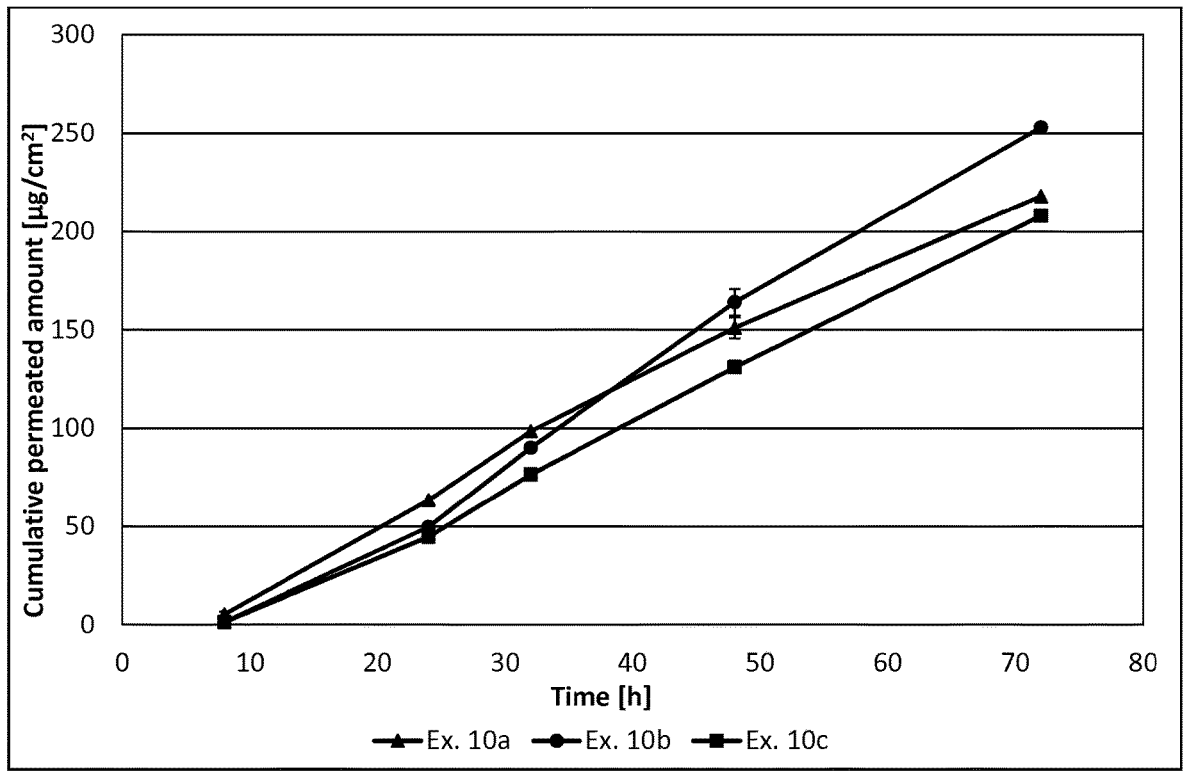
FIG. 10 depicts the guanfacine permeated amount of TTS prepared according to Examples 10a-c.

The results are shown in Table 10.2 and FIG. 10.

TABLE 10.2

Cumulative permeated amount with SD [µg/cm$^2$]

| Elapsed time [h] | Ex. 10a (n = 3) Amount | SD | Ex. 10b (n = 3) Amount | SD | Ex. 10c (n = 3) Amount | SD |
|---|---|---|---|---|---|---|
| 8 | 5.30 | 1.47 | 1.39 | 0.74 | 1.34 | 0.39 |
| 24 | 63.37 | 5.49 | 49.68 | 6.79 | 44.68 | 2.36 |
| 32 | 98.51 | 7.34 | 90.15 | 9.13 | 76.53 | 2.77 |
| 48 | 151.49 | 8.9 | 163.54 | 11.04 | 130.54 | 2.89 |
| 72 | 218.12 | 11.32 | 253.1 | 26.2 | 208.36 | 16.92 |

Comparative Example 1

Comparative Example 1 (Comp.-Ex. 1) is a mixture of Oppanol B10 and Oppanol B100 with a ratio of 15/85 and Guanfacine base. The formulation of the guanfacine-containing coating composition of Comp.-Ex. 1 is summarized in Table 11.1 below. The %-values refer to the amounts in % by weight

TABLE 11.1

| Ingredient (Trade Name) | Comp.-Ex. 1 Amt [g] | Comp.-Ex. 1 Solids [%] |
|---|---|---|
| Guanfacine base | 2.7 | 11.98 |
| Polyisobutylene (Oppanol B10/ Oppanol B100 - Parts 15/85) in hexane:heptane 1:1 | 43.7 | 88.02 |
| Total | 46.40 | 100.0 |
| Area Weight [g/m$^2$] | | 91 |
| Loading API [µg/cm$^2$] | | 1090 |

Preparation of the Coating Composition

Drug substance was dispersed in the solvent n-heptane and ultrasonic treated for 10 min. Then the adhesive mixture was added. These two steps can be done also in reverse order. With a dissolver stirrer the mixture was homogenized at 100-500 rpm for 30 minutes.

Coating of the Coating Composition

See Example 1a-c for the coating process. The coating thickness gave an area weight of the guanfacine-containing layer of 91 (Comp.-Ex. 1) g/m$^2$. The dried film was laminated with a backing layer (siliconized MN 19) to provide a guanfacine-containing self-adhesive layer structure.

Preparation of the TTS

See Example 1.

Measurement of Skin Permeation

The permeated amount of TTS prepared according to Comp.-Ex. 1 was determined as described for Examples 2a-d above. Die-cuts with an area of release of 1.188 cm$^2$ were punched from the TTS.

The results are shown in Table 11.2 and FIG. 5.

TABLE 11.2

Cumulative permeated amount with SD [µg/cm$^2$]

| Elapsed time [h] | Comp.-Ex. 1 (n = 3) Amount | SD |
|---|---|---|
| 8 | <DL | n.a. |
| 24 | 10.62 | 2.47 |
| 32 | 17.77 | 4.27 |
| 48 | 28.57 | 6.86 |
| 72 | 39.74 | 8.95 |

* DL = Detection limit

Comparative Example 2A-B

Coating Composition

The formulations of the guanfacine-containing coating compositions of Comparative Examples 2a-b are summarized in Table 12.1 below. The %-values refer to the amounts in % by weight.

TABLE 12.1

| Ingredient (Trade Name) | Comp.-Ex. 2a Amt [g] | Comp.-Ex. 2a Solids [%] | Comp.-Ex. 2b Amt [g] | Comp.-Ex. 2b Solids [%] |
|---|---|---|---|---|
| Guanfacine base | 2.87 | 20.08 | 2.40 | 20.00 |
| Acrylate-vinylacetate adhesive in ethyl acetate/ethanol/heptane/methanol Solids content of 42% by weight (DURO-TAK ® 387-2516) | 27.14 | 79.92 | — | — |
| Acrylate-vinylacetate adhesive in ethyl acetate Solids content of 40% by weight (DURO-TAK ® 87-4098) | — | — | 23.76 | 80.00 |
| Total | 30.01 | 100.0 | 26.16 | 100.0 |
| Area Weight [g/m$^2$] | | 49 | | 50 |
| Loading API [µg/cm$^2$] | | 984 | | 1000 |

Preparation of the Coating Composition

Drug substance was dispersed in the solvent ethyl acetate and ultrasonic treated for approx. 5 min. Then the adhesives were added. These two steps can be done also in reverse order. With a dissolver stirrer the mixture was homogenized at 500-800 rpm for approx. 10 minutes.

In case of Comp.-Ex. 2a drug substance was dispersed directly in the adhesive. The mixture was stirred at 500 rpm for approx. 10 minutes.

Coating of the Coating Composition

See Example 1a-d for the coating process. For Comp.-Ex. 2b the coating composition was coated on a PET 100 µm film. The coating thickness gave an area weight of the guanfacine-containing layer of 49 (Comp.-Ex. 2a) and 50 (Comp.-Ex. 2b) g/m$^2$. The dried film was laminated with a backing layer (PET 15 µm tsp) to provide a guanfacine-containing self-adhesive layer structure.

Preparation of the TTS

See Example 1.

Measurement of Skin Permeation

The permeated amount of TTS prepared according to Comp.-Ex. 2a-b was determined by experiments in accordance with the OECD Guideline (adopted Apr. 13, 2004) carried out with a 10.0 mL Franz diffusion cell. Split thickness Goettinger minipig skin (female) was used. A dermatome was used to prepare skin to a thickness of 800 µm, with an intact epidermis for all TTS. Die-cuts with an area of release of 1.165 cm$^2$ were punched from the TTS. The guanfacine permeated amount in the receptor medium of the Franz diffusion cell (phosphate buffer solution pH5.5 with 0.1% sodium azide as antibacteriological agent) at a temperature of 32±1° C. was measured and the corresponding cumulative permeated amount was calculated.

Figure 11:
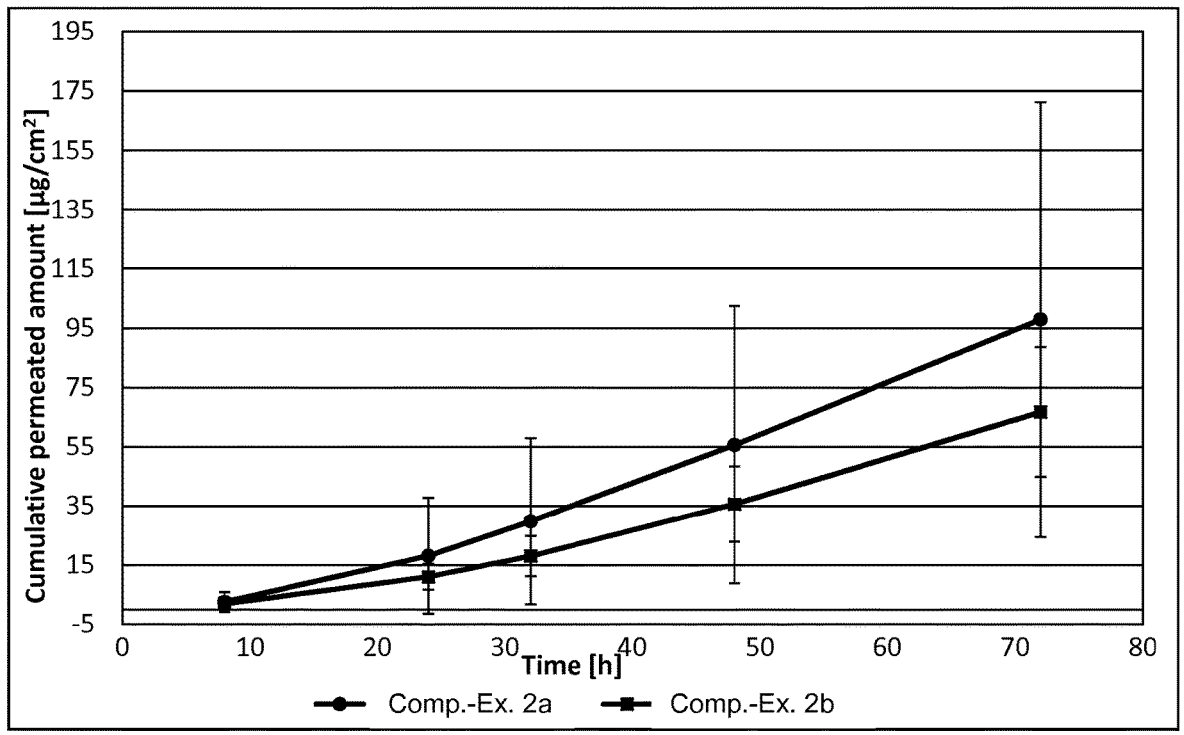
FIG. 11 depicts the guanfacine permeated amount of TTS prepared according to Comparative Examples 2a-b.

The results are shown in Table 12.2 and FIG. 11.

TABLE 12.2

Cumulative permeated amount with SD [µg/cm$^2$]

| Elapsed time [h] | Comp.-Ex. 2a (n = 2) Amount | Comp.-Ex. 2a (n = 2) SD | Comp.-Ex. 2b (n = 2) Amount | Comp.-Ex. 2b (n = 2) SD |
|---|---|---|---|---|
| 8 | 2.52 | 3.36 | 1.88 | 0.78 |
| 24 | 18.09 | 19.53 | 11.04 | 4.37 |
| 32 | 29.76 | 28.2 | 17.99 | 6.87 |
| 48 | 55.61 | 46.79 | 35.64 | 12.74 |
| 72 | 97.91 | 73.38 | 66.69 | 21.86 |

The Invention Relates in Particular to the Following Further Items

1. Transdermal therapeutic system for the transdermal administration of guanfacine comprising a guanfacine-containing layer structure, said guanfacine-containing layer structure comprising:
   A) a backing layer; and
   B) a guanfacine-containing layer;
   wherein the transdermal therapeutic system comprises at least one polymer and at least one additive selected from the group consisting of dispersing agents, permeation enhancers, and solubilizers.
2. Transdermal therapeutic system according to item 1,
   wherein the guanfacine-containing layer is a guanfacine-containing matrix layer comprising:
   i) guanfacine;
   ii) the at least one polymer; and
   iii) the at least one additive.
3. Transdermal therapeutic system according to any one of items 1 or 2,
   wherein the guanfacine-containing layer structure is self-adhesive and preferably does not comprise an additional skin contact layer.
4. Transdermal therapeutic system according to any one of items 1 to 3,
   wherein the at least one polymer is a pressure-sensitive adhesive polymer.
5. Transdermal therapeutic system according to any one of items 1 to 4,
   wherein the guanfacine-containing layer structure contains a therapeutically effective amount of guanfacine.
6. Transdermal therapeutic system according to any one of items 1 to 5,
   wherein the guanfacine in the guanfacine-containing layer structure is present in the form of the free base, which is preferably dispersed in the guanfacine-containing layer.
7. Transdermal therapeutic system according to any one of items 1 to 6,
   wherein the guanfacine-containing layer structure comprises guanfacine in an amount of from 1 to 100 mg/TTS, preferably from 8 to 72 mg/TTS.
8. Transdermal therapeutic system according to any one of items 1 to 7,
   wherein the guanfacine-containing layer comprises guanfacine in an amount of from 1 to 20%, more preferably from 3 to 16% by weight, based on the total weight of the guanfacine-containing layer, and/or wherein the at least one additive is present in an amount of from 0.5 to 10% by weight or from 1 to 10% by weight, based on the total weight of the guanfacine-containing layer.

9. Transdermal therapeutic system according to any one of items 1 to 8,
wherein the guanfacine-containing layer comprises the at least one polymer in an amount of from 20 to 97%, preferably from 30 to 94%, most preferably from 35 to 92% by weight based on the total weight of the guanfacine-containing layer.

10. Transdermal therapeutic system according to any one of items 1 to 9, wherein the at least one polymer is selected from the group consisting of silicone polymers, acrylate polymers, silicone acrylic hybrid polymers, polyisobutylenes, and styrene-isoprene-styrene block copolymers.

11. Transdermal therapeutic system according to any one of items 1 to 10, wherein the at least one polymer is selected from the group consisting of silicone polymers and silicone acrylic hybrid polymers.

12. Transdermal therapeutic system according to any one of items 1 to 11, wherein the guanfacine-containing layer comprises a first polymer selected from silicone polymers and silicone acrylic hybrid polymers, and optionally a second polymer selected from acrylate polymers, silicone acrylic hybrid polymers, and silicone polymers.

13. Transdermal therapeutic system according to any one of items 10 to 12, wherein the silicone polymer is obtainable by polycondensation of silanol endblocked polydimethylsiloxane with a silicate resin.

14. Transdermal therapeutic system according to any one of items 10 to 13, wherein the acrylate polymer is obtainable from one or more monomers selected from acrylic acid, butylacrylate, 2-ethylhexylacrylate, glycidylmethacrylate, 2-hydroxyethylacrylate, methylacrylate, methylmethacrylate, t-octylacrylamide, and vinylacetate, preferably from one or more monomers selected from ethylhexylacrylate, glycidylmethacrylate, 2-hydroxyethylacrylate, and vinylacetate.

15. Transdermal therapeutic system according to any one of items 10 to 14, wherein the silicone acrylic hybrid polymer comprises a silicone phase and an acrylate phase in a weight ratio of from 60:40 to 40:60.

16. Transdermal therapeutic system according to any one of items 10 to 15,
wherein the silicone acrylic hybrid polymer comprises a reaction product of a silicone polymer, a silicone resin and an acrylic polymer, wherein the acrylic polymer is covalently self-crosslinked and covalently bound to the silicone polymer and/or the silicone resin.

17. Transdermal therapeutic system according to any one of items 10 to 15,
wherein the silicone acrylic hybrid polymer is a silicone acrylic hybrid pressure-sensitive adhesive obtainable from
(a) a silicon-containing pressure-sensitive adhesive composition comprising acrylate or methacrylate functionality.

18. Transdermal therapeutic system according to any one of items 10 to 15 or 17,
wherein the silicone acrylic hybrid polymer is a silicone acrylic hybrid pressure-sensitive adhesive comprising the reaction product of
(a) a silicon-containing pressure-sensitive adhesive composition comprising acrylate or methacrylate functionality;
(b) an ethylenically unsaturated monomer; and
(c) an initiator.

19. Transdermal therapeutic system according to any one of items 17 or 18,
wherein the silicon-containing pressure-sensitive adhesive composition comprising acrylate or methacrylate functionality comprises the condensation reaction product of
(a1) a silicone resin, and
(a2) a silicone polymer, and
(a3) a silicon-containing capping agent comprising acrylate or methacrylate functionality.

20. Transdermal therapeutic system according to any one of items 17 to 19,
wherein the silicon-containing pressure-sensitive adhesive composition comprising acrylate or methacrylate functionality comprises the condensation reaction product of
(a1) a silicone resin, and
(a2) a silicone polymer, and
(a3) a silicon-containing capping agent comprising acrylate or methacrylate functionality,
wherein said silicon-containing capping agent is of the general formula $XYR'_bSiZ_{3-b}$, wherein X is a monovalent radical of the general formula AE, where E is —O— or —NH— and A is an acryl group or methacryl group, Y is a divalent alkylene radical having from 1 to 6 carbon atoms, R' is a methyl or a phenyl radical, Z is a monovalent hydrolysable organic radical or halogen, and b is 0 or 1;
wherein the silicone resin and silicone polymer are reacted to form a pressure-sensitive adhesive,
wherein the silicon-containing capping agent is introduced prior to, during, or after the silicone resin and silicone polymer are reacted,
and wherein the silicon-containing capping agent reacts with the pressure-sensitive adhesive after the silicone resin and silicone polymer have been condensation reacted to form the pressure-sensitive adhesive, or the silicon-containing capping agent reacts in situ with the silicone resin and silicone polymer.

21. Transdermal therapeutic system according to any one of items 18 to 20,
wherein the ethylenically unsaturated monomer is selected from the group consisting of aliphatic acrylates, aliphatic methacrylates, cycloaliphatic acrylates, cycloaliphatic methacrylates, and combinations thereof, each of said compounds having up to 20 carbon atoms in the alkyl radical, and wherein the ethylenically unsaturated monomer is preferably a combination of 2-ethylhexyl acrylate and methyl acrylate, particularly preferably in a ratio of from 40:60 to 70:30.

22. Transdermal therapeutic system according to any one of items 18 to 21,
wherein the reaction product of
(a) the silicon-containing pressure-sensitive adhesive composition comprising acrylate or methacrylate functionality;
(b) the ethylenically unsaturated monomer; and
(c) the initiator
contains a continuous, acrylic external phase and a discontinuous, silicone internal phase.

23. Transdermal therapeutic system according to any one of items 1 to 22, wherein the at least one additive is a dispersing agent, which is present in an amount of from 1 to 10% by weight, based on the total weight of the guanfacine-containing layer.

24. Transdermal therapeutic system according to any one of items 1 to 22, wherein the at least one additive is a permeation enhancer, which is present in an amount of from 1 to 10% by weight, based on the total weight of the guanfacine-containing layer.

25. Transdermal therapeutic system according to any one of items 1 to 22, wherein the at least one additive is a solubilizer, which is present in an amount of from 0.5 to 10% by weight, based on the total weight of the guanfacine-containing layer.

26. Transdermal therapeutic system according to any one of items 1 to 25, wherein the transdermal therapeutic system comprises at least two additives selected from the group consisting of dispersing agents, permeation enhancers, and solubilizers, in particular the combination of a dispersing agent and a permeation enhancer, or the combination of a dispersing agent and a solubilizer, or the combination of a permeation enhancer and a solubilizer.

27. Transdermal therapeutic system according to any one of items 1 to 26, wherein the transdermal therapeutic system comprises at least two additives, wherein the first additive is a dispersing agent, which is present in an amount of from 1 to 10% by weight, based on the total weight of the guanfacine-containing layer, and the second additive is a permeation enhancer, which is present in an amount of from 1 to 10% by weight, based on the total weight of the guanfacine-containing layer.

28. Transdermal therapeutic system according to any one of items 1 to 26, wherein the transdermal therapeutic system comprises at least two additives, wherein the first additive is a dispersing agent, which is present in an amount of from 1 to 10% by weight, based on the total weight of the guanfacine-containing layer, and the second additive is a solubilizer, which is present in an amount of from 0.5 to 10% by weight, based on the total weight of the guanfacine-containing layer.

29. Transdermal therapeutic system according to any one of items 1 to 26, wherein the transdermal therapeutic system comprises at least two additives, wherein the first additive is a permeation enhancer, which is present in an amount of from 1 to 10% by weight, based on the total weight of the guanfacine-containing layer, and the second additive is a solubilizer, which is present in an amount of from 0.5 to 10% by weight, based on the total weight of the guanfacine-containing layer.

30. Transdermal therapeutic system according to any one of items 1 to 29, wherein the transdermal therapeutic system comprises at least three additives selected from the group consisting of dispersing agents, permeation enhancers, and solubilizers, in particular the combination of a dispersing agent, a permeation enhancer and a solubilizer.

31. Transdermal therapeutic system according to any one of items 1 to 30, wherein the transdermal therapeutic system comprises at least three additives, wherein the first additive is a dispersing agent, which is present in an amount of from 1 to 10% by weight, based on the total weight of the guanfacine-containing layer, the second additive is a permeation enhancer, which is present in an amount of from 1 to 10% by weight, based on the total weight of the guanfacine-containing layer, and the third additive is a solubilizer, which is present in an amount of from 0.5 to 10% by weight, based on the total weight of the guanfacine-containing layer.

32. Transdermal therapeutic system according to any one of items 1 to 31, wherein the dispersing agent is selected from the group consisting of esters of fatty acids with polyols, fatty alcohols, polyethylene glycols having a number average molecular weight of from 300 to 400, polyethylene glycol alkyl ethers, and wherein the dispersing agent is preferably polyethylene glycol $C_8$-$C_{20}$-alkyl ether having from 2 to 10 EO units.

33. Transdermal therapeutic system according to any one of items 1 to 32, wherein the permeation enhancer is selected from the group consisting of diethylene glycol monoethyl ether (transcutol), oleic acid, levulinic acid, caprylic/capric triglycerides, diisopropyl adipate, isopropyl myristate, isopropyl palmitate, lauryl lactate, triacetin, dimethylpropylene urea, and oleyl alcohol, and is preferably oleyl alcohol.

34. Transdermal therapeutic system according to any one of items 1 to 33, wherein the solubilizer is selected from the group consisting of copolymers derived from esters of acrylic and methacrylic acid, polyvinylpyrrolidone, vinylpyrrolidone-vinyl acetate copolymers, and polyvinyl caprolactam-polyvinyl acetate-polyethylene glycol graft copolymers, and is preferably a polyvinyl caprolactam-polyvinyl acetate-polyethylene glycol graft copolymer.

35. Transdermal therapeutic system according to any one of items 1 to 34, wherein the transdermal therapeutic system comprises a polyethylene glycol $C_8$-$C_{20}$-alkyl ether having from 2 to 10 EO units in an amount of from 1 to 10% by weight, oleyl alcohol in an amount of from 1 to 10% by weight, and optionally a polyvinyl caprolactam-polyvinyl acetate-polyethylene glycol graft copolymer in an amount of from 0.5 to 10% by weight.

36. Transdermal therapeutic system according to any one of items 1 to 35,
wherein the area weight of the guanfacine-containing layer ranges from 40 to 250 g/m², preferably from 50 to 180 g/m².

37. Transdermal therapeutic system according to any one of items 1 to 36,
wherein the area of release ranges from 1 to 100 cm², preferably from 2.5 to 50 cm².

38. Transdermal therapeutic system according to any one of items 1 to 37,
wherein the guanfacine loading of the transdermal therapeutic system ranges from 0.2 to 2.4 mg/cm², preferably from 0.2 to 1.5 mg/cm².

39. Transdermal therapeutic system according to any one of items 1 to 38,
wherein the transdermal therapeutic system provides by transdermal delivery at steady state a mean plasma concentration of guanfacine of from 1 to 20 ng/ml, preferably from 1 to 15 ng/ml.

40. Transdermal therapeutic system according to any one of items 1 to 39,
having an $AUC_{0-24\,h}$ of 10 to 600 ng*h/ml, preferably of 20 to 400 ng*h/ml.

41. Transdermal therapeutic system according to any one of items 1 to 30,
having an $AUC_{0-72\,h}$ of 30 to 1800 ng*h/ml, preferably of 60 to 1200 ng*h/ml.

42. Transdermal therapeutic system according to any one of items 1 to 41,
having an $AUC_{0-84\,h}$ of 35 to 2100 ng*h/ml, preferably of 70 to 1400 ng*h/ml.

43. Transdermal therapeutic system according to any one of items 1 to 42,
having a $C_{max}$ to $C_{84}$ ratio of less than 3.5.

44. Transdermal therapeutic system according to any one of items 1 to 43,
having a $C_{max}$ to $C_{72}$ ratio of less than 3.0.

45. Transdermal therapeutic system according to any one of items 1 to 44,
having a $C_{max}$ to $C_{24}$ ratio of less than 2.0.

46. Transdermal therapeutic system according to any one of items 1 to 45,
providing a skin permeation rate of guanfacine as measured in a Franz diffusion cell with dermatomed human skin of
0.01 µg/(cm²*h) to 8 µg/(cm²*h) in the first 24 hours,
0.05 µg/(cm²*h) to 10 µg/(cm²*h) from hour 24 to hour 72.
47. Transdermal therapeutic system according to any one of items 1 to 46,
providing a cumulative permeated amount of guanfacine as measured in a Franz diffusion cell with dermatomed human skin of 0.01 mg/cm² to 0.7 mg/cm², preferably 0.05 mg/cm² to 0.6 mg/cm², more preferably 0.15 to 0.3 mg/cm² over a time period of 72 hours.
48. Transdermal therapeutic system according to any one of items 1 to 47 for use in a method of treating a human patient, preferably a human patient at the age of from 6 to 17.
49. Transdermal therapeutic system according to any one of items 1 to 47 for use in a method of treating hypertension or attention deficit hyperactivity disorder (ADHD) and/or as adjunctive therapy to stimulant medications in a human patient, preferably in a human patient at the age of from 6 to 17.
50. Transdermal therapeutic system for use according to any one of items 48 or 49, wherein the transdermal therapeutic system is applied to the skin of the patient for at least 24 hours, preferably at least 72 hours, more preferably about 84 hours.
51. Method of treating a human patient, preferably a human patient at the age of from 6 to 17, by applying a transdermal therapeutic system as defined in any one of items 1 to 47 to the skin of the patient.
52. Method of treating hypertension or attention deficit hyperactivity disorder (ADHD) in a human patient, preferably a human patient at the age of from 6 to 17, by applying a transdermal therapeutic system as defined in any one of items 1 to 47 to the skin of the patient.
53. Method of treating a human patient according to any one of items 51 or 52, wherein the transdermal therapeutic system is applied to the skin of the patient for at least 24 hours, preferably at least 72 hours, more preferably about 84 hours.
54. Transdermal therapeutic system for the transdermal administration of guanfacine comprising a guanfacine-containing layer structure,
wherein the transdermal therapeutic system provides by transdermal delivery one or more pharmacokinetic parameter(s) selected from the group consisting of
an $AUC_{0-24}$ from 10 to 600 (ng/mL) h,
an $AUC_{0-72}$ from 30 to 1800 (ng/mL) h,
an $AUC_{0-84}$ from 35 to 2100 (ng/mL) h,
a $C_{max}$ to $C_{24}$ ratio of less than 2.0,
a $C_{max}$ to $C_{72}$ ratio of less than 3.0, and
a $C_{max}$ to $C_{84}$ ratio of less than 3.5.
55. Transdermal therapeutic system according to item 54,
wherein the transdermal therapeutic system provides by transdermal delivery one or more pharmacokinetic parameter(s) selected from the group consisting of
an $AUC_{0-24}$ from 20 to 400 (ng/mL) h,
an $AUC_{0-72}$ from 60 to 1200 (ng/mL) h,
an $AUC_{0-84}$ from 70 to 1400 (ng/mL) h,
a $C_{max}$ to $C_{24}$ ratio of less than 1.5,
a $C_{max}$ to $C_{72}$ ratio of less than 2.5, and
a $C_{max}$ to $C_{84}$ ratio of less than 3.0.
56. Transdermal therapeutic system comprising guanfacine for use in a method of treating a human patient, preferably a human patient at the age of from 6 to 17, by transdermal administration of guanfacine, wherein the transdermal therapeutic system is applied to the skin of a patient for at least 24 hours, preferably at least 72 hours, more preferably about 84 hours.
57. Transdermal therapeutic system comprising guanfacine for use according to item 56, wherein the transdermal therapeutic system is for use in a method of treating hypertension or attention deficit hyperactivity disorder (ADHD) and/or as adjunctive therapy to stimulant medications in a human patient.
58. Transdermal therapeutic system comprising guanfacine for use according to item 56 or 57, wherein the transdermal therapeutic system is a transdermal therapeutic system according to any one of items 54 or 55.
59. Guanfacine for use in a method of treating a human patient, preferably a human patient at the age of from 6 to 17, by transdermal administration of guanfacine with a transdermal therapeutic system, wherein the transdermal therapeutic system is applied to the skin of a patient for at least 24 hours, preferably at least 72 hours, more preferably about 84 hours.
60. Guanfacine for use according to item 59, wherein the guanfacine is for use in a method of treating hypertension or attention deficit hyperactivity disorder (ADHD) and/or as adjunctive therapy to stimulant medications in a human patient.
61. Guanfacine for use according to item 59 or 60, wherein the guanfacine is administered by applying a transdermal therapeutic system according to any one of items 44 or 45.
62. A method of treating a human patient, preferably a human patient at the age of from 6 to 17, by transdermal administration of guanfacine, wherein the transdermal therapeutic system is applied to the skin of a patient for at least 24 hours, preferably at least 72 hours, more preferably about 84 hours.
63. The method of treating a human patient by transdermal administration of guanfacine according to item 62, wherein the method is for treating hypertension or attention deficit hyperactivity disorder (ADHD) and/or as adjunctive therapy to stimulant medications in a human patient.
64. The method of treating a human patient by transdermal administration of guanfacine according to any one of items 62 or 63, wherein the guanfacine is administered by applying a transdermal therapeutic system according to any one of items 54 or 55.
65. A process for manufacturing a guanfacine-containing layer for use in a transdermal therapeutic system according to any one of items 1 to 47 or 54 or 55 comprising the steps of:
1) combining at least the components
   i) guanfacine;
   ii) at least one polymer; and
   iii) at least one additive selected from dispersing agents, permeation enhancers, and solubilizers;
   to obtain a coating composition;
2) coating the coating composition onto a backing layer or a release liner to obtain a coated coating composition; and
3) drying the coated coating composition to form the guanfacine-containing layer.
66. Process for manufacturing a guanfacine-containing layer according to item 65, wherein the at least one polymer is provided as a solution, wherein the solvent comprises ethyl acetate or n-heptane.
67. Transdermal therapeutic system obtainable by a process in accordance with any one of items 55 or 56.

68. Transdermal therapeutic system for the transdermal administration of guanfacine comprising a guanfacine-containing layer structure, said guanfacine-containing layer structure comprising:
A) a backing layer; and
B) a guanfacine-containing layer, preferably a guanfacine-containing matrix layer, comprising
i) guanfacine in an amount of from 3 to 13% by weight, based on the total weight of the guanfacine-containing layer;
ii) at least one silicone acrylic hybrid polymer in an amount of from 74 to 89% by weight, based on the total weight of the guanfacine-containing layer;
iii) at least one dispersing agent in an amount of from 2 to 6% by weight, based on the total weight of the guanfacine-containing layer;
iv) at least one permeation enhancer in an amount of from 2 to 6% by weight, based on the total weight of the guanfacine-containing layer; and
v) optionally at least one solubilizer in an amount of from 0.5 to 4% by weight, based on the total weight of the guanfacine-containing layer.

69. Transdermal therapeutic system according to item 68, wherein the guanfacine-containing layer is a guanfacine-containing matrix layer, which comprises
i) guanfacine in an amount of from 3 to 13% by weight, based on the total weight of the guanfacine-containing layer;
ii) at least one silicone acrylic hybrid polymer in an amount of from 74 to 89% by weight, based on the total weight of the guanfacine-containing layer;
iii) a polyethylene glycol $C_8$-$C_{20}$-alkyl ether having from 2 to 10 EO units in an amount of from 2 to 6% by weight, based on the total weight of the guanfacine-containing layer;
iv) oleyl alcohol in an amount of from 2 to 6% by weight, based on the total weight of the guanfacine-containing layer; and
v) optionally a polyvinyl caprolactam-polyvinyl acetate-polyethylene glycol graft copolymer in an amount of from 0.5 to 4% by weight, based on the total weight of the guanfacine-containing layer.

70. Transdermal therapeutic system according to item 68 or 69, wherein the guanfacine-containing layer is a guanfacine-containing matrix layer, which comprises
i) guanfacine in an amount of from 11 to 13% by weight, based on the total weight of the guanfacine-containing layer;
ii) a first silicone acrylic hybrid polymer in an amount of from 73 to 75% by weight, based on the total weight of the guanfacine-containing layer, and a second silicone acrylic hybrid polymer in an amount of from 3 to 5% by weight, based on the total weight of the guanfacine-containing layer;
iii) a polyethylene glycol $C_8$-$C_{20}$-alkyl ether having from 2 to 10 EO units, preferably polyoxyethylene (4) lauryl ether, in an amount of from 3 to 5% by weight, based on the total weight of the guanfacine-containing layer;
iv) oleyl alcohol in an amount of from 3 to 5% by weight, based on the total weight of the guanfacine-containing layer; and
v) a polyvinyl caprolactam-polyvinyl acetate-polyethylene glycol graft copolymer in an amount of from 0.5 to 3% by weight, based on the total weight of the guanfacine-containing layer.

71. Transdermal therapeutic system according to item 70, wherein the weight ratio of silicone phase to acrylate phase in the first silicone acrylic hybrid polymer is from 55:45 to 45:55, and wherein the ethylenically unsaturated monomers forming the acrylate comprise 2-ethylhexyl acrylate and methyl acrylate in a ratio of from 55:45 to 45:55.

72. Transdermal therapeutic system according to item 70 or 71, wherein the weight ratio of silicone phase to acrylate phase in the second silicone acrylic hybrid polymer is from 55:45 to 45:55, and wherein the ethylenically unsaturated monomers forming the acrylate comprise 2-ethylhexyl acrylate and methyl acrylate in a ratio of from 65:35 to 55:45.

73. Transdermal therapeutic system according to any one of items 70 to 72, wherein in both silicone acrylic hybrid polymers, the silicone phase is the internal phase and the acrylate phase is the external phase.

74. Transdermal therapeutic system according to item 68 or 69, wherein the guanfacine containing-layer is a guanfacine-containing matrix layer, which comprises
i) guanfacine in an amount of from 5 to 7% by weight, based on the total weight of the guanfacine-containing layer;
ii) a first silicone acrylic hybrid polymer in an amount of from 79 to 83% by weight, based on the total weight of the guanfacine-containing layer, and a second silicone acrylic hybrid polymer in an amount of from 3 to 5% by weight, based on the total weight of the guanfacine-containing layer;
iii) a polyethylene glycol $C_8$-$C_{20}$-alkyl ether having from 2 to 10 EO units, preferably polyoxyethylene (4) lauryl ether, in an amount of from 3 to 5% by weight, based on the total weight of the guanfacine-containing layer; and
iv) oleyl alcohol in an amount of from 3 to 5% by weight, based on the total weight of the guanfacine-containing layer.

75. Transdermal therapeutic system according to item 74, wherein the weight ratio of silicone phase to acrylate phase in the first silicone acrylic hybrid polymer is from 55:45 to 45:55, and wherein the ethylenically unsaturated monomers forming the acrylate comprise 2-ethylhexyl acrylate and methyl acrylate in a ratio of from 55:45 to 45:55.

76. Transdermal therapeutic system according to item 74 or 75, wherein the weight ratio of silicone phase to acrylate phase in the second silicone acrylic hybrid polymer is from 55:45 to 45:55, and wherein the ethylenically unsaturated monomers forming the acrylate comprise 2-ethylhexyl acrylate and methyl acrylate in a ratio of from 65:35 to 55:45.

77. Transdermal therapeutic system according to any one of items 74 to 76, wherein in both silicone acrylic hybrid polymers, the silicone phase is the internal phase and the acrylate phase is the external phase.

78. Transdermal therapeutic system according to any one of items 68 to 77, wherein the area weight of the guanfacine-containing layer ranges from 80 to 120 $g/m^2$, preferably from 90 to 100 $g/m^2$.

The invention claimed is:
1. A transdermal therapeutic system for the transdermal administration of guanfacine comprising a guanfacine-containing layer structure, said guanfacine-containing layer structure comprising:
A) a backing layer; and
B) a guanfacine-containing layer;
wherein the transdermal therapeutic system comprises at least one polymer and a combination of a dispersing agent, a permeation enhancer, and a solubilizer;
wherein the dispersing agent is a polyethylene glycol $C_8$-$C_{20}$-alkyl ether having from 2 to 10 EO units, the permeation enhancer is oleyl alcohol, and the solubilizer is a polyvinyl caprolactam-polyvinyl acetate-polyethylene glycol graft copolymer.

2. The transdermal therapeutic system according to claim 1, wherein the guanfacine-containing layer is a guanfacine-containing matrix layer comprising:
   i) guanfacine;
   ii) the at least one polymer; and
   iii) the combination of the dispersing agent, the penetration enhancer, and the solubilizer.

3. The transdermal therapeutic system according to claim 1, wherein the guanfacine-containing layer structure is self-adhesive.

4. The transdermal therapeutic system according to claim 1, wherein the guanfacine in the guanfacine-containing layer structure is guanfacine free base dispersed in the guanfacine-containing layer, and
   wherein the guanfacine-containing layer structure further comprises from 1 to 100 mg/TTS guanfacine.

5. The transdermal therapeutic system according to claim 1, wherein the guanfacine-containing layer comprises from 1 to 20% guanfacine by weight, based on the total weight of the guanfacine-containing layer.

6. The transdermal therapeutic system according to claim 1, wherein the guanfacine-containing layer comprises from 20 to 97% of the at least one polymer by weight, based on the total weight of the guanfacine-containing layer, and wherein the at least one polymer is selected from the group consisting of silicones, acrylates, silicone acrylic hybrid polymers, polyisobutylenes, and styrene-isoprene-styrene block copolymers.

7. The transdermal therapeutic system according to claim 1, wherein the dispersing agent is present in an amount of from 1 to 10% by weight, based on the total weight of the guanfacine-containing layer, the permeation enhancer is present in an amount of from 1 to 10% by weight, based on the total weight of the guanfacine-containing layer, and the solubilizer is present in an amount of from 0.5 to 10% by weight, based on the total weight of the guanfacine-containing layer.

8. The transdermal therapeutic system according to claim 1, wherein the guanfacine-containing layer has (i) an area weight ranging from 40 to 250 g/m², (ii) an area of release ranging from 1 to 100 cm², or both (i) and (ii).

9. The transdermal therapeutic system according to claim 1, wherein the transdermal therapeutic system provides by transdermal delivery at steady state a plasma concentration of guanfacine of from 1 to 20 ng/ml.

10. The transdermal therapeutic system according to claim 1, wherein the transdermal therapeutic system provides at least one pharmacokinetic parameter selected from the group consisting of:
    an $AUC_{0-24h}$ of about 10 to 600 ng*h/ml;
    an $AUC_{0-72h}$ of about 30 to 1800 ng*h/ml;
    an $AUC_{0-84h}$ of about 35 to 2100 ng*h/ml;
    a $C_{max}$ to $C_{84}$ ratio of less than 3.5;
    a $C_{max}$ to $C_{72}$ ratio of less than 3.0; and
    a $C_{max}$ to $C_{24}$ ratio of less than 2.0.

* * * * *